United States Patent
Zheng et al.

(10) Patent No.: US 9,334,483 B2
(45) Date of Patent: May 10, 2016

(54) BRASSICA PLANTS WITH MUTANT FATA2 ALLELES YIELDING OILS WITH A LOW TOTAL SATURATED FATTY ACID CONTENT

(75) Inventors: Honggang Zheng, Fort Collins, CO (US); Kevin Brandt, Longmont, CO (US); Richard Fletcher, Windsor, CO (US); Daren Kenneth Coonrod, Aurora, IL (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 13/516,936

(22) PCT Filed: Dec. 20, 2010

(86) PCT No.: PCT/US2010/061226
§ 371 (c)(1), (2), (4) Date: Jun. 26, 2012

(87) PCT Pub. No.: WO2011/075716
PCT Pub. Date: Jun. 23, 2011

(65) Prior Publication Data
US 2013/0031678 A1 Jan. 31, 2013

Related U.S. Application Data

(60) Provisional application No. 61/287,985, filed on Dec. 18, 2009, provisional application No. 61/295,049, filed on Jan. 14, 2010.

(51) Int. Cl.
| | | |
|---|---|---|
| *C12N 9/16* | (2006.01) | |
| *A01H 5/10* | (2006.01) | |
| *A01H 1/00* | (2006.01) | |
| *A01H 3/00* | (2006.01) | |
| *C12Q 1/68* | (2006.01) | |

(52) U.S. Cl.
CPC .. *C12N 9/16* (2013.01); *A01H 1/00* (2013.01); *A01H 3/00* (2013.01); *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,948,811 A | 8/1990 | Spinner et al. | |
| 5,387,758 A | 2/1995 | Wong et al. | |
| 5,434,283 A | 7/1995 | Wong et al. | |
| 5,545,821 A | 8/1996 | Wong et al. | |
| 5,625,130 A | 4/1997 | Grant et al. | |
| 5,644,066 A | 7/1997 | Sakai et al. | |
| 5,668,299 A | 9/1997 | DeBonte et al. | |
| 5,750,827 A | 5/1998 | DeBonte et al. | |
| 5,767,338 A | 6/1998 | Fan | |
| 5,850,026 A | 12/1998 | DeBonte et al. | |
| 5,859,350 A | 1/1999 | DeBonte et al. | |
| 5,863,589 A | 1/1999 | Covington, Jr. et al. | |
| 5,866,762 A | 2/1999 | DeBonte et al. | |
| 5,885,643 A | 3/1999 | Kodali et al. | |
| 5,955,623 A | 9/1999 | Grant et al. | |
| 5,965,755 A | 10/1999 | Sernyk et al. | |
| 6,011,164 A | 1/2000 | Grant et al. | |
| 6,229,072 B1 | 5/2001 | Burns et al. | |
| 6,303,849 B1 | 10/2001 | Potts et al. | |
| 6,323,392 B1 | 11/2001 | Charne | |
| 6,342,658 B1 | 1/2002 | DeBonte et al. | |
| 6,392,127 B1 | 5/2002 | Charne et al. | |
| 6,489,543 B1 | 12/2002 | Sernyk | |
| 6,562,397 B2 | 5/2003 | DeBonte et al. | |
| 6,737,564 B2 | 5/2004 | Yao et al. | |
| 6,787,686 B2 | 9/2004 | Potts et al. | |
| 6,967,243 B2 | 11/2005 | DeBonte et al. | |
| 7,081,564 B2 | 7/2006 | Somers et al. | |
| 7,109,392 B1 | 9/2006 | Broglie et al. | |
| 7,566,813 B2 | 7/2009 | Voelker et al. | |
| 7,741,542 B2 | 6/2010 | DeBonte et al. | |
| 7,790,959 B2 | 9/2010 | Kishore et al. | |
| 8,057,835 B2 | 11/2011 | Makadia et al. | |
| 8,088,978 B2 | 1/2012 | Vrinten et al. | |
| 8,304,610 B2 | 11/2012 | Yao et al. | |
| 2003/0221217 A1 | 11/2003 | Yao et al. | |
| 2005/0039233 A1 | 2/2005 | Yao et al. | |
| 2006/0206963 A1 | 9/2006 | Voelker et al. | |
| 2007/0065565 A1 | 3/2007 | Kincs et al. | |
| 2008/0260933 A1 | 10/2008 | Thompson et al. | |
| 2009/0019601 A1 | 1/2009 | Kovalic | |
| 2010/0143570 A1 | 6/2010 | Ripley et al. | |
| 2012/0246755 A1 | 9/2012 | Laga et al. | |

FOREIGN PATENT DOCUMENTS

| | | | | |
|---|---|---|---|---|
| BE | WO-2009/007091 | * | 1/2009 | ............. C12N 15/82 |
| CA | 225398 A | | 10/1922 | |
| CA | 2340611 A1 | | 4/1993 | |
| CA | 2462725 A1 | | 4/1993 | |
| CA | 1337251 | | 10/1995 | |
| CA | 2056988 | | 12/1995 | |
| CA | 2382767 A1 | | 11/2003 | |
| CA | 2180386 | | 9/2006 | |
| WO | 9203919 | | 3/1992 | |
| WO | 9311245 | | 6/1993 | |
| WO | 9318158 | | 9/1993 | |
| WO | WO 93/18158 | * | 9/1993 | ............. C12N 15/55 |

(Continued)

OTHER PUBLICATIONS

McCallum et al 2000 Plant Physiology 123: p. 439-442.*

(Continued)

*Primary Examiner* — Brent T Page
*Assistant Examiner* — Matthew Keogh

(57) ABSTRACT

*Brassica* plants producing oils with a low total saturated fatty acid content and methods for producing such plants are described. The oils have a low total saturated fatty acid in combination with a low, mid, or high oleic acid content.

19 Claims, 2 Drawing Sheets

(56) References Cited

FOREIGN PATENT DOCUMENTS

| | | |
|---|---|---|
| WO | 9424849 | 11/1994 |
| WO | 9627285 | 9/1996 |
| WO | 9721340 | 6/1997 |
| WO | 9743907 | 11/1997 |
| WO | 9850569 | 11/1998 |
| WO | 9855633 | 12/1998 |
| WO | 9856239 | 12/1998 |
| WO | 0009721 | 2/2000 |
| WO | 0138502 | 5/2001 |
| WO | 2007016521 A2 | 2/2007 |
| WO | 2007107590 A2 | 9/2007 |
| WO | 2008135296 A2 | 11/2008 |
| WO | 2009007091 A2 | 1/2009 |
| WO | 2011060946 A1 | 5/2011 |
| WO | 2011075716 A1 | 6/2011 |

OTHER PUBLICATIONS

Facciotti et al 1998 (Fett/ Lipid 100: p. 167-172).*

Hohe et al 2003 (Plant Cell Reports 21:1135-1142).*

Arondel, V., et al., "Map-Based Cloning of a Gene Controlling Omega-3 Fatty Acid Desaturation in Arabidopsis," Science 258:1353-1355 (1992).

Barker, G. C., et al., "Novel Insights into Seed Fatty Acid Synthesis and Modification Pathways from Genetic Diversity and Quantitative Trait Loci Analysis of the Brassica C Genome1[OA]," Plant Physiology 144:1827-1842 (2007).

Bonaventure, G., et al., "Disruption of the FATB Gene in Arabidopsis Demonstrates an Essential Role of Saturated Fatty Acids in Plant Growth," Plant Cell 15:1020-1033 (2003).

Chenna, R., et al., "Multiple Sequence Alignment with the Clustal Series of Programs," Nucleic Acids Res. 31 (13):3497-3500 (2003).

Eccleston, V. S., et al., "Expression of Lauroyl—Acyl Carrier Protein Thioesterase in Brassica Napus Seeds Induces Pathways for Both Fatty Acid Oxidation and Biosynthesis and Implies a Set Point for Triacylglycerol Accumulation," Plant Cell 10:613-621 (1998).

GenBank Deposit AY599884. Brassica cDNA, RiceGE: Genome Express Database, Oct. 6, 2010.

Ginalski, K, et al., "Detection of Reliable and Unexpected Protein Fold Predictions Using 3D-Jury," Nucleic Acids Res. 31(13):3291-3292 (2003).

Goren, M. A., et al., "Wheat Germ Cell-Free Translation, Purification, and Assembly of a Functional Human Stearoyl-Coa Desaturase Complex," Protein Expr. Purif. 62(2):171-178 (2008).

Hawrysh, Z. J., "Stability of Canola Oil," Canola and Rapeseed: Production Chemistry, Nutrition and Processing Technology, Van Nostrand, Reinhold, N. Y., Ch. 7, pp. 99-122 (1990).

Jones, A., et al., "Palmitoyl-Acyl Carrier Protein (ACP) Thioesterase and the Evolutionary Origin of Plant Acyl-ACP Thioesterases," Plant Cell 7:359-371 (1995).

Lloyd, A., et al., "Targeted Mutagenesis Using Zinc-Finger Nucleases in Arabidopsis," PNAS 102:2232-2237 (2005).

Lysak, M. A., et al., "Chromosome Triplication Found Across the Tribe Brassiceae," Genome Res. 15:516-525 (2005).

Mayer, K. M., et al., "Identification of Amino Acid Residues Involved in Substrate Specificity of Plant Acyl-ACP Thioesterases Using a Bioinformatics-Guided Approach," BMC Plant Biol. 7:1, doi:10. 1186/1471-2229-7-1 (2007).

Mayer, K. M., et al., "Lipids and Lipoproteins: A Structural Model of the Plant Acyl-Acyl Carrier Protein Thioesterase FatB Comprises Two Helox/4-Stranded Sheet Domains, the N-Terminal Domain Containing Residues that Affect Specificity and the C-Terminal Domain Containing Catalytic Residues," J. Biol. Chem. 280:3621-3627 (2005).

McCallum, C. M., et al., "Targeting Induced Local Lesions IN Genomes (TILLING) for Plant Functional Genomics," Plant Physiology 123:439-442 (2000).

Mounts, T. L., "Odor Considerations in the Use of Frying Oils," J. Amer. Oil Chemists' Soc. 56:659-663 (1979).

Pellan-Delourme, R., et al., "Cytoplasmic Male Sterility in Rapeseed (Brassica Napus L.): Female Fertility of Restored Rapeseed with "Ogura" and Cybrids Cytoplasms," Genome 30:234-238 (1988).

Riungu, T. C., et al., "Development and Evaluation of Diplotaxis Muralis (mur) Cytoplasmic Male Sterility System in Summer Rape," Can. J. Plant Sci. 83:261-269 (2003).

Tovkach, A., et al., "A Toolbox and Procedural Notes for Characterizing Novel Zinc Finger Nucleases for Genome Editing in Plant Cells," Plant J. 57:747-757 (2009).

Townsend, J. A., et al., "High Frequency Modification of Plant Genes Using Engineered Zinc Finger Nucleases," Nature 459(7245):442-445 (2009).

United States Patent and Trademark Office, International Search Report and Written Opinion dated May 4, 2011 for PCT/US2010/061226.

United States Patent and Trademark Office, International Search Report and Written Opinion dated Dec. 1, 2011 for PCT/US2011/037864.

United States Patent and Trademark Office, International Search Report and Written Opinion dated Dec. 20, 2011 for PCT/US2011/045235.

Voelker, T., "Plant Acyl-Acp Thioesterases: Chain-Length Determining Enzymes in Plant Fatty Acid Biosynthesis," Genetic Engineering 118:111-133 (1996).

Yadav, N. S., et al., "Cloning of Higher Plant w-3 Fatty Acid Desaturases," Plant Physiol. 103:467-476 (1993).

Serrano-Vega, et al., "Cloning, characterization and structural model of a FatA-type thioesterase from sunflower seeds (Helianthus annuus L.)", Planta, Aug. 2005, vol. 221, Issue 6, pp. 868-880.

Moreno-Pérez et al., "Acyl-ACP thioesterases from macadamia (Macadamia tetraphylla) nuts: Cloning, characterization and their impact on oil composition", Plant Physiology and Biochemistry (PPB), Elsevier, vol. 49 (2011), pp. 82-87.

* cited by examiner

FIGURE 1

```
Brapa FatA1    CTCAGTATTCGATGATTGGGCTTAAGCCTAGAGCTGATCTCGACATGAACCAGGATGTCAATAATGTCACCTATATTGGATGG
AtFatA1        CTCAGTATTCAATGATTGGGCTTAAGCCTAGAGCTGATCTCGACATGAACCAGGATGTCAATAATGTCACCTATATTGGATGG
BnFatA1 1524   CTCAGTATTAATGTTTCTTTGC--AGCTAGCTTAAGCCTAGAGCTGATCTCGACATGAACCAGCATCATGTCAATAATGTCACCTATATTGGATGG
BnFatA2 1524   CTCAGTATTCTATGCTAGCTTAAGCCTAGAGCTGATCTCGACATGAACCAGCATCATGTCAATAACGTCACCTATATTGGATGG
AtFatA2        CTCAGTATTCTATGCTAGCTTAAGCCTAGAGCTGATCTCGGCGAGCTGATCTTGACATGAACCAGCATCATGTCAATAATGTCACCTACATTGGATGG
Bnapus pNL2    CTCAGTATTCTATGCTAGCTTAAGCCTCGGCGAGCTGATCTGGCGAGCTGATCTCGACATGAACCAGCATCATGTCAATAACGTCACCTACATTGGATGG
                                         1                                                       2
```

FIGURE 2

```
AtFatA2         TTAAGCCTAGACGAGCTGATCTCTTGACATGAACCAACATGTGAATAATGTTACCTACATTGGATGGG
15..24FatA2(1)  TTAAGCCTAGAFTCGGCGAGCTGATCTGGACATGAACCAGCACGTCAACGTCACCTACATTGGATGGG
15..24FatA2(2)  TTAAGCCTTCGGCGAGCTGATCTGGACATGAACCAGCACGTCAATAACGTCACCTACATCGGATGGG
OB240FatA2(1)   TTAAGCCTCGGCGAGCTGATCTGGACATGAACCAGCACGTCAATAACGTCACCTACATCGGATGGG
OB240FatA2(2)   TTAAGCCTCGGCGAGCTGATCTGGACATGAACCAGCACGTCAATAACGTCACCTACATTGGATGGG
                      1                                                    2
```

FIGURE 3

```
AtFatA2         LEDPAQYSMLGLKPRRADLDMNQHVNNVTYIGWVLE
15..24FatA2(1)  LEDPAQYSMLELKLRRADLDMNQHVNNVTYIGWVLE
15..24FatA2(2)  LEDPAQYSMLELKPRRADLDMNQHVNNVTYIGWVLE
OB240FatA2(1)   LEDPAQYSMLELKPRRADLDMNQHVNNVTYIGWVLE
OB240FatA2(2)   LEDPAQYSMLELKPRRADLDMNQHVNNVTYIGWVLE
                          1                 2
```

FIGURE 4

BRASSICA PLANTS WITH MUTANT FATA2 ALLELES YIELDING OILS WITH A LOW TOTAL SATURATED FATTY ACID CONTENT

CROSS-REFERENCE TO RELATED APPLICATION

This application claims the benefit of U.S. Provisional Application No. 61/287,985, filed Dec. 18, 2009, and U.S. Provisional Application No. 61/295,049, filed Jan. 14, 2010. The contents of the foregoing applications are hereby incorporated by reference in their entireties.

TECHNICAL FIELD

This invention relates to *Brassica* plants, and more particularly, *Brassica* plants having modified alleles at fatty acyl-acyl carrier protein thioesterase A2 (FATA2) loci and/or fatty acyl-acyl carrier protein thioesterase B (FATB) loci and yielding an oil with a low total saturated fatty acid content in combination with a typical, mid, or high oleic acid content.

BACKGROUND

In recent years, diets high in saturated fats have been associated with increased levels of cholesterol and increased risk of coronary heart disease. As such, current dietary guidelines indicate that saturated fat intake should be no more than 10 percent of total calories. Based on a 2,000-calorie-a-day diet, this is about 20 grams of saturated fat a day. While canola oil typically contains only about 7% to 8% saturated fatty acids, a decrease in its saturated fatty acid content would improve the nutritional profile of the oil.

SUMMARY

This document is based on the discovery of mutant FATA2 and FATB alleles, and use of such alleles in *Brassica* plants to control total saturated fatty acid content. As described herein, *Brassica* plants containing such alleles can produce oils with a low total saturated fatty acid content (i.e., 6% or less total saturates) or oils having very low saturates (i.e., having 3.6% or less total saturates). Such *Brassica* plants also can include mutant fatty acid desaturase alleles to tailor the oleic acid and α-linolenic acid content to the desired end use of the oil. *Brassica* plants described herein are particularly useful for producing canola oils for certain food applications as the plants are not genetically modified.

This document features *Brassica* plants (e.g., *Brassica napus, Brassica juncea*, or *Brassica rapa* plants) and progeny thereof (e.g., seeds) that include modified alleles at two or more different fatty acyl-acyl carrier protein thioesterase B (FATB) loci (e.g., three or four different loci), wherein each modified allele results in the production of a FATB polypeptide having reduced thioesterase activity relative to a corresponding wild-type FATB polypeptide. The plant can be an $F_1$ hybrid. A modified allele can include a nucleic acid encoding a truncated FATB polypeptide. A modified allele can include a nucleic acid encoding a FATB polypeptide having a deletion of a helix/4-stranded sheet (4HBT) domain or a portion thereof. A modified allele can include a nucleic acid encoding a FATB polypeptide having a non-conservative substitution of a residue affecting substrate specificity. A modified allele can include a nucleic acid encoding a FATB polypeptide having a non-conservative substitution of a residue affecting catalytic activity. Any of the modified alleles can be a mutant allele.

In some embodiments, the nucleic acid encoding a truncated FATB polypeptide includes a nucleotide sequence selected from the group consisting of: SEQ ID NO:1, SEQ ID NO:2, SEQ ID NO:3, and SEQ ID NO:4. In some embodiments, the plant contains nucleic acids having the nucleotide sequences set forth in SEQ ID NO:1 and SEQ ID NO:2; SEQ ID NO:1 and SEQ ID NO:3; SEQ ID NO:1 and SEQ ID NO:4; SEQ ID NO:1, SEQ ID NO:2, and SEQ ID NO:3; SEQ ID NO:1, SEQ ID NO:2, and SEQ ID NO:4; SEQ ID NO:1, SEQ ID NO:3, and SEQ ID NO:4; or SEQ ID NO:1, SEQ ID NO:2, SEQ ID NO:3, and SEQ ID NO:4.

A plant can produce seeds yielding an oil having a total saturates content of about 2.5 to 5.5%. The palmitic acid content of the oil can be about 1.5 to 3.5%. The stearic acid content of the oil can be about 0.5 to 2.5%. The oil can have an oleic acid content of about 78 to 80%, a linoleic acid content of about 8 to 10%, and an α-linolenic acid content of no more than about 4% (e.g., about 2 to 4%).

This document also features *Brassica* plants (e.g., *Brassica napus, Brassica juncea*, or *Brassica rapa* plants) and progeny thereof (e.g., seeds) that include a modified allele at a fatty acyl-ACP thioesterase A2 (FATA2) locus, wherein the modified allele results in the production of a FATA2 polypeptide (e.g., FATA2b polypeptide) having reduced thioesterase activity relative to a corresponding wild-type FATA2 polypeptide. The modified allele can include a nucleic acid encoding a FATA2 polypeptide having a mutation in a region (SEQ ID NO:29) corresponding to amino acids 242 to 277 of an *Arabidopsis* FATA2 polypeptide. The FATA2 polypeptide can include a substitution of a leucine residue for proline at position 255. The plant can be an $F_1$ hybrid. Any of the modified alleles can be a mutant allele.

Any of the plants described herein further can include one or more modified (e.g., mutant) alleles at FAD2 loci. For example, a mutant allele at a FAD2 loci can include a nucleic acid encoding a FAD2 polypeptide having a lysine substituted for glutamic acid in a HECGH (SEQ ID NO:5) motif. A mutant allele at a FAD2 locus can include a nucleic acid encoding a FAD2 polypeptide having a glutamic acid substituted for glycine in a DRDYGILNKV (SEQ ID NO:7) motif or a histidine substituted for leucine in a KYLNNP (SEQ ID NO:6) motif. In some embodiments, the plant contains a mutant allele at two different FAD2 loci, a mutant allele including a nucleic acid encoding a FAD2 polypeptide having a lysine substituted for glutamic acid in a HECGH motif and a mutant allele including a nucleic acid encoding a FAD2 polypeptide having a glutamic acid substituted for glycine in a DRDYGILNKV motif or a histidine substituted for leucine in a KYLNNP motif.

Any of the plants described herein further can include modified alleles (e.g., mutant alleles) at two different FAD3 loci, wherein one of the modified alleles includes a nucleic acid encoding a FAD3A polypeptide having a cysteine substituted for arginine at position 275, and wherein one of the modified alleles includes a fad3B nucleic acid sequence having a mutation in an exon-intron splice site recognition sequence.

In another aspect, this document features *Brassica* plants (e.g., *Brassica napus, Brassica juncea*, or *Brassica rapa* plants) and progeny thereof (e.g., seeds) that include modified alleles at two or more different FATB loci (e.g., 3 or 4 different FATB loci), wherein each modified allele results in production of a FATB polypeptide having reduced thioesterase activity relative to a corresponding wild-type FATB polypeptide, and further includes a modified allele at a FAD2 locus, wherein the modified allele includes a nucleic acid encoding a FAD2 polypeptide having a lysine substituted for glutamic acid in a HECGH motif. The plant further can include a modified allele at a different FAD2 locus, the modified allele including a nucleic acid encoding a FAD2 polypeptide having a glutamic acid substituted for glycine in a DRDYGILNKV motif or a histidine substituted for leucine in a KYLNNP motif. The FATB modified allele can include a nucleic acid encoding a truncated FATB polypeptide. The nucleic acid encoding the truncated FATB polypeptide can include a nucleotide sequence selected from the group consisting of: SEQ ID NO:1, SEQ ID NO:2, SEQ ID NO:3, and SEQ ID NO:4. For example, the plant can contain nucleic acids having the nucleotide sequences set forth in SEQ ID NO:1, SEQ ID NO:2, SEQ ID NO:3, and SEQ ID NO:4. The plant can be an $F_1$ hybrid. Any of the modified alleles can be a mutant allele.

In another aspect, this document features a method of producing an oil. The method includes crushing seeds produced from at least one *Brassica* plant described herein; and extracting the oil from the crushed seeds, the oil having, after refining, bleaching, and deodorizing, a total saturates content of about 2.5 to 5.5%. The oil further can include an eicosenoic acid content of about 1.6 to 2.3%. The oil further can include an oleic acid content of about 78 to 80%, a linoleic acid content of about 8 to 10%, and an α-linolenic acid content of about 2 to 4%.

This document also features a method for making a *Brassica* plant. The method includes crossing one or more first *Brassica* parent plants that contain a modified allele (e.g., mutant allele) at a FATB locus and one or more second *Brassica* parent plants that contain a modified allele (e.g., mutant allele) at a different FATB locus, wherein each modified allele results in the production of a FATB polypeptide having reduced thioesterase activity relative to a corresponding wild-type FATB polypeptide; and selecting, for one to five generations, for progeny plants having modified alleles at two or more different FATB loci thereby obtaining the *Brassica* plant.

In another aspect, this document features a method for making a *Brassica* plant. The method includes obtaining one or more first *Brassica* parent plants that contain modified alleles (e.g., mutant alleles) at two or more different FATB loci (e.g., three or four different FATB loci), wherein each modified allele results in the production of a FATB polypeptide having reduced thioesterase activity relative to a corresponding wild-type FATB polypeptide; obtaining one or more second *Brassica* parent plants containing a modified allele at a FAD2 locus, the modified allele including a nucleic acid encoding a FAD2 polypeptide having a lysine substituted for glycine in a HECGH motif; crossing the one or more first *Brassica* parent plants and the one or more second *Brassica* parent plants; and selecting, for one to five generations, for progeny plants having modified alleles at two or more different FATB loci and a modified allele at the FAD2 locus thereby obtaining the *Brassica* plant. Any of the modified alleles can be a mutant allele.

The document also features a method for making a *Brassica* plant. The method includes obtaining one or more first *Brassica* parent plants that contain modified alleles (e.g., mutant alleles) at two or more different FATB loci (e.g., three or four different FATB loci), wherein each modified allele results in the production of a FATB polypeptide having reduced thioesterase activity relative to a corresponding wild-type FATB polypeptide; obtaining one or more second *Brassica* parent plants containing a modified allele (e.g., mutant allele) at a FATA2 locus (e.g., FATA2b locus), the modified allele including a nucleic acid encoding a FATA2 polypeptide having a mutation in a region (SEQ ID NO:29) corresponding to amino acids 242 to 277 of the *Arabidopsis* FATA2 polypeptide; crossing said one or more first *Brassica* parent plants and said one or more second *Brassica* parent plants; and selecting, for one to five generations, for progeny plants having modified (e.g., mutant) alleles at two or more different FATB loci and a modified (e.g., mutant) allele at the FADA2 locus thereby obtaining the *Brassica* plant. The first *Brassica* parent plant further can contain a mutant allele at a FAD2 locus and mutant alleles at two different FAD3 loci, the FAD2 mutant allele including a nucleic acid encoding a FAD2 polypeptide having a lysine substituted for glutamic acid in a HECGH motif, wherein one of the FAD3 mutant alleles contains a nucleic acid encoding a FAD3A polypeptide having a cysteine substituted for arginine at position 275, and wherein one of the FAD3 mutant alleles contains a fad3B nucleic acid sequence having a mutation in an exon-intron splice site recognition sequence.

In yet another aspect, this document features a canola oil having an oleic acid content of about 78 to 80%, a linoleic acid content of about 8 to 10%, an α-linolenic acid content of no more than about 4%, and an eicosenoic acid content of about 1.6 to 2.3%. The palmitic acid content can be about 1.5 to 3.5%. The stearic acid content can be about 0.5% to 2.5%. The eicosenoic acid content can be about 1.9 to 2.2%. The α-linolenic acid content can be about 2 to about 4%.

This document also features seeds of a *Brassica* plant that include a modified allele (e.g., mutant allele) at a FATA2 locus, the modified allele (e.g., mutant allele) contains a nucleic acid encoding a FATA2 polypeptide having a mutation in a region (SEQ ID NO:29) corresponding to amino acids 242 to 277 of the polypeptide, the seeds yielding an oil having an oleic acid content of 78 to 80%, a linoleic acid content of about 8 to 10%, an α-linolenic acid content of no more than about 4%, and an eicosenoic acid content of 1.6 to 2.3%. The seeds can be $F_2$ seeds. The *Brassica* plant further can include modified (e.g., mutant) alleles at four different FATB loci and/or a modified (e.g., mutant) allele at a FAD2 locus and modified (e.g., mutant) alleles at two different FAD3 loci, the FAD2 modified (e.g., mutant) allele can include a nucleic acid encoding a FAD2 polypeptide having a lysine substituted for glutamic acid in a HECGH motif, one of the FAD3 modified (e.g., mutant) alleles can include a nucleic acid encoding a FAD3A polypeptide having a cysteine substituted for arginine at position 275, and one of the FAD3 modified (e.g., mutant) alleles can include a fad3B nucleic acid sequence having a mutation in an exon-intron splice site recognition sequence.

This document also features a canola oil having a total saturated fatty acid content of no more than about 3.7% and an oleic acid content of about 72 to 75%. The oil can have a palmitic acid content of about 2.2 to 2.4%. The oil can have a stearic acid content of about 0.5 to 0.8%. The oil can have an eicosenoic acid content of about 1.6 to 1.9%. The total saturated fatty acid content can be about 3.4 to 3.7%.

In yet another aspect, this document features a plant cell of a plant described herein, wherein the plant cell includes one or more of the modified (e.g., mutant) alleles.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is an alignment of the nucleotide sequences of the *Brassica rapa* FatA1 ("Brapa FatA1," SEQ ID NO:33; Genbank Accession No. U17098), *Arabidopsis thaliana* FatA1 ("AtFatA1," SEQ ID NO:34; At3g25110; Genbank Accession No. NM_113415), *B. napus* FatA1 from 15.24 ("BnFatA1 1524," SEQ ID NO:35), *B. napus* FatA2 from 15.24 ("BnFatA2 1524," SEQ ID NO:39), *A. thaliana* FatA2 ("AtFatA2," SEQ ID NO:36; At4g13050; Genbank Accession No. NM_117374), and *B. napus* pNL2 ("Bnapus pNL2," SEQ ID NO:37; (Genbank Accession No. X73849). The black boxes indicate sequence differences compared to the consensus sequence developed from the alignment; the position marked '1' highlights the SNP unique to 15.24 in the *B. napus* FatA2b isoform and shows the C to T mutation (Pro to Leu) of 15.24. The position marked as '2', highlights a SNP which distinguishes the *B. napus* FatA2a and *B. napus* FatA2b isoforms from each other (see FIG. 4).

FIG. 2 is an alignment of a portion of the FatA2 nucleotide sequences from *Arabidopsis thaliana* ("AtFatA2," SEQ ID NO:41), 15.24 ("15.24FatA2 (1)," SEQ ID NO:40; "15.24FatA2 (2)," SEQ ID NO:38), and the 01OB240 parent ("OB240FatA2 (1)," SEQ ID NO:42; "OB240FatA2 (2)," SEQ ID NO:43). At the position labeled "1," the "C" to "T" SNP is unique to BnFatA2b sequence in 15.24 germplasm (labeled 15.24FatA2(1)). At the position labeled "2", the isoform differences between *B. napus* FatA2a and *B. napus*FatA2b are apparent (15.24FatA2(2) and OB240FatA2 (1) are *B. napus* FatA2a isoforms, while 15.24FatA2(1) and OB240FatA2(2) are *B. napus* FatA2b isoforms). Differences in sequence are highlighted in black.

FIG. 3 is an alignment of the amino acid sequence of residues 242 to 277 of the *A. thaliana* FatA2 ("AtFatA2," SEQ ID NO:48; GenBank Accession No. NP_193041.1) with the *B. napus* FatA2 from 15.24 ("15.24FatA2(1)," SEQ ID NO:49; "15.24FatA2 (2)," SEQ ID NO:50) and 01OB240 ("OB240FatA2 (1)," SEQ ID NO:51; "OB240FatA2 (2)," SEQ ID NO:52). The FatA2 SNP in position "1" (C to T mutation) in 15.24 causes a Pro to Leu change, while the isoform difference at position "2" does not result in an amino acid change in isoforms BnFatA2a and BnFatA2b.

FIG. 4 is an alignment of the BnFatA2a and BnFatA2b sequences from the 01OB240 (SEQ ID NOs:44 and 45, respectively) and 15.24 germplasm (SEQ ID NOs:46 and 47, respectively). Position "1" refers to the "C" to "T" SNP unique to 15.24 in the BnFatA2b sequences that correlate with the low saturate phenotype. See also FIGS. 1-3. Position "2" refers to the "2" positions in FIGS. 1, 2, and 3, and highlights a difference in sequence between the BnFatA2a and BnFatA2b isoforms. Black boxes represent mismatches compared to the 01OB240 BnFatA2b.

Like reference symbols in the various drawings indicate like elements.

DETAILED DESCRIPTION

In general, this document provides *Brassica* plants, including *B. napus, B. juncea*, and *B. rapa* species of *Brassica*, that yield seeds producing oils having a low total saturated fatty acid content (i.e., 6% or less) or having very low saturates (i.e., having 3.6% or less). As used herein, total saturated fatty acid content refers to the total of myristic acid (C14:0), palmitic acid (C16:0), stearic acid (C18:0), arachidic acid (C20:0), behenic acid (C22:0), and lignoceric acid (C24:0). For example, *Brassica* plants described herein can produce oils having a total saturated fatty acid content of about 2.5 to 5.5%, 3 to 5%, 3 to 4.5%, 3.25 to 3.75%, 3.0 to 3.5%, 3.6 to 5%, 4 to 5.5%, or 4 to 5%. Oils having a low or no total saturated fatty acid content have improved nutritional quality and can help consumers reduce their intake of saturated fatty acids.

As described herein, *Brassica* plants can be made that yield seed oils having a low total saturated fatty acid content in combination with a typical (60%-70%), mid (71%-80%), or high (>80%) oleic acid content. Such *Brassica* plants can produce seed oils having a fatty acid content tailored to the desired end use of the oil (e.g., frying or food applications). For example, *Brassica* plants can be produced that yield seeds having a low total saturated fatty acid content, an oleic acid content of 60% to 70%, and an α-linolenic acid content of 2% to 5%. Total polyunsaturates (i.e., total of linoleic acid and α-linolenic acid) in such seeds typically is <35%. Canola oils having such fatty acid contents are particularly useful for frying applications due to the polyunsaturated content, which is low enough to have improved oxidative stability for frying yet high enough to impart the desired fried flavor to the food being fried, and are an improvement over commodity type canola oils. The fatty acid content of commodity type canola oils typically is about 6-8% total saturated fatty acids, 55 to 65% oleic acid, about 22 to 30% linoleic acid, and about 7-10% α-linolenic acid.

*Brassica* plants also can be produced that yield seeds having a low total saturated fatty acid content, mid oleic acid content (e.g., 71% to 80% oleic acid) and a low α-linolenic acid content (e.g., 2% to 5.0%). Canola oils having such fatty acid contents have an oxidative stability that is higher than oils with a lower oleic acid content or commodity type canola oils, and are useful for coating applications (e.g., spray-coatings), formulating food products, or other applications where shelf-life stability is desired. In addition, *Brassica* plants can be produced that yield seeds having a low total saturated fatty acid content, high oleic acid content (e.g., 81% to 90% oleic acid) and an α-linolenic acid content of 2 to 5%. Canola oils having a low total saturated fatty acid content, high oleic acid, and low α-linolenic acid content are particularly useful for food applications requiring high oxidative stability and a reduced saturated fatty acid content.

*Brassica* Plants

*Brassica* plants described herein have low levels of total saturated fatty acids in the seed oil as a result of reduced activity of fatty acyl-ACP thioesterase A2 (FATA2) and/or reduced activity of fatty acyl-ACP thioesterase B (FATB). It is understood that throughout the disclosure, reference to "plant" or "plants" includes progeny, i.e., descendants of a particular plant or plant line, as well as cells or tissues from the plant. Progeny of an instant plant include seeds formed on $F_1$, $F_2$, $F_3$, $F_4$ and subsequent generation plants, or seeds formed on $BC_1$, $BC_2$, $BC_3$, and subsequent generation plants. Seeds produced by a plant can be grown and then selfed (or outcrossed and selfed, or doubled through dihaploid) to obtain seeds homozygous for a mutant allele. The term "allele" or "alleles" refers to one or more alternative forms of a gene at a particular locus. As used herein, a "line" is a group of plants that display little or no genetic variation between individuals for at least one trait. Such lines may be created by several generations of self-pollination and selection, or vegetative propagation from a single parent using tissue or cell culture techniques. As used herein, the term "variety" refers to a line which is used for commercial production, and includes hybrid varieties and open-pollinated varieties.

Fatty acyl-ACP thioesterases hydrolyze acyl-ACPs in the chloroplast to release the newly synthesized fatty acid from ACP, effectively removing it from further chain elongation in the plastid. The free fatty acid can then leave the plastid, become bound to CoenzymeA (CoA) and enter the Kennedy pathway in the endoplasmic reticulum (ER) for triacylglycerol (TAG) biosynthesis. Members of the FATA family prefer oleoyl (C18:1) ACP substrates with minor activity towards 18:0 and 16:0-ACPs, while members of the FATB family hydrolyze primarily saturated acyl-ACPs between 8 and 18 carbons in length. See Jones et al., *Plant Cell* 7:359-371 (1995); Ginalski and Rhchlewski, *Nucleic Acids Res* 31:3291-3292 (2003); and Voelker T in Genetic Engineering (Setlow, J K, ed) Vol 18, 111-133, Plenum Publishing Corp., New York (2003).

Reduced activity, including absence of detectable activity, of FATA2 or FATB can be achieved by modifying an endogenous fatA2 or fatB allele. An endogenous fatA2 or fat3B allele can be modified by, for example, mutagenesis or by using homologous recombination to replace an endogenous plant gene with a variant containing one or more mutations (e.g., produced using site-directed mutagenesis). See, e.g., Townsend et al., *Nature* 459:442-445 (2009); Tovkach et al., *Plant J.*, 57:747-757 (2009); and Lloyd et al., *Proc. Natl. Acad. Sci. USA*, 102:2232-2237 (2005). Similarly, for other genes discussed herein, the endogenous allele can be modified by mutagenesis or by using homologous recombination to replace an endogenous gene with a variant. Modified alleles obtained through mutagenesis are referred to as mutant alleles herein.

Reduced activity, including absence of detectable activity, can be inferred from the decreased level of saturated fatty acids in the seed oil compared with seed oil from a corresponding control plant. Reduced activity also can be assessed in plant extracts using assays for fatty acyl-ACP hydrolysis. See, for example, Bonaventure et al., *Plant Cell* 15:1020-1033 (2003); and Eccleston and Ohlrogge, *Plant Cell* 10:613-622 (1998).

Genetic mutations can be introduced within a population of seeds or regenerable plant tissue using one or more mutagenic agents. Suitable mutagenic agents include, for example, ethyl methane sulfonate (EMS), methyl N-nitrosoguanidine (MNNG), ethidium bromide, diepoxybutane, ionizing radiation, x-rays, UV rays and other mutagens known in the art. In some embodiments, a combination of mutagens, such as EMS and MNNG, can be used to induce mutagenesis. The treated population, or a subsequent generation of that population, can be screened for reduced thioesterase activity that results from the mutation, e.g., by determining the fatty acid profile of the population and comparing it to a corresponding non-mutagenized population. Mutations can be in any portion of a gene, including coding sequence, intron sequence and regulatory elements, that render the resulting gene product non-functional or with reduced activity. Suitable types of mutations include, for example, insertions or deletions of nucleotides, and transitions or transversions in the wild-type coding sequence. Such mutations can lead to deletion or insertion of amino acids, and conservative or non-conservative amino acid substitutions in the corresponding gene product. In some embodiments, the mutation is a nonsense mutation, which results in the introduction of a stop codon (TGA, TAA, or TAG) and production of a truncated polypeptide. In some embodiments, the mutation is a splice site mutation which alters or abolishes the correct splicing of the pre-mRNA sequence, resulting in a protein of different amino acid sequence than the wild type. For example, one or more exons may be skipped during RNA splicing, resulting in a protein lacking the amino acids encoded by the skipped exons. Alternatively, the reading frame may be altered by incorrect splicing, one or more introns may be retained, alternate splice donors or acceptors may be generated, or splicing may be initiated at an alternate position, or alternative poly-adenylation signals may be generated. In some embodiments, more than one mutation or more than one type of mutation is introduced.

Insertions, deletions, or substitutions of amino acids in a coding sequence may, for example, disrupt the conformation of essential alpha-helical or beta-pleated sheet regions of the resulting gene product. Amino acid insertions, deletions, or substitutions also can disrupt binding, alter substrate specificity, or disrupt catalytic sites important for gene product activity. It is known in the art that the insertion or deletion of a larger number of contiguous amino acids is more likely to render the gene product non-functional, compared to a smaller number of inserted or deleted amino acids. Non-conservative amino acid substitutions may replace an amino acid of one class with an amino acid of a different class. Non-conservative substitutions may make a substantial change in the charge or hydrophobicity of the gene product. Non-conservative amino acid substitutions may also make a substantial change in the bulk of the residue side chain, e.g., substituting an alanine residue for an isoleucine residue.

Examples of non-conservative substitutions include the substitution of a basic amino acid for a non-polar amino acid, or a polar amino acid for an acidic amino acid. Because there are only 20 amino acids encoded in a gene, substitutions that result in reduced activity may be determined by routine experimentation, incorporating amino acids of a different class in the region of the gene product targeted for mutation.

In some embodiments, a *Brassica* plant contains a mutant allele at a FATA2 locus, wherein the mutant allele results in the production of a FATA2 polypeptide having reduced thioesterase activity relative to a corresponding wild-type FATA2 polypeptide. For example, the mutant allele can include a nucleic acid that encodes a FATA2 polypeptide having a non-conservative substitution within a helix/4-stranded sheet (4HBT) domain (also referred to as a hot-dog domain) or non-conservative substitution of a residue affecting catalytic activity or substrate specificity. For example, a Brassica plant can contain a mutant allele that includes a nucleic acid encoding a FATA2b polypeptide having a substitution in a region (SEQ ID NO:29) of the polypeptide corresponding to residues 242 to 277 of the FATA2 polypeptide (as numbered based on the alignment to the *Arabidopsis thaliana* FATA2 polypeptide set forth in GenBank Accession No. NP_193041.1, protein (SEQ ID NO:30); GenBank Accession No. NM_117374, mRNA). This region of FATA2 is highly conserved in *Arabidopsis* and *Brassica*. In addition, many residues in this region are conserved between FATA and FATB, including the aspartic acid at position 259, asparagine at position 263, histidine at position 265, valine at position 266, asparagine at position 268, and tyrosine at position 271 (as numbered based on the alignment to SEQ ID NO:30). See also FIG. 3. The asparagine at position 263 and histidine at position 265 are part of the catalytic triad, and the arginine at position 256 is involved in determining substrate specificity. See also Mayer and Shanklin, *BMC Plant Biology* 7:1-11 (2007). SEQ ID NO:31 sets forth the predicted amino acid sequence of the *Brassica* FATA2b polypeptide encoded by exons 2-6, and corresponding to residues 121 to 343 of the *A.*

*thaliana* sequence set forth in SEQ ID NO:30. For example, the FATA2 polypeptide can have a substitution of a leucine residue for proline at the position corresponding to position 255 of the *Arabidopsis* FATA2 polypeptide (i.e., position 14 of SEQ ID NO:29 or position 135 of SEQ ID NO:31). The proline in the *B. napus* sequence corresponding to position 255 in *Arabidopsis* is conserved among *B. napus, B. rapa, B. juncea, Zea mays, Sorghum bicolor, Oryza sativa Indica* (rice), *Triticum aestivum, Glycine max, Jatropha* (tree species), *Carthamus tinctorius, Cuphea hookeriana, Iris tectorum, Perilla frutescens, Helianthus annuus, Garcinia mangostana, Picea sitchensis, Physcomitrella patens* subsp. *Patens, Elaeis guineensis, Vitis vinifera, Elaeis oleifera, Camellia oleifera, Arachis hypogaea, Capsicum annuum, Cuphea hookeriana, Populus trichocarpa,* and *Diploknema butyracea.* As described in Example 2, the mutation at position 255 is associated with a low total saturated fatty acid phenotype, low stearic acid phenotype, low arachidic acid phenotype, and an increased eicosenoic acid phenotype. The stearic acid content phenotype is negatively correlated with the eicosenoic acid phenotype.

In some embodiments, the mutant allele at a FATA2 locus includes a nucleotide sequence having at least 90% (e.g., at least 91, 92, 93, 94, 95, 96, 97, 98, or 99%) sequence identity to the nucleotide sequence set forth in SEQ ID NO:28 or SEQ ID NO:32. The nucleotide sequences set forth in SEQ ID NOs:28 and 32 are representative nucleotide sequences from the fatA2b gene from *B. napus* line 15.24. As used herein, the term "sequence identity" refers to the degree of similarity between any given nucleic acid sequence and a target nucleic acid sequence. The degree of similarity is represented as percent sequence identity. Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q −1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (i) a 500-base nucleic acid target sequence is compared to a subject nucleic acid sequence, (ii) the Bl2seq program presents 200 bases from the target sequence aligned with a region of the subject sequence where the first and last bases of that 200-base region are matches, and (iii) the number of matches over those 200 aligned bases is 180, then the 500-base nucleic acid target sequence contains a length of 200 and a sequence identity over that length of 90% (i.e., 180, 200×100=90).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

In some embodiments, a *Brassica* plant contains a mutant allele at a FATB locus, wherein the mutant allele results in the production of a FATB polypeptide having reduced thioesterase activity relative to a corresponding wild-type FATB polypeptide. In some embodiments, a *Brassica* plant contains mutant alleles at two or more different FATB loci. In some embodiments, a *Brassica* plant contains mutant alleles at three different FATB loci or contains mutant alleles at four different FATB loci. *Brassica napus* contains 6 different FATB isoforms (i.e., different forms of the FATB polypeptide at different loci), which are called isoforms 1-6 herein. SEQ ID NOs:18-21 and 26-27 set forth the nucleotide sequences encoding FATB isoforms 1-6, respectively, of *Brassica napus.* The nucleotide sequences set forth in SEQ ID NOs: 18-21 and 26-27 have 82% to 95% sequence identity as measured by the ClustalW algorithm.

For example, a *Brassica* plant can have a mutation in a nucleotide sequence encoding FATB isoform 1, isoform 2, isoform 3, isoform 4, isoform 5, or isoform 6. In some embodiments, a plant can have a mutation in a nucleotide sequence encoding isoforms 1 and 2; 1 and 3; 1 and 4; 1 and 5; 1 and 6; 2 and 3; 2 and 4; 2 and 5; 2 and 6; 3 and 4; 3 and 5; 3 and 6; 4 and 5; 4 and 6; 5 and 6; 1, 2, and 3; 1, 2, and 4; 1, 2, and 5; 1, 2, and 6; 2, 3, and 4; 2, 3, and 5; 2, 3, and 6; 3, 4, and 5; 3, 5, and 6; 4, 5, and 6; 1, 2, 3, and 4; 1, 2, 3, and 5; 1, 2, 3, and 6; 1, 2, 4, and 6; 1, 3, 4 and 5; 1, 3, 4, and 6; 1, 4, 5, and 6; 2, 3, 4, and 5; 2, 3, 4 and 6; or 3, 4, 5, and 6. In some embodiments, a *Brassica* plant can have a mutation in nucleotide sequences encoding FATB isoforms 1, 2, and 3; 1, 2, and 4; 2, 3, and 4; or 1, 2, 3, and 4. In some embodiments, a mutation results in deletion of a 4HBT domain or a portion thereof of a FATB polypeptide. FATB polypeptides typically contain a tandem repeat of the 4HBT domain, where the N-terminal 4HBT domain contains residues affecting substrate specificity (e.g., two conserved methionines, a conserved lysine, a conserved valine, and a conserved serine) and the C-terminal 4HBT domain contains residues affecting catalytic activity (e.g., a catalytic triad of a conserved asparagine, a conserved histidine, and a conserved cysteine) and substrate specificity (e.g., a conserved tryptophan). See Mayer and Shanklin, *J. Biol. Chem.* 280:3621-3627 (2005). In some embodiments, the mutation results in a non-conservative substitution of a residue in a 4HBT domain or a residue affecting substrate specificity. In some embodiments, the mutation is a splice site mutation. In some embodiment, the mutation is a nonsense mutation in which a premature stop codon (TGA, TAA, or TAG) is introduced, resulting in the production of a truncated polypeptide.

SEQ ID NOs:1-4 set forth the nucleotide sequences encoding isoforms 1-4, respectively, and containing exemplary nonsense mutations that result in truncated FATB polypeptides. SEQ ID NO:1 is the nucleotide sequence of isoform 1 having a mutation at position 154, which changes the codon from CAG to TAG. SEQ ID NO:2 is the nucleotide sequence of isoform 2 having a mutation at position 695, which changes the codon from CAG to TAG. SEQ ID NO:3 is the nucleotide sequence of isoform 3 having a mutation at position 276, which changes the codon from TGG to TGA. SEQ ID NO:4 is the nucleotide sequence of isoform 4 having a mutation at position 336, which changes the codon from TGG to TGA.

Two or more different mutant FATB alleles may be combined in a plant by making a genetic cross between mutant lines. For example, a plant having a mutant allele at a FATB locus encoding isoform 1 can be crossed or mated with a second plant having a mutant allele at a FATB locus encoding isoform 2. Seeds produced from the cross are planted and the resulting plants are selfed in order to obtain progeny seeds. These progeny seeds can be screened in order to identify those seeds carrying both mutant alleles. In some embodiments, progeny are selected over multiple generations (e.g., 2 to 5 generations) to obtain plants having mutant alleles at two different FATB loci. Similarly, a plant having mutant alleles at two or more different FATB isoforms can be crossed with a second plant having mutant alleles at two or more different FATB alleles, and progeny seeds can be screened to identify those seeds carrying mutant alleles at four or more different FATB loci. Again, progeny can be selected for multiple generations to obtain the desired plant.

In some embodiments, a mutant allele at a FATA2 locus and mutant alleles at two or more (e.g., three or four) different FATB loci can be combined in a plant. For example, a plant having a mutant allele at a FATA2 locus can be crossed or mated with a second plant having mutant alleles at two or more different FATB loci. Seeds produced from the cross are planted and the resulting plants are selfed in order to obtain progeny seeds. These progeny seeds can be screened in order to identify those seeds carrying mutant FATA2 and FATB alleles. Progeny can be selected over multiple generations (e.g., 2 to 5 generations) to obtain plants having a mutant allele at a FATA2 locus and mutant alleles at two or more different FATB loci. As described herein, plants having a mutant allele at a FATA2b locus and mutant alleles at three or four different FATB loci have a low total saturated fatty acid content that is stable over different growing conditions, i.e., is less subject to variation due to warmer or colder temperatures during the growing season. Due to the differing substrate profiles of the FatB and FatA enzymes with respect to 16:0 and 18:0, respectively, plants having mutations in FatA2 and FatB loci exhibit a substantial reduction in amounts of both 16:0 and 18:0 in seed oil.

*Brassica* plants having mutant alleles at FATA2 and/or FATB loci also can include mutant alleles at loci controlling fatty acid destaurase activity such that the oleic acid and linolenic acid levels can be tailored to the end use of the oil. For example, such *Brassica* plants also can exhibit reduced activity of delta-15 desaturase (also known as FAD3), which is involved in the enzymatic conversion of linoleic acid to α-linolenic acid. The gene encoding delta-15 fatty acid desaturase is referred to as fad3 in *Brassica* and *Arabidopsis*. Sequences of higher plant fad3 genes are disclosed in Yadav et al., *Plant Physiol.*, 103:467-476 (1993), WO 93/11245, and Arondel et al., *Science*, 258:1353-1355 (1992). Decreased activity, including absence of detectable activity, of delta-15 desaturase can be achieved by mutagenesis. Decreased activity, including absence of detectable activity, can be inferred from the decreased level of linolenic acid (product) and in some cases, increased level of linoleic acid (the substrate) in the plant compared with a corresponding control plant. For example, parent plants can contain the mutation from the APOLLO or STELLAR *B. napus* variety that confers low linolenic acid. The STELLAR and APOLLO varieties were developed at the University of Manitoba (Manitoba, Canada). In some embodiments, the parents contain the fad3A and/or fad3B mutation from IMC02 that confer a low linolenic acid phenotype. IMC02 contains a mutation in both the fad3A and fad3B genes. The fad3A gene contains a C to T mutation at position 2565, numbered from the ATG in genomic DNA, resulting in the substitution of a cysteine for arginine at position 275 of the encoded FAD3A polypeptide. The fad3B gene contains a G to A mutation at position 3053 from ATG in genomic DNA, located in the exon-intron splice site recognition sequence. IMC02 was obtained from a cross of IMC01×Westar. See Example 3 of U.S. Pat. No. 5,750,827. IMC01 was deposited with the American Type Culture Collection (ATCC) under Accession No. 40579. IMC02 was deposited with the ATCC under Accession No. PTA-6221.

In some embodiments, a *Brassica* plant contains a mutant allele at a FATA2 locus and a mutant allele at a FAD3 locus. For example, a *Brassica* plant can contain a mutant allele at a FATA2 locus and a mutant allele at a FAD3 locus that contains a nucleic acid encoding a FAD3 polypeptide with a cysteine substituted for arginine at position 275 and/or a nucleic acid having a mutation in an exon-intron splice site recognition sequence. A *Brassica* plant also can contain mutant alleles at two or more different FATB loci (three or four different loci) and a FAD3 locus that contains a nucleic acid encoding a FAD3 polypeptide with a cysteine substituted for arginine at position 275 and/or a nucleic acid having a mutation in an exon-intron splice site recognition sequence. A *Brassica* plant also contain a mutant allele at a FATA2 locus, mutant alleles at two or more different FATB loci (three or four different loci) and a FAD3 locus that contains a nucleic acid encoding a FAD3 polypeptide with a cysteine substituted for arginine at position 275 and/or a nucleic acid having a mutation in an exon-intron splice site recognition sequence.

*Brassica* plants also can have decreased activity of a delta-12 desaturase, which is involved in the enzymatic conversion of oleic acid to linoleic acid, to confer a mid or high oleic acid content in the seed oil. *Brassica* plants can exhibit reduced activity of delta-12 desaturase (also known as FAD2) in combination with reduced activity of FATA2 and/or FATB. The sequences for the wild-type fad2 genes from *B. napus* (termed the D form and the F form) are disclosed in WO 98/56239. A reduction in delta-12 desaturase activity, including absence of detectable activity, can be achieved by mutagenesis. Decreased delta-12 desaturase activity can be inferred from the decrease level of linoleic acid (product) and increased level of oleic acid (substrate) in the plant compared with a corresponding control plant. Non-limiting examples of suitable fad2 mutations include the G to A mutation at nucleotide 316 within the fad2-D gene, which results in the substitution of a lysine residue for glutamic acid in a HECGH (SEQ ID NO:5) motif. Such a mutation is found within the variety IMC129, which has been deposited with the ATCC under Accession No. 40811. Another suitable fad2 mutation can be the T to A mutation at nucleotide 515 of the fad2-F gene, which results in the substitution of a histidine residue for leucine in a KYLNNP (SEQ ID NO:6) motif (amino acid 172 of the Fad2 F polypeptide). Such a mutation is found within the variety Q508. See U.S. Pat. No. 6,342,658. Another example of a fad2 mutation is the G to A mutation at nucleotide 908 of the fad2-F gene, which results in the substitution of a glutamic acid for glycine in the DRDYGILNKV (SEQ ID NO:7) motif (amino acid 303 of the Fad2 F polypeptide). Such a mutation is found within the variety Q4275, which has been deposited with the ATCC under Accession No. 97569. See U.S. Pat. No. 6,342,658. Another example of a suitable fad2 mutation can be the C to T mutation at nucleotide 1001 of the fad2-F gene (as numbered from the ATG), which results in the substitution of an isoleucine for threonine (amino acid 334 of the Fad2 F polypeptide). Such a mutation is found within the high oleic acid variety Q7415.

Typically, the presence of one of the fad2-D or fad2-F mutations confers a mid-oleic acid phenotype (e.g., 70-80% oleic acid) to the seed oil, while the presence of both fad2-D and fad2-F mutations confers a higher oleic acid phenotype (e.g., >80% oleic acid). For example, Q4275 contains the fad2-D mutation from IMC129 and a fad2-F mutation at amino acid 303. Q508 contains fad2-D mutation from IMC129 and a fad2-F mutation at amino acid 172. Q7415 contains the fad2-D mutation from IMC129 and a fad2-F mutation at amino acid 334. The presence of both fad2 mutations in Q4275, Q508, and Q7415 confers a high oleic acid phenotype of greater than 80% oleic acid.

Thus, in some embodiments, a Brassica plant contains a mutant allele at a FATA2 locus (e.g., FATA2b locus) and a mutant allele at a FAD2 locus. For example, a Brassica plant can contain a mutant allele at a FATA2 locus and a mutant allele at a FAD2 locus described above. A Brassica plant also can contain mutant alleles at two or more different FATB loci (three or four different loci) and a FAD2 locus described above. A Brassica plant can also contain a mutant allele at a FATA2 locus, mutant alleles at two or more different FATB loci (three or four different loci) and a mutant allele at a FAD2 locus described above. In some embodiments, a Brassica plant contains a mutant allele at a FATA2 locus, a mutant allele at a FAD2 locus, and a mutant allele at a FAD3 locus described above. A Brassica plant also can contain mutant alleles at two or more different FATB loci (three or four different loci), mutant alleles at FAD2 loci, and mutant alleles at FAD3 loci described above. A Brassica plant also contain a mutant allele at a FATA2 locus, mutant alleles at two or more different FATB loci (three or four different loci), mutant alleles at FAD2 loci, and mutant alleles at FAD3 loci described above.

Production of Hybrid Brassica Varieties

Hybrid Brassica varieties can be produced by preventing self-pollination of female parent plants (i.e., seed parents), permitting pollen from male parent plants to fertilize such female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be cytoplasmic male sterility (CMS), nuclear male sterility, molecular male sterility wherein a transgene inhibits microsporogenesis and/or pollen formation, or be produced by self-incompatibility. Female parent plants containing CMS are particularly useful. CMS can be, for example of the ogu (Ogura), nap, pol, tour, or mur type. See, for example, Pellan-Delourme and Renard, 1987, Proc. $7^{th}$ Int. Rapeseed Conf., Poznan, Poland, p. 199-203 and Pellan-Delourme and Renard, 1988, Genome 30:234-238, for a description of Ogura type CMS. See, Riungu and McVetty, 2003, Can. J. Plant Sci., 83:261-269 for a description of nap, pol, tour, and mur type CMS.

In embodiments in which the female parent plants are CMS, the male parent plants typically contain a fertility restorer gene to ensure that the $F_1$ hybrids are fertile. For example, when the female parent contains an Ogura type CMS, a male parent is used that contains a fertility restorer gene that can overcome the Ogura type CMS. Non-limiting examples of such fertility restorer genes include the Kosena type fertility restorer gene (U.S. Pat. No. 5,644,066) and Ogura fertility restorer genes (U.S. Pat. Nos. 6,229,072 and 6,392,127). In other embodiments in which the female parents are CMS, male parents can be used that do not contain a fertility restorer. $F_1$ hybrids produced from such parents are male sterile. Male sterile hybrid seed can be inter-planted with male fertile seed to provide pollen for seed-set on the resulting male sterile plants.

The methods described herein can be used to form single-cross Brassica $F_1$ hybrids. In such embodiments, the parent plants can be grown as substantially homogeneous adjoining populations to facilitate natural cross-pollination from the male parent plants to the female parent plants. The $F_1$ seed formed on the female parent plants is selectively harvested by conventional means. One also can grow the two parent plants in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent that satisfies the fatty acid parameters for the female parent of the first cross. Here, assuming a bulk planting, the overall oleic acid content of the vegetable oil may be reduced over that of a single-cross hybrid; however, the seed yield will be further enhanced in view of the good agronomic performance of both parents when making the second cross. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Hybrids described herein have good agronomic properties and exhibit hybrid vigor, which results in seed yields that exceed that of either parent used in the formation of the $F_1$ hybrid. For example, yield can be at least 10% (e.g., 10% to 20%, 10% to 15%, 15% to 20%, or 25% to 35%) above that of either one or both parents. In some embodiments, the yield exceeds that of open-pollinated spring canola varieties such as 46A65 (Pioneer) or Q2 (University of Alberta), when grown under similar growing conditions. For example, yield can be at least 10% (e.g., 10% to 15% or 15% to 20%) above that of an open-pollinated variety.

Hybrids described herein typically produce seeds having very low levels of glucosinolates (<30 μmol/gram of de-fatted meal at a moisture content of 8.5%). In particular, hybrids can produce seeds having <20 μmol of glucosinolates/gram of de-fatted meal. As such, hybrids can incorporate mutations that confer low glucosinolate levels. See, for example, U.S.

Pat. No. 5,866,762. Glucosinolate levels can be determined in accordance with known techniques, including high performance liquid chromatography (HPLC), as described in ISO 9167-1:1992(E), for quantification of total, intact glucosinolates, and gas-liquid chromatography for quantification of trimethylsilyl (TMS) derivatives of extracted and purified desulfoglucosinolates. Both the HPLC and TMS methods for determining glucosinolate levels analyze de-fatted or oil-free meal.

Canola Oil

*Brassica* plants disclosed herein are useful for producing canola oils with low or no total saturated fatty acids. For example, oil obtained from seeds of *Brassica* plants described herein may have a total saturated fatty acid content of about 2.5 to 5.5%, 3 to 5%, 3 to 4.5%, 3.25 to 3.75%, 3.0 to 3.5%, 3.4 to 3.7%, 3.6 to 5%, 4 to 5.5%, 4 to 5%, or 4.25 to 5.25%. In some embodiments, an oil has a total saturated fatty acid content of about 4 to about 5.5%, an oleic acid content of about 60 to 70% (e.g., 62 to 68%, 63 to 67%, or 65 to 66%), and an α-linolenic acid content of about 2.5 to 5%. In some embodiments, an oil has a total saturated fatty acid content of about 2.5 to 5.5% (e.g., 4 to 5%), an oleic acid content of about 71 to 80% (e.g., 72 to 78%, 73 to 75%, 74 to 78%, or 75 to 80%) and an α-linolenic acid content of about 2 to 5.0% (e.g., 2.0 to 2.8%, 2.25 to 3%, 2.5 to 3%, 3 to 3.5%, 3.25% to 3.75%, 3.5 to 4%, 3.75 to 4.25%, 4 to 4.5%, 4.25 to 4.75%, 4.5 to 5%). In some embodiments, a canola oil can have a total saturated fatty acid content of 2.5 to 5.5%, an oleic acid content of 78 to 80%, and an α-linolenic acid content of no more than 4% (e.g., 2 to 4%). In some embodiments, an oil has a total saturated fatty acid content of about 3.5 to 5.5% (e.g., 4 to 5%), an oleic acid content of about 81 to 90% (e.g., 82 to 88% or 83 to 87% oleic acid) and an α-linolenic acid content of 2 to 5% (e.g., 2 to 3% or 3 to 5%). In some embodiments, an oil has a total saturated fatty acid content of no more than 3.7% (e.g., about 3.4 to 3.7% or 3.4 to 3.6%) and an oleic acid content of about 72 to 75%.

Low saturate oils described herein can have a palmitic acid content of about 1.5 to 3.5% (e.g., 2 to 3% or 2.2 to 2.4%). The stearic acid content of such oils can be about 0.5 to 2.5% (e.g., 0.5 to 0.8%, 1 to 2%, or 1.5 to 2.5%).

Oils described herein can have an eicosenoic acid content greater than 1.6%, e.g., 1.6 to 1.9%, 1.7 to 2.3%, 1.8 to 2.3%, or 1.9 to 2.3%, in addition to a low total saturates content.

Oils described herein can have a linoleic acid content of about 3 to 20%, e.g., 3.4 to 5%, 3.75 to 5%, 8 to 10%, 10 to 12%, 11 to 13%, 13 to 16%, or 14 to 18%, in addition to a low total saturates content.

Oils described herein have an erucic acid content of less than 2% (e.g., less than 1%, 0.5%, 0.2, or 0.1%) in additions to a low total saturates content.

The fatty acid composition of seeds can be determined by first crushing and extracting oil from seed samples (e.g., bulk seeds samples of 10 or more seeds). TAGs in the seed are hydrolyzed to produce free fatty acids, which then can be converted to fatty acid methyl esters and analyzed using techniques known to the skilled artisan, e.g., gas-liquid chromatography (GLC) according to AOCS Procedure Ce 1e-91. Near infrared (NIR) analysis can be performed on whole seed according to AOCS Procedure Am-192 (revised 1999)

Seeds harvested from plants described herein can be used to make a crude canola oil or a refined, bleached, and deodorized (RBD) canola oil with a low or no total saturated fatty acid content. Harvested canola seed can be crushed by techniques known in the art. The seed can be tempered by spraying the seed with water to raise the moisture to, for example, 8.5%. The tempered seed can be flaked using smooth roller with, for example, a gap setting of 0.23 to 0.27 mm. Heat may be applied to the flakes to deactivate enzymes, facilitate further cell rupturing, coalesce the oil droplets, or agglomerate protein particles in order to ease the extraction process. Typically, oil is removed from the heated canola flakes by a screw press to press out a major fraction of the oil from the flakes. The resulting press cake contains some residual oil.

Crude oil produced from the pressing operation typically is passed through a settling tank with a slotted wire drainage top to remove the solids expressed out with the oil in the screw pressing operation. The clarified oil can be passed through a plate and frame filter to remove the remaining fine solid particles. Canola press cake produced from the screw pressing operation can be extracted with commercial n-Hexane. The canola oil recovered from the extraction process is combined with the clarified oil from the screw pressing operation, resulting in a blended crude oil.

Free fatty acids and gums typically are removed from the crude oil by heating in a batch refining tank to which food grade phosphoric acid has been added. The acid serves to convert the non-hydratable phosphatides to a hydratable form, and to chelate minor metals that are present in the crude oil. The phosphatides and the metal salts are removed from the oil along with the soapstock. The oil-acid mixture is treated with sodium hydroxide solution to neutralize the free fatty acids and the phosphoric acid in the acid-oil mixture. The neutralized free fatty acids, phosphatides, etc. (soapstock) are drained off from the neutralized oil. A water wash may be done to further reduce the soap content of the oil. The oil may be bleached and deodorized before use, if desired, by techniques known in the art.

Oils obtained from plant described herein can have increased oxidative stability, which can be measured using, for example, an Oxidative Stability Index Instrument (e.g., from Omnion, Inc., Rockland, Mass.) according to AOCS Official Method Cd 12b-92 (revised 1993). Oxidative stability is often expressed in terms of "AOM" hours.

Food Compositions

This document also features food compositions containing the oils described above. For example, oils having a low (6% or less) or no (3.5% or less) total saturated fatty acid content in combination with a typical (60-70%), mid (71-80%), or high (>80%) oleic acid content can be used to replace or reduce the amount of saturated fatty acids and hydrogenated oils (e.g., partially hydrogenated oils) in various food products such that the levels of saturated fatty acids and trans fatty acids are reduced in the food products. In particular, canola oils having a low total saturated fatty acid content and a mid or high oleic acid content in combination with a low linolenic acid content can be used to replace or reduce the amount of saturated fats and partially hydrogenated oils in processed or packaged food products, including bakery products such as cookies, muffins, doughnuts, pastries (e.g., toaster pastries), pie fillings, pie crusts, pizza crusts, frostings, breads, biscuits, and cakes, breakfast cereals, breakfast bars, puddings, and crackers.

For example, an oil described herein can be used to produce sandwich cookies that contain reduced saturated fatty acids and no or reduced levels of partially hydrogenated oils in the cookie and/or crème filling. Such a cookie composition can include, for example, in addition to canola oil, flour, sweetener (e.g., sugar, molasses, honey, high fructose corn syrup, artificial sweetener such as sucralose, saccharine, aspartame, or acesulfame potassium, and combinations thereof), eggs, salt, flavorants (e.g., chocolate, vanilla, or lemon), a leavening agent (e.g., sodium bicarbonate or other baking acid such as monocalcium phosphate monohydrate, sodium aluminum sulfate, sodium acid pyrophosphate, sodium aluminum phosphate, dicalcium phosphate, glucano-deltalactone, or potassium hydrogen tartrate, or combinations thereof), and optionally, an emulsifier (e.g., mono- and diglycerides of fatty acids, propylene glycol mono- and di-esters of fatty acids, glycerollactose esters of fatty acids, ethoxylated or succinylated mono- and diglycerides, lecithin, diacetyl tartaric acid esters or mono- and diglycerides, sucrose esters of glycerol, and combinations thereof). A crème filling composition can include, in addition to canola oil, sweetener (e.g., powdered sugar, granulated sugar, honey, high fructose corn syrup, artificial sweetener, or combinations thereof), flavorant (e.g., vanilla, chocolate, or lemon), salt, and, optionally, emulsifier.

Canola oils (e.g., with low total saturated fatty acid content, low oleic acid, and low linolenic acid content) also are useful for frying applications due to the polyunsaturated content, which is low enough to have improved oxidative stability for frying yet high enough to impart the desired fried flavor to the food being fried. For example, canola oils can be used to produce fried foods such as snack chips (e.g., corn or potato chips), French fries, or other quick serve foods.

Oils described herein also can be used to formulate spray coatings for food products (e.g., cereals or snacks such as crackers). In some embodiments, the spray coating can include other vegetable oils such as sunflower, cottonseed, corn, or soybean oils. A spray coating also can include an antioxidant and/or a seasoning.

Oils described herein also can be use in the manufacturing of dressings, mayonnaises, and sauces to provide a reduction in the total saturated fat content of the product. The low saturate oil can be used as a base oil for creating structured fat solutions such as microwave popcorn solid fats or canola butter formulations.

The invention will be further described in the following examples, which do not limit the scope of the invention described in the claims.

EXAMPLES

In the Tables described herein, the fatty acids are referred to by the length of the carbon chain and number of double bonds within the chain. For example, C140 refers to C14:0 or myristic acid; C160 refers to C16:0 or palmitic acid; C180 refers to C18:0 or stearic acid; C181 refers to C18:1 or oleic acid; C182 refers to C18:2 or linoleic acid; C183 refers to C18:3 or α-linolenic acid; C200 refers to C20:0 or archidic acid; C201 refers to C20:1 or eicosenoic acid, C220 refers to C22:0 or behenic acid, C221 refers to C22:1 or erucic acid, C240 refers to C24:0 or lignoceric acid, and C241 refers to C24:1 or nervonic acid. "Total Sats" refers to the total of C140, C160, C180, C200, C220, and C240. Representative fatty acid profiles are provided for each of the specified samples.

Unless otherwise indicated, all percentages refer to wt % based on total wt % of fatty acids in the oil.

Example 1

Brassica Plant Line 15.24

Plants producing an oil with a high oleic acid and low total saturated fatty acid content were obtained from crosses of plants designated 90A24 and plants designated 90122. 90A24 plants were obtained from a cross between HIO 11-5, a high oleic acid selection from the IMC 129 lineage (ATCC Deposit No. 40811; U.S. Pat. No. 5,863,589), and LS 6-5, a low saturated fatty acid selection from the IMC 144 lineage (ATCC Deposit No. 40813; U.S. Pat. No. 5,668,299). 90122 plants were obtained from a cross between LS 4-3, a low saturated fatty acid selection from the IMC 144 lineage (ATCC Deposit No. 40813) and D336, a low α-linolenic acid selection from the IMC 01 lineage (ATCC Deposit No. 40579; U.S. Pat. No. 5,750,827). Table 1 contains the fatty acid profile for the LS6-5, LS4-3, and HIO 11-5 parent lines, as well as IMC 01.

TABLE 1

Seed Fatty Acid Profile of Parental Lines

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| LS0004-3 | 0 | 3.01 | 0.00 | 1.27 | 66.75 | 20.03 | 6.08 | 0.45 | 1.31 | 0.11 | 0.26 | 0 | 0.14 | 0.12 | 5.12 |
| LS0006-5 | 0 | 3.07 | 0.06 | 1.11 | 64.83 | 22.18 | 6.10 | 0.40 | 1.29 | 0.11 | 0.24 | 0 | 0.13 | 0.13 | 4.94 |
| HIO011-5 | 0 | 3.79 | 0.24 | 1.91 | 78.60 | 7.86 | 4.64 | 0.71 | 1.44 | 0.00 | 0.39 | 0 | 0.23 | 0.00 | 7.04 |
| IMC 01 | 0 | 4.81 | 0.31 | 2.48 | 61.9i | 24.81 | 2.61 | 0.85 | 1.06 | 0.07 | 0.48 | 0 | 0.33 | 0.15 | 9.02 |

The $F_1$ generation progeny of crosses between 90A24 and 90122 were designated 91AS. $F_1$ 91AS plants were self-pollinated to produce $F_2$ seeds, which were harvested and analyzed for fatty acid composition by gas chromatography (GC). $F_2$ seeds having a low linolenic acid content and high oleic acid content were planted and self-pollinated to produce $F_3$ seeds. The fatty acid composition of $F_3$ seeds was analyzed. $F_3$ seeds having a high oleic acid and low linolenic acid content were planted to generate $F_3$ plants, which were selfed to produce $F_4$ seeds. The fatty acid composition of $F_4$ seeds was analyzed by GC. $F_4$ seeds having a high oleic acid and low linolenic acid content were planted to generate $F_4$ plants, of which 8 plants were self-pollinated to produce $F_5$ seeds. The fatty acid composition of $F_5$ seeds was analyzed by GC (Table 2).

$F_5$ seeds from one of the lines designated 91AS51057 was selected based on a total saturated fatty acid level of 4.99%, with low palmitic acid of 2.64% and stearic acid of 1.33% (Table 2). This line also had a higher eicosenoic acid (C20:1) content of 1.73%. The seeds of this selection ($F_5$ 91AS51057) were planted to generate $F_5$ plants, which were selfed to produce $F_6$ seeds. $F_6$ seeds were harvested from three of five selfed plants. The fatty acid composition of $F_6$ seeds harvested from each of the three plants is shown in Table 3. Selfing and selection within the 91AS51057 line were continued for additional 5 generations. Table 4 provides the fatty acid composition for field harvested $F_{10}$ seeds from 22 lines of self-pollinated 91AS51057 plants. The total saturated fatty acid content ranged from 4.38 to 6.28%, oleic acid content ranged from 74.9 to 82.5%, and α-linolenic acid content ranged from 2.1 to 4.8%. The eicosenoic acid content ranged from 1.28% to 2.30%, with most 91AS51057 $F_9$ plants producing $F_{10}$ seeds having an eicosenoic acid content from 1.90% to 2.25%. See Table 4. Seed of four individual $F_{10}$ 91AS51057 lines (X723868, X723977, X724734, and X724738) were selected and their seeds planted in the field in individual isolation tents. The low total saturate line X724734 was designated as 15.24 based on its nursery field position of range 15, row 24, and used in future crosses to introduce traits for low saturates through the reduction of palmitic and stearic acids. Line 15.24 also retained the higher level of eicosinoic acid of 2.06% associated with the saturate reduction.

lation was developed from a cross between 15.24 and 01OB240, a B line used in the maintenance of cytoplasmic male sterile (CMS) A lines for hybrid production. The two parental lines were screened with 1066 SNP (single nucleotide polymorphism) markers using the MassARRAY platform (Sequenom Inc., San Diego, Calif.) to identify polymor-

TABLE 2

Fatty Acid Composition of Field Harvested $F_5$ Seed from Self-pollinated Plants

| TRIAL_ID | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| 91AS51023 | 0.05 | 3.32 | 0.18 | 1.03 | 65.59 | 18.89 | 7.95 | 0.58 | 1.46 | 0.07 | 0.43 | 0.03 | 0.21 | 0.21 | 5.62 |
| 91AS51026 | 0.09 | 4.50 | 0.32 | 1.57 | 63.81 | 24.19 | 2.90 | 0.55 | 1.25 | 0.07 | 0.39 | 0.02 | 0.20 | 0.14 | 7.30 |
| 91AS51026 | 0.09 | 4.36 | 0.29 | 1.51 | 63.09 | 25.21 | 3.11 | 0.49 | 1.14 | 0.07 | 0.33 | 0.01 | 0.17 | 0.13 | 6.95 |
| 91AS51028 | 0.06 | 3.91 | 0.25 | 1.35 | 64.68 | 24.32 | 3.08 | 0.46 | 1.19 | 0.05 | 0.31 | 0.03 | 0.16 | 0.15 | 6.27 |
| 91AS51028 | 0.06 | 3.71 | 0.24 | 1.32 | 64.77 | 24.38 | 2.97 | 0.47 | 1.30 | 0.05 | 0.34 | 0.04 | 0.16 | 0.19 | 6.06 |
| 91AS51034 | 0.04 | 2.68 | 0.17 | 1.31 | 74.75 | 11.44 | 5.88 | 0.57 | 1.88 | 0.25 | 0.42 | 0.20 | 0.26 | 0.17 | 5.27 |
| 91AS51044 | 0.02 | 2.66 | 0.17 | 1.35 | 75.19 | 12.23 | 5.20 | 0.54 | 1.81 | 0.12 | 0.34 | 0.04 | 0.18 | 0.16 | 5.08 |
| 91AS51057 | 0.03 | 2.64 | 0.16 | 1.33 | 71.68 | 12.85 | 8.23 | 0.50 | 1.73 | 0.08 | 0.36 | 0.09 | 0.14 | 0.18 | 4.99 |

TABLE 3

Fatty Acid Composition of Field Harvested $F_6$ Generation Seed of 91AS51057

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| 91AS51057 | 0.02 | 2.98 | 0.13 | 2.30 | 78.00 | 9.12 | 2.67 | 0.97 | 2.00 | 0.11 | 0.65 | 0.06 | 0.45 | 0.53 | 7.37 |
| 91AS51057 | 0.03 | 2.86 | 0.14 | 1.41 | 73.94 | 12.02 | 5.74 | 0.61 | 1.95 | 0.10 | 0.43 | 0.05 | 0.25 | 0.49 | 5.58 |
| 91AS51057 | 0.02 | 2.89 | 0.13 | 2.07 | 76.29 | 10.06 | 3.35 | 0.92 | 2.17 | 0.13 | 0.65 | 0.06 | 0.49 | 0.76 | 7.05 |

TABLE 4

Fatty Acid Composition of Field Harvest $F_{10}$ Generation Seed of 91AS51057

| Line | Sample Number | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|---|
| 91AS51057 | X723860 | 0.04 | 3.16 | 0.19 | 1.10 | 78.79 | 9.13 | 3.37 | 0.53 | 2.05 | 0.30 | 0.37 | 0.05 | 0.24 | 0.68 | 5.43 |
| 91AS51057 | X723861 | 0.04 | 2.94 | 0.18 | 1.58 | 81.26 | 7.55 | 2.79 | 0.65 | 1.91 | 0.08 | 0.38 | 0.05 | 0.25 | 0.34 | 5.84 |
| 91AS51057 | X723862 | 0.04 | 3.01 | 0.19 | 1.69 | 80.31 | 7.83 | 2.81 | 0.71 | 2.02 | 0.09 | 0.44 | 0.06 | 0.32 | 0.50 | 6.21 |
| 91AS51057 | X723863 | 0.04 | 2.97 | 0.19 | 1.87 | 80.88 | 7.37 | 2.95 | 0.73 | 1.79 | 0.07 | 0.41 | 0.05 | 0.25 | 0.44 | 6.27 |
| 91AS51057 | X723868 | 0.04 | 2.66 | 0.17 | 0.92 | 78.20 | 10.71 | 3.81 | 0.39 | 2.11 | 0.12 | 0.26 | 0.06 | 0.11 | 0.44 | 4.38 |
| 91AS51057 | X723869 | 0.04 | 3.17 | 0.21 | 1.18 | 80.01 | 8.47 | 2.99 | 0.50 | 2.16 | 0.12 | 0.34 | 0.05 | 0.24 | 0.51 | 5.47 |
| 91AS51057 | X723924 | 0.04 | 2.81 | 0.16 | 1.11 | 80.23 | 9.38 | 3.01 | 0.42 | 1.93 | 0.12 | 0.23 | 0.03 | 0.12 | 0.39 | 4.74 |
| 91AS51057 | X723931 | 0.04 | 2.82 | 0.15 | 0.91 | 79.65 | 9.22 | 3.33 | 0.41 | 2.13 | 0.14 | 0.27 | 0.06 | 0.13 | 0.74 | 4.58 |
| 91AS51057 | X723932 | 0.10 | 2.75 | 0.15 | 0.98 | 79.62 | 9.21 | 3.15 | 0.44 | 2.18 | 0.16 | 0.31 | 0.05 | 0.15 | 0.76 | 4.73 |
| 91AS51057 | X723933 | 0.02 | 2.81 | 0.14 | 0.93 | 80.13 | 9.15 | 3.31 | 0.41 | 2.15 | 0.13 | 0.26 | 0.04 | 0.14 | 0.40 | 4.56 |
| 91AS51057 | X723970 | 0.04 | 3.25 | 0.25 | 1.73 | 82.09 | 8.11 | 2.34 | 0.51 | 1.28 | 0.05 | 0.19 | 0.00 | 0.10 | 0.06 | 5.83 |
| 91AS51057 | X723971 | 0.04 | 3.20 | 0.23 | 1.68 | 82.46 | 7.79 | 2.25 | 0.52 | 1.29 | 0.05 | 0.22 | 0.01 | 0.13 | 0.12 | 5.79 |
| 91AS51057 | X723977 | 0.04 | 2.72 | 0.19 | 1.19 | 80.64 | 9.76 | 2.10 | 0.52 | 1.92 | 0.07 | 0.32 | 0.02 | 0.15 | 0.35 | 4.95 |
| 91AS51057 | X723978 | 0.03 | 2.84 | 0.13 | 1.04 | 80.36 | 8.24 | 3.56 | 0.58 | 2.30 | 0.12 | 0.38 | 0.00 | 0.23 | 0.20 | 5.09 |
| 91AS51057 | X723984 | 0.04 | 2.73 | 0.16 | 1.01 | 79.33 | 9.37 | 4.00 | 0.45 | 1.97 | 0.10 | 0.29 | 0.04 | 0.14 | 0.36 | 4.66 |
| 91AS51057 | X724733 | 0.04 | 3.22 | 0.24 | 1.33 | 74.93 | 12.62 | 4.76 | 0.52 | 1.67 | 0.07 | 0.28 | 0.02 | 0.13 | 0.17 | 5.51 |
| 91AS51057 | X724734 | 0.03 | 2.82 | 0.18 | 0.98 | 80.14 | 8.92 | 3.27 | 0.44 | 2.24 | 0.13 | 0.28 | 0.04 | 0.16 | 0.37 | 4.72 |
| 91AS51057 | X724735 | 0.03 | 2.80 | 0.17 | 1.08 | 79.37 | 9.54 | 3.38 | 0.45 | 2.24 | 0.13 | 0.26 | 0.04 | 0.16 | 0.34 | 4.79 |
| 91AS51057 | X724736 | 0.04 | 3.16 | 0.25 | 1.73 | 80.96 | 7.68 | 2.59 | 0.70 | 1.90 | 0.07 | 0.40 | 0.05 | 0.25 | 0.23 | 6.28 |
| 91AS51057 | X724737 | 0.04 | 2.80 | 0.20 | 1.54 | 80.29 | 8.36 | 3.49 | 0.64 | 1.75 | 0.06 | 0.38 | 0.04 | 0.17 | 0.25 | 5.57 |
| 91AS51057 | X724738 | 0.03 | 2.72 | 0.17 | 1.12 | 81.88 | 7.71 | 2.84 | 0.52 | 2.06 | 0.10 | 0.32 | 0.05 | 0.17 | 0.30 | 4.89 |
| 91AS51057 | X724754 | 0.04 | 2.79 | 0.18 | 1.64 | 80.73 | 8.19 | 3.39 | 0.60 | 1.64 | 0.06 | 0.33 | 0.03 | 0.16 | 0.22 | 5.56 |
| AVERAGE | | 0.04 | 2.92 | 0.19 | 1.29 | 80.1 | 8.83 | 3.16 | 0.53 | 1.94 | 0.11 | 0.31 | 0.04 | 0.18 | 0.37 | 5.27 |

Example 2

Identification of FatA2 Mutation in 15.24 Plants

Genome mapping, map-based gene cloning, and direct-sequencing strategies were used to identify loci associated with the low total saturated fatty acid phenotype in the 15.24 lines described in Example 1. A DH (doubled haploid) popuphic SNP markers between the two parents; 179 polymorphic SNP markers were identified.

Single marker correlations between fatty acid components and SNP markers were carried out using the SAS program (SAS Institute 1988). A *Brassica napus* genetic linkage map was constructed using the Kosambi function in JoinMap 3.0 (Kyazma). Interval quantitative trait loci (QTL) mapping was done with MapQTL 4.0 (Kyazma). A LOD score>3.0 was considered as threshold to declare the association intervals. For fine QTL mapping, a BC$_3$S (backcrossing self) population was developed from a cross between 15.24 and 01PR06RR.001B, a canola R (restorer) line. SNP haplotype blocks and recombinant/crossover events within the identified QTL interval were identified using MS Excel® program.

Comparative genome mapping was performed to locate the identified QTL in Brassica napus chromosomes and further identify the Brassica rapa BAC (Bacterial Artificial chromosome) clones encompassing the identified SNP markers and the candidate genes in the identified QTL interval for the low total saturated fatty acid using publicly available Brassica and Arabidosis genome sequences, genes, genetic linkage maps, and other information from the world wide web at brassica.bbsrc.ac.uk/, and ncbi.nlm.nih.gov/.

A total of 148 DH lines were genotyped with 179 polymorphic SNP markers. QTL mapping identified a major QTL interval (5 cM) compassing 7 SNP markers for saturated fatty acid content (C18:0 and C20:0). Fine mapping using 610 BC$_3$S$_1$ lines from a cross between 15.24 and 01PR06RR.001B, a canola restorer line, identified two SNP markers flanking a 1 cM QTL interval that was associated with the low total saturated fatty acid phenotype. Comparative genome mapping located this QTL in the N3 chromosome and further identified a FatA2 candidate within this QTL interval.

Figure 4:
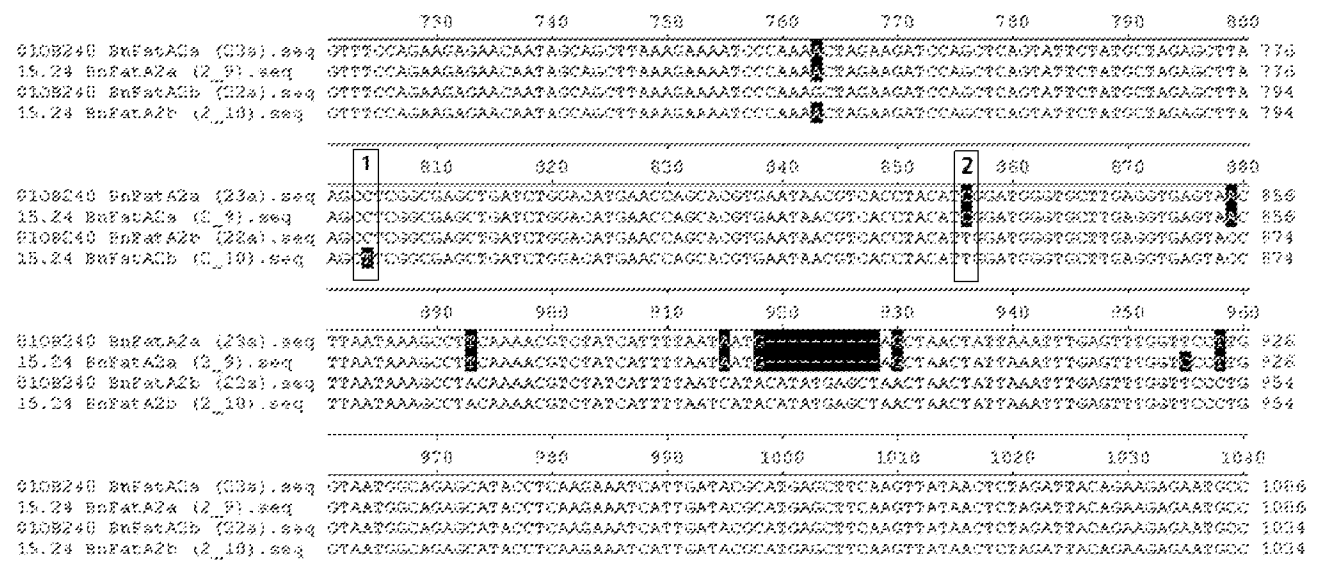

DNA from lines 15.24 and 01OB240 was used as a template to amplify FatA sequences. Resultant sequences were analyzed using BLAST (the Basic Local Alignment Search Tool) and MegAlign and EditSeq programs from DNASTAR/Lasergene 8.0 (DNASTAR, Inc). Isoforms of FatA1 and FatA2 were amplified and a representative sampling is shown in FIG. 1. The BnFatA1 sequence from 15.24 is homologous the B. rapa FatA1 and A. thaliana FatA1 sequence, while the BnFatA2 sequence from 15.24 is homologous to the AtFatA2 and B. napus pNL2 sequences. Two isoforms (or alleles) of FatA2 were evident in the sequencing results and were named FatA2a and FatA2b. Differences between the sequences of these two isoforms are shown in FIG. 4. FIGS. 1 and 2 show a representative nucleotide (position labeled "2;" only the FatA2b isoform is represented in FIG. 1) where, in that position, FatA2a is a "C" and FatA2b is a "T" (summarized in FIG. 4). The FatA2 sequencing results indicated that within the FatA2b isoform sequences, 15.24 contained a single nucleotide polymorphism represented by position labeled "1" in FIGS. 1, 2 and 4. In 15.24, the FatA2b sequences contain a "C" to "T" mutation that was not present in the 01OB240 sequences ("1" in FIGS. 1,2, 4). The nucleotide substitution of position "1" in FIGS. 1 and 2 corresponds to position 942 of the FatA2 coding sequence (numbering based on the Arabidopsis thaliana sequence set forth in GenBank Accession No. NM_117374.3) and results in the substitution of a leucine residue for proline at position 255 of the encoded protein. See SEQ ID NO:28 and SEQ ID NO:32, which provide representative nucleotide sequences of the Brassica napus FatA2b gene from 15.24. In FIG. 4, position 798 is marked at the "C" to "T" SNP that correlates with low saturate content in the 15.24 lines. SEQ ID NO:29 contains the amino acid sequence of residues 242 to 277 of a wild-type B. napus FatA2 polypeptide. Position 14 of SEQ ID NO:29 (position 255 in the full-length amino acid sequence) is a leucine in the FatA2 polypeptide from 15.24. SEQ ID NO:30 contains the wild-type Arabidopsis FatA2 polypeptide. SEQ ID NO:31 contains the predicted amino acid sequence of the B. napus FATA2b polypeptide from exons 2-6.

FIG. 3 contains an alignment of the conserved region around position 255 in the Arabidopsis FatA2 protein, and Brassica FatA2 protein from 15.24 and 01OB240. The proline at position 255 is conserved among Brassica, Arabidopsis, B. napus, B. rapa, B. juncea, Zea mays, Sorghum bicolor, Oryza sativa Indica (rice), Triticum aestivum, Glycine max, Jatropha (tree species), Carthamus tinctorius, Cuphea hookeriana, Iris tectorum, Perilla frutescens, Helianthus annuus, Garcinia mangostana, Picea sitchensis, Physcomitrella patens subsp. Patens, Elaeis guineensis, Vitis vinifera, Elaeis oleifera, Camellia oleifera, Arachis hypogaea, Capsicum annuum, Cuphea hookeriana, Populus trichocarpa, and Diploknema butyracea. Furthermore, many amino acids in the region spanning amino acids 242 to 277 are homologous in both FatA and FatB (see Fett/Lipid 100 (1998) 167-172) in Arabidopsis and Brassica.

FIG. 4 shows a portion of representative BnFatA2a and BnFatA2b sequences from 01OB240 and 15.24 germplasm. The positions labeled "1" and "2" correspond to the "1" and "2" positions in FIGS. 1, 2 and 3.

Large scale screening of the parental lines (15.24 and 0101OB240) as well as other germplasm populations (including IMC144, IMC129, Q508, and Q7415) indicated the FatA2 SNP was 15.24-specific and was statistically significantly associated with the low total saturated fatty acid phenotype (R-square=0.28 for total saturated content, R-square=0.489 for C18:0; R-square=0.385 for C20:0) and increased eicosenoic acid content (R-square=0.389). The FatA2 SNP1 mutation was not significantly associated with the percent C14:0 and C16:0 content of oil from 15.24 plants. However, it was found that the C 18:0 content of oil from 15.24 plants was negatively correlated with C20:1 content (R-value=−0.61).

Example 3

Brassica Line 15.36

Plants producing an oil with a high oleic acid and low total saturated fatty acid content were obtained from crosses of plants from lines A12.20010 and Q508. The A12.20010 line was obtained from a cross of a selection from the IMC144 lineage and a selection from the IMC129 lineage. Line Q508 is a high oleic acid line that contains a mutation in each of the fad2 D and F genes. See Examples 5 and 7 of U.S. Pat. No. 6,342,658.

Plants designated 92EP.1039 were selected on the basis of fatty acid composition from progeny of the A12.20010×Q508 cross. 92EP.1039 plants were crossed with plants of Trojan, a commercially available Canadian spring canola variety. The F$_1$ generation progeny of 92EP.1039 and Trojan were designated 93PI. F$_1$ 93PI plants were self-pollinated to produce F$_2$ seeds, which were harvested and analyzed for fatty acid composition by GC.

F$_2$ seeds having a high oleic acid content were selected and planted to obtained F$_2$ plants. The F$_2$ plants were self-pollinated to produce F$_3$ seeds. The fatty acid composition of F$_3$ seeds was analyzed. Table 5 contains the fatty acid profile of 93PI2I F$_3$ seeds from 13 different F$_2$ plants. F$_3$ 93PI2I seeds having a low saturated fatty acid content were planted to generate F$_3$ plants, which were selfed to produce F$_4$ seeds. The fatty acid composition of F$_4$ 93PI2I seeds was analyzed by GC. Table 6 contains the fatty acid profile of F$_4$ 93PI2I seeds from thirteen different self-pollinated F$_3$ plants. The three 93PI2I plants (T7440796, T740797, and T740799) with the lowest total saturated fatty acid content were subjected to additional rounds of selfing and selection for low total saturated fatty acid content for 5 generations. The 93PI2I line T740799 was designated as 93PI41003 at the $F_4$ generation and advanced. Table 7 provides the fatty acid composition for $F_8$ seeds harvested from 24 self-pollinated $F_7$ generation 93PI41003 plants. The results indicate that total saturated fatty acid content ranged from 4.51% to 6.29%, oleic acid content ranged from 64 to 71%, and α-linolenic acid content ranged from 4.8 to 7.5%. The eicosenoic acid content ranged from 1.51% to 1.99%. The 93PI41003 $F_8$ plant line X727712 was renamed as line 15.36 based on its nursery field position of range 15, row 36, and had a total saturated fatty acid composition of 4.51%, with reduced palmitic acid of 2.65% and stearic acid of 0.94%. Line 15.36 was used in crosses to introduce low saturate traits to other genetic backgrounds

TABLE 5

Seed Fatty Acid Composition of $F_3$ Generation of 93PI21

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| 93PI21 | 0.04 | 3.15 | 0.22 | 1.77 | 80.06 | 6.95 | 4.23 | 0.75 | 1.77 | 0.08 | 0.43 | 0.04 | 0.33 | 0.19 | 6.46 |
| 93PI21 | 0.04 | 3.22 | 0.21 | 1.29 | 79.05 | 7.82 | 4.90 | 0.60 | 1.79 | 0.09 | 0.37 | 0.07 | 0.31 | 0.24 | 5.82 |
| 93PI21 | 0.03 | 3.32 | 0.28 | 1.69 | 77.63 | 8.95 | 4.31 | 0.73 | 1.88 | 0.09 | 0.47 | 0.07 | 0.35 | 0.20 | 6.59 |
| 93PI21 | 0.04 | 3.57 | 0.33 | 1.43 | 81.33 | 6.09 | 3.89 | 0.63 | 1.61 | 0.05 | 0.41 | 0.17 | 0.25 | 0.20 | 6.34 |
| 93PI21 | 0.05 | 3.47 | 0.34 | 1.38 | 80.70 | 6.28 | 4.85 | 0.58 | 1.55 | 0.05 | 0.35 | 0.05 | 0.22 | 0.13 | 6.05 |
| 93PI21 | 0.05 | 3.63 | 0.34 | 1.41 | 80.06 | 6.54 | 4.99 | 0.60 | 1.57 | 0.05 | 0.37 | 0.04 | 0.22 | 0.15 | 6.27 |
| 93PI21 | 0.03 | 3.14 | 0.25 | 1.33 | 77.85 | 8.98 | 4.98 | 0.59 | 1.80 | 0.07 | 0.40 | 0.15 | 0.24 | 0.19 | 5.72 |
| 93PI21 | 0.03 | 3.00 | 0.24 | 1.34 | 77.65 | 8.02 | 6.23 | 0.61 | 1.90 | 0.08 | 0.40 | 0.06 | 0.24 | 0.22 | 5.60 |
| 93PI21 | 0.06 | 3.66 | 0.38 | 1.73 | 77.25 | 8.83 | 4.87 | 0.72 | 1.53 | 0.06 | 0.44 | 0.00 | 0.31 | 0.16 | 6.91 |
| 93PI21 | 0.08 | 4.34 | 0.52 | 2.17 | 77.22 | 6.57 | 4.94 | 0.99 | 1.75 | 0.06 | 0.66 | 0.07 | 0.40 | 0.24 | 8.64 |
| 93PI21 | 0.05 | 3.49 | 0.39 | 1.71 | 85.90 | 2.86 | 2.94 | 0.64 | 1.32 | 0.04 | 0.32 | 0.00 | 0.22 | 0.15 | 6.43 |
| 93PI21 | 0.04 | 3.13 | 0.25 | 1.44 | 80.58 | 6.99 | 4.31 | 0.60 | 1.81 | 0.07 | 0.36 | 0.04 | 0.23 | 0.15 | 5.80 |
| 93PI21 | 0.05 | 4.21 | 0.24 | 1.66 | 73.40 | 14.31 | 2.83 | 0.67 | 1.45 | 0.04 | 0.45 | 0.03 | 0.50 | 0.16 | 7.54 |

TABLE 6

Seed Fatty Acid Composition of Field Grown $F_4$ Seed Generation of 93PI21

| Line | Sample No. | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|---|
| 93PI21 | T738147 | 0.03 | 2.78 | 0.15 | 1.60 | 69.57 | 13.82 | 8.81 | 0.62 | 1.77 | 0.08 | 0.37 | 0.04 | 0.14 | 0.22 | 5.54 |
| 93PI21 | T738149 | 0.04 | 2.87 | 0.17 | 1.47 | 71.02 | 11.74 | 9.63 | 0.57 | 1.75 | 0.07 | 0.35 | 0.00 | 0.12 | 0.21 | 5.42 |
| 93PI21 | T738148 | 0.05 | 3.35 | 0.29 | 1.84 | 73.71 | 11.27 | 5.81 | 0.64 | 1.40 | 0.07 | 0.35 | 0.06 | 0.17 | 0.99 | 6.40 |
| 93PI21 | T740387 | 0.04 | 3.28 | 0.22 | 1.68 | 65.96 | 15.57 | 9.38 | 0.62 | 1.89 | 0.14 | 0.46 | 0.06 | 0.29 | 0.41 | 6.36 |
| 93PI21 | T740388 | 0.03 | 3.00 | 0.20 | 1.66 | 71.33 | 11.89 | 8.15 | 0.63 | 1.93 | 0.10 | 0.49 | 0.05 | 0.29 | 0.26 | 6.09 |
| 93PI21 | T740389 | 0.03 | 2.72 | 0.20 | 1.42 | 75.27 | 8.72 | 7.90 | 0.57 | 2.06 | 0.10 | 0.46 | 0.06 | 0.22 | 0.27 | 5.42 |
| 93PI21 | T740749 | 0.03 | 2.86 | 0.18 | 1.31 | 68.64 | 13.27 | 10.44 | 0.50 | 1.90 | 0.09 | 0.34 | 0.06 | 0.16 | 0.22 | 5.21 |
| 93PI21 | T740797 | 0.03 | 2.99 | 0.21 | 1.23 | 72.19 | 10.92 | 9.37 | 0.48 | 1.78 | 0.07 | 0.33 | 0.04 | 0.14 | 0.22 | 5.20 |
| 93PI21 | T740798 | 0.03 | 2.78 | 0.20 | 1.26 | 76.73 | 7.47 | 7.39 | 0.58 | 2.35 | 0.14 | 0.47 | 0.07 | 0.18 | 0.34 | 5.29 |
| 93PI21 | T740799 | 0.03 | 3.03 | 0.22 | 1.19 | 72.63 | 11.46 | 8.18 | 0.49 | 1.76 | 0.11 | 0.37 | 0.05 | 0.17 | 0.34 | 5.27 |
| 93PI21 | T738147 | 0.03 | 2.78 | 0.15 | 1.60 | 69.57 | 13.82 | 8.81 | 0.62 | 1.77 | 0.08 | 0.37 | 0.04 | 0.14 | 0.22 | 5.54 |
| 93PI21 | T7381149 | 0.04 | 2.87 | 0.17 | 1.47 | 71.02 | 11.74 | 9.63 | 0.57 | 1.75 | 0.007 | 0.35 | 0.00 | 0.12 | 0.21 | 5.42 |
| 93PI21 | T738148 | 0.05 | 3.35 | 0.29 | 1.84 | 73.71 | 11.27 | 5.81 | 0.64 | 1.40 | 0.07 | 0.35 | 0.06 | 0.17 | 0.99 | 6.40 |

TABLE 7

Fatty Acid Composition of $F_9$ Seeds from 93PI41003 Plants in Isolation Tents

| RESCHID | SAMPLE ID | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|---|
| 93PI41003 | X723830 | 0.04 | 2.99 | 0.23 | 1.21 | 60.88 | 23.17 | 8.30 | 0.53 | 1.67 | 0.12 | 0.33 | 0.04 | 0.18 | 0.33 | 5.26 |
| 93PI41003 | X723846 | 0.03 | 2.73 | 0.22 | 1.22 | 66.06 | 20.77 | 6.22 | 0.45 | 1.57 | 0.09 | 0.26 | 0.03 | 0.15 | 0.22 | 4.83 |
| 93PI41003 | X723847 | 0.04 | 2.89 | 0.20 | 1.18 | 68.08 | 17.98 | 6.16 | 0.54 | 1.89 | 0.10 | 0.33 | 0.03 | 0.23 | 0.35 | 5.21 |
| 93PI41003 | X723848 | 0.03 | 2.80 | 0.21 | 1.23 | 64.93 | 20.91 | 7.09 | 0.47 | 1.58 | 0.08 | 0.27 | 0.02 | 0.15 | 0.22 | 4.95 |
| 93PI41003 | X723882 | 0.06 | 2.84 | 0.20 | 1.38 | 69.81 | 16.49 | 5.47 | 0.58 | 1.94 | 0.10 | 0.39 | 0.06 | 0.27 | 0.41 | 5.53 |
| 93PI41003 | X723883 | 0.04 | 2.87 | 0.19 | 1.35 | 68.41 | 17.07 | 5.98 | 0.60 | 1.95 | 0.14 | 0.42 | 0.06 | 0.31 | 0.61 | 5.59 |
| 93PI41003 | X723916 | 0.04 | 3.12 | 0.17 | 1.43 | 69.74 | 16.59 | 5.19 | 0.63 | 1.99 | 0.09 | 0.41 | 0.04 | 0.31 | 0.25 | 5.93 |
| 93PI41003 | X723917 | 0.02 | 2.51 | 0..20 | 1.02 | 65.86 | 19.54 | 7.61 | 0.41 | 1.77 | 0.11 | 0.29 | 0.04 | 0.11 | 0.53 | 4.35 |
| 93PI41003 | X723918 | 0.03 | 2.48 | 0.17 | 1.20 | 68.96 | 17.58 | 5.99 | 0.52 | 1.94 | 0.09 | 0.33 | 0.04 | 0.19 | 0.49 | 4.74 |
| 93PI41003 | X723919 | 0.03 | 3.12 | 0.18 | 1.10 | 67.25 | 18.48 | 6.46 | 0.48 | 1.90 | 0.11 | 0.32 | 0.04 | 0.23 | 0.31 | 5.27 |
| 93PI41003 | X724063 | 0.04 | 2.73 | 0.19 | 1.18 | 66.70 | 19.56 | 6.43 | 0.50 | 1.80 | 0.09 | 0.29 | 0.02 | 0.18 | 0.28 | 4.92 |
| 93PI41003 | X724064 | 0.04 | 2.71 | 0.21 | 1.22 | 64.00 | 21.73 | 7.06 | 0.45 | 1.60 | 0.08 | 0.27 | 0.04 | 0.15 | 0.44 | 4.83 |
| 93PI41003 | X724077 | 0.03 | 2.60 | 0.16 | 1.16 | 67.89 | 19.14 | 5.78 | 0.52 | 1.87 | 0.09 | 0.32 | 0.04 | 0.19 | 0.20 | 4.82 |
| 93PI41003 | X724091 | 0.03 | 2.72 | 0.18 | 1.27 | 68.62 | 18.11 | 5.76 | 0.57 | 1.93 | 0.10 | 0.34 | 0.00 | 0.18 | 0.19 | 5.11 |
| 93PI41003 | X724092 | 0.03 | 2.65 | 0.19 | 1.11 | 63.98 | 21.64 | 7.13 | 0.45 | 1.81 | 0.10 | 0.28 | 0.03 | 0.16 | 0.44 | 4.69 |
| 93PI41003 | X724093 | 0.03 | 2.57 | 0.19 | 1.21 | 67.35 | 19.67 | 5.77 | 0.47 | 1.80 | 0.09 | 0.29 | 0.04 | 0.18 | 0.36 | 4.74 |
| 93PI41003 | X724412 | 0.03 | 2.65 | 0.18 | 0.94 | 65.27 | 20.41 | 7.54 | 0.44 | 1.71 | 0.09 | 0.26 | 0.04 | 0.18 | 0.26 | 4.51 |
| 93PI41003 | X724416 | 0.04 | 3.02 | 0.22 | 1.19 | 68.18 | 18.57 | 5.49 | 0.54 | 1.67 | 0.08 | 0.34 | 0.05 | 0.29 | 0.33 | 5.41 |
| 93PI41003 | X724417 | 0.04 | 2.72 | 0.23 | 1.05 | 66.68 | 19.31 | 6.59 | 0.47 | 1.93 | 0.11 | 0.31 | 0.05 | 0.17 | 0.35 | 4.75 |

TABLE 7-continued

Fatty Acid Composition of F₉ Seeds from 93PI41003 Plants in Isolation Tents

| RESCHID | SAMPLE ID | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|---|
| 93PI41003 | X724420 | 0.03 | 2.81 | 0.19 | 1.22 | 69.48 | 17.31 | 5.43 | 0.57 | 1.71 | 0.09 | 0.36 | 0.05 | 0.36 | 0.42 | 5.34 |
| 93PI41003 | X724421 | 0.03 | 2.86 | 0.20 | 1.14 | 66.28 | 19.70 | 6.81 | 0.49 | 1.61 | 0.08 | 0.28 | 0.05 | 0.21 | 0.26 | 5.01 |
| 93PI41003 | X724422 | 0.04 | 3.18 | 0.21 | 1.04 | 64.87 | 20.88 | 7.02 | 0.50 | 1.51 | 0.07 | 0.30 | 0.05 | 0.15 | 0.18 | 5.20 |
| 93PI41003 | X724423 | 0.03 | 2.88 | 0.17 | 1.15 | 68.48 | 17.75 | 6.50 | 0.51 | 1.69 | 0.08 | 0.30 | 0.05 | 0.20 | 0.20 | 5.08 |
| 93PI41003 | X724611 | 0.04 | 3.28 | 0.25 | 1.64 | 71.09 | 15.28 | 4.78 | 0.64 | 1.73 | 0.08 | 0.39 | 0.05 | 0.31 | 0.45 | 6.29 |

Example 4

Cloning of *Brassica napus* FatB

Cloning of the *Brassica napus* Fat B gene was initiated by performing PCR with primers Fat B1 (5'-ATGAAGGTTAAACCAAACGCTCAGGC-3'; SEQ ID NO:8) and Fat B2 (5'-TGTTCTTCCTCTCACCACTTCAGC-3'; SEQ ID NO:9), respectively, using Westar genomic DNA as template and Taq polymerase (Qiagen). Each 50 µL reaction contained 0.5 µM primers, 1× Qiagen Taq polymerase buffer, 2.5U Taq polymerase, and 0.2 mM dNTPs. The target was amplified using the following cycling conditions: 1 cycle of 94° C. for 30 seconds; 5 cycles of 94° C. for 10 seconds, 58° C. for 30 seconds, and 72° C. for 1 min. 30 secs; 5 cycles of 94° C. for 10 seconds, 54° C. for 30 seconds, and 72° C. for 1 min. 30 secs; and 24 cycles of 94° C. for 10 seconds, 51° C. for 30 seconds, and 72° C. for 1 min. 45 secs. Aliquots of the PCR reactions were run on an agarose gel and selected bands were excised; DNA was eluted from the bands using the Qiagen Qiaquick kit. The DNA eluate was subjected to a 'polishing' reaction to facilitate T/A cloning and then TOPO® T/A® cloned using the TOPO® T/A® cloning kit (Invitrogen). Sequences were obtained for the clones then analyzed using BLAST to search for homology. One of the clones appeared to be a FatB.

PCR was repeated using Invitrogen Platinum® Pfx polymerase, its buffer, supplementary MgSO₄ at a final concentration of 2 mM, and IMC201 strain genomic DNA with cycling conditions as follows: 1 cycle of 94° C. for 2 minutes; 5 cycles of 94° C. for 10 seconds, 60° C. for 30 seconds, and 72° C. for 1 min. 20 secs; 5 cycles of 94° C. for 10 seconds, 57° C. for 30 seconds, and 72° C. for 1 min. 30 secs; and 24 cycles of 94° C. for 10 seconds, 54° C. for 30 seconds, and 72° C. for 1 min. 30 secs. The PCR product from this reaction also was Topo®/A® cloned using the Topo® T/A® cloning system (Invitrogen).

A number of the clones that were sequenced showed homology to Fat B (SEQ ID NOS:10, 11, 12, 13), with 4 distinct isoforms of the gene identified. To obtain sequence of the start and stop regions of each gene, a 'walking' procedure was employed utilizing GenomeWalker™ kits (Clontech), according to manufacturer protocols. Based on the sequence information from the walking procedure, primers corresponding to 5' UTR and 3'UTR or near-stop codon regions of the FatB genes were designed. PCR was performed using IMC201 genomic DNA as template and two sets of primers in 50 µL reactions containing 1× Platinum® Taq High Fidelity buffer; 2.5 U Platinum® Taq High Fidelity polymerase; 0.2 mM dNTPs; 0.5 µM primers; and 2 mM MgSO₄. Primers for the first reaction were 5'-CTTTGAACGCTCAGCTCCTCAGCC-3' (SEQ ID NO:14) and 5'-AAACGAACCAAAGAACCCATGTTTGC-3' (SEQ ID NO:15). Primers for the second reaction were 5'-CTTTGAAAGCTCATCTTCCTCGTC-3' (SEQ ID NO:16) and 5'-GGTTGCAAGGTAGCAGCAGGTACAG-3' (SEQ ID NO:17). The first reaction was performed under the following cycling conditions: 1 cycle of 94° C. for 2 minutes; 5 cycles of 94° C. for 10 seconds, 56° C. for 40 seconds, and 68° C. for 1 min. 30 secs; 30 cycles of 94° C. for 10 seconds, 53° C. for 30 seconds, and 68° C. for 2 min. The second reaction was performed under the following cycling conditions: 1 cycle of 95° C. for 2 minutes; 5 cycles of 94° C. for 10 seconds, 58° C. for 40 seconds, and 68° C. for 2 min; and 30 cycles of 94° C. for 10 seconds, 55° C. for 30 seconds, and 68° C. for 2 min. Both reaction sets produced bands with an expected size of ~1.6 Kb.

To clone the DNA, PCR reactions were performed using 1 cycle of 94° C. for 2 minutes, and 35 cycles of 94° C. for 10 seconds, 58° C. for 40 seconds, and 68° C. for 2 min. The resultant bands were gel purified and run over Qiagen Qiex II columns to purify the DNA from the agarose gel. The DNA was Topo®/A® cloned using the Invitrogen T/A® cloning system. The nucleotide sequences set forth in SEQ ID NOS: 18-21 represent full-length (or near full-length) Fat B isoforms 1, 2, 3, and 4, respectively.

FatB isoforms 5 and 6 were identified as follows. Primers 5'-ACAGTGGATGATGCTTGACTC-3' (SEQ ID NO:22) and 5'-TAGTAATATACCTGTAAGTGG-3' (SEQ ID NO:23) were designed based on FatB sequences from *B. napus* 01OB240 and used to amplify *B. napus* genomic DNA from IMC201. The resulting products were cloned and sequenced, and a new Fat B partial length isoform was identified. Sequence walking was performed with GenomeWalker™ kits (Clontech). Primers 5'-TACGATGTAGTGTCCCAAGTTGTTG-3' (SEQ ID NO:24) and 5'-TTTCTGTGGTGTCAGTGTGTCT-3' (SEQ ID NO:25) were designed based on the sequence obtained through genome walking and used to amplify a contiguous ORF region of the new FatB isoform. PCR products were cloned and sequenced to identify FatB isoforms 5 and 6 (SEQ ID NO:26 and SEQ ID NO:27). The six isoforms have 82 to 95% sequence identity as assessed with the ClustalW algorithm.

Example 5

Mutant FATB Genes

A population of *B. napus* IMC201 seeds was subjected to chemical mutagenesis. The typical fatty acid composition of field grown IMC201 is 3.6% C16:0, 1.8% C18:0, 76% C18:1, 12.5% C18:2, 3% C18:3, 0.7% C20:0, 1.5% C20:1, 0.3% C22:0, 0% C22:1, with total saturates of 6.4%. Prior to mutagenesis, IMC201 seeds were pre-imbibed in 700 gm seed lots by soaking for 15 min then draining for 5 min at room temperature. This was repeated four times to soften the seed coat. The pre-imbibed seed then were treated with 4 mM methyl N-nitrosoguanidine (MNNG) for three hours. Following the treatment with MNNG, seeds were drained of the mutagen and rinsed with water for one hour. After removing the water, the seeds were treated with 52.5 mM ethyl methanesulfonate (EMS) for sixteen hours. Follow the treatment with EMS, the seeds were drained of mutagen and rinsed with water for one and half hours. This dual mutagen treatment produced an $LD_{50}$ with the seed population.

Approximately 200,000 treated seeds were planted in standard greenhouse potting soil and placed into environmentally controlled greenhouse. The plants were grown under sixteen hours of day light. At maturity, M2 seed was harvested from the plants and bulked together. The M2 generation was planted and leaf samples from the early, post-cotyledon stage of development from 8 plants were pooled and DNA was extracted from leaves of these plants. The leaf harvest, pooling and DNA extraction was repeated for approximately 32,000 plants, and resulted in approximately forty 96-well blocks containing mutagenized B. napus IMC201 DNA. This grouping of mutagenized DNA is referred to below as the DNA mutagenesis library.

The DNA mutagenesis library was screened to identify stop-codon containing FatB mutants. In general, PCR primers were designed to amplify a region of each FatB isoform. The reaction products were analyzed using temperature gradient capillary electrophoresis on a REVEAL™ instrument (Transgenomics Inc.), which allows PCR reactions containing heterogeneous PCR products to be distinguished from reactions containing only homogeneous products, as would be the case if a single-nucleotide polymorphism (SNP) existed in genomic DNA from chemical mutagenesis and subsequent PCR amplification.

Individual seeds representing the primary hit of each M2 plant that was the source genomic DNA mix for this primary mutagenesis screen were sampled and genomic DNA was isolated in order to perform the isoform PCR. PCR reactions were performed using B. napus IMC201 genomic DNA in a 30 µL reaction containing 1× Platinum® Taq High Fidelity buffer; 2.0 U Platinum™ Taq High Fidelity polymerase; 0.2 mM dNTPs; 0.5 µM primers; and 2 mM $MgSO_4$. Cycling conditions were as follows: 1 cycle of 95° C. for 2 minutes followed by 34 cycles of 94° C. for 6 seconds, 64° C. for 40 seconds, and 68° C. for 40 seconds. PCR products were sequenced and the sequences were compared to the wild-type sequence for each isoform.

The sequence comparisons indicated that mutations had been generated and mutant plants obtained for each of isoforms 1, 2, 3 and 4. The mutant sequences are shown in SEQ ID NOS: 1-4. SEQ ID NO:1 contains the nucleotide sequence of isoform 1 having a mutation at position 154, changing the codon from CAG to TAG. SEQ ID NO:2 contains the nucleotide sequence of isoform 2 having a mutation at position 695, changing the codon from CAG to TAG. SEQ ID NO:3 contains the nucleotide sequence of isoform 3 having a mutation at position 276, changing the codon from TGG to TGA. SEQ ID NO:4 contains the nucleotide sequence of isoform 4 having a mutation at position 336, changing the codon from TGG to TGA.

Example 6

Brassica napus Plants Carrying Combinations of Mutant Brassica FatB Genes

Brassica napus plants carrying different combinations of mutants in different FatB isoforms were generated in order to determine the effect of the various mutant Brassica FatB alleles described in Example 5 on the fatty acid composition of Brassica napus seed oil. Parent plants, each carrying one or more mutations in a different isoform were crossed in various ways, progeny were screened by DNA sequence analysis to identify the mutation(s) present, followed by self-pollination and DNA sequence analysis to determine whether the mutations were present in the homozygous or heterozygous state.

Using this process, three Brassica plants were generated that carried mutant alleles of four FatB isoforms. Each of these plants was self pollinated, harvested and replanted in the greenhouse to create a population of 1,140 plants. All 1,140 plants were screened via DNA sequence analysis to determine whether the mutant alleles were present in the homozygous or heterozygous state at each of the FatB isoform loci. Progeny were identified that were homozygous for the following combinations of mutant FatB isoforms: FatB isoforms 1, 2 and 3; FatB isoforms 1, 2 and 4; FatB isoforms 2, 3 and 4; FatB isoforms 1, 3 and 4; and FatB isoforms 1, 2, 3 and 4.

Plants carrying combinations of mutant FatB isoforms were self pollinated and seeds were harvested. The resulting seeds were planted in growth chambers under two different temperature regimes, in order to assess the effect of the different combinations of mutant alleles on fatty acid composition. The IMC201 parent was used as a control in both temperature regimes.

The seeds were planted in Premier Pro-Mix BX potting soil (Premier Horticulture, Quebec, Canada) in four inch plastic pots. Planted seeds were watered and stratified at 5° C. for 5 days and germinated at 20° C. day temperature and 17° C. night temperature (20/17) in Conviron ATC60 controlled-environment growth chambers (Controlled Environments, Winnipeg, MB). Each gene combination was randomized and replicated 10 times in each of two separate growth chambers. At flowering, one chamber was reduced to a diurnal temperature cycle of 14° C. day temperature and 11° C. night temperature (14/11) while the other remained at 20/17. The temperature treatments were imposed to identify the effects of temperature on fatty acid composition. Plants were watered five times per week and fertilized bi-weekly using a 20:20:20 (NPK) liquid fertilizer at a rate of 150 ppm. Plants were bagged individually to ensure self pollination and genetic purity of the seed. Seeds from each plant was harvested individually at physiological seed maturity. All plants were analyzed using PCR based assays to confirm the presence of the FatB mutant alleles at the expected loci as well as the presence of mutant alleles of fatty acid desaturase genes (mFad3a, mFad3b and mFad2d) from the IMC201 pedigree.

IMC201 was selected from a cross of 91AE.318×IMC02. 91AE.318 is a sister or descendent of IMC129, which is described in U.S. Pat. No. 5,668,299. IMC02 was obtained from a cross of IMC01×Westar. See Example 3 of U.S. Pat. No. 5,750,827. IMC02 contains a mutation in both the fad3A and fad3B genes. The fad3A gene contains a C to T mutation at position 2565 from ATG in genomic DNA, resulting in the substitution of a cysteine for arginine at position 275 of the Fad3A protein. The fad3B gene contains a G to A mutation at position 3053 from ATG in genomic DNA, located in the exon-intron splice site recognition sequence.

A modified method for gas chromatograph determination of fatty acid profile per the American Oil Chemist's Society protocol (AOCS, 2009) was used for sample evaluation. Vials were placed in a Hewlett-Packard 5890 Series II gas chromatograph (Hewlett-Packard, Palo Alto, Calif.) equipped with a fused silica capillary column (5 m×0.180 mm and 0.20 µm film thickness) packed with a polyethylene glycol based DB-Wax® for liquid phase separation (J&W Scientific, Folsom, Calif.). Hydrogen ($H^2$) was used as the carrier gas at a flow rate of 2.5 mL/min and the column temperature was isothermal at 200° C. Seed from each plant was tested via this method in replicates of three.

Fatty acid data from plants grown under the different temperature regimes was analyzed in two ways. First, data was analyzed separately as different environments and then it was pooled and analyzed across environments. Data was analyzed in SAS (SAS Institute, 2003) using proc glm to estimate differences in mean fatty acid values. Table 8 contains the genotype, population size, mean value and standard deviation of palmitic, stearic and total saturated fatty acid of seeds produced by plants carrying various combinations of mutant FatB alleles grown in two environmental growth chambers set at different diurnal temperature regimes (20° C. day/17° C. night; 14° C. day/11° C. night) as discussed above. Genotypes preceded by Iso are mutant allele combinations and the numbers thereafter indicate the specific locus. Means with different letters are significantly different as determined by a Student-Newman-Keuls mean separation test.

environments. Therefore, the number of copies of this allele (0, 1 or 2) was included as a covariate in ANOVA mean separation tests. Significant differences were discovered for mean values of seed palmitic and total saturated fatty acid content in analyses using data pooled across environments (Table 9).

All plants carrying mutant FatB alleles showed statistically significant reductions in seed palmitic acid relative to the IMC201 control with the largest reduction in plants carrying all 4 mutant alleles. Significant reductions in total saturated fatty acid were found in seeds produced by plants carrying mutant alleles 1, 2 and 3 (i.e., Iso 123 in Tables 9 and 10) as well as Iso 1234.

Statistically significant differences were discovered for mean stearic acid content when seeds produced in the different chambers under different temperature treatments were analyzed separately (Table 10, means with different letters are significantly different as determined by a Student-Newman-Keuls mean separation test). In the 20/17 environment, Iso 123, Iso 124 and Iso 1234 all showed significant reductions in stearic acid. Only Iso 1234 showed this reduction in the 14/11 environment. Reductions in total saturated fatty

TABLE 8

| Across Environments | | | | | | | | | |
|---|---|---|---|---|---|---|---|---|---|
| Genotype | N | C16:0 | s.d. | Genotype | n | C18:0 | s.d. | Genotype | n | Total Sats | s.d. |

| Genotype | N | C16:0 | s.d. | Genotype | n | C18:0 | s.d. | Genotype | n | Total Sats | s.d. |
|---|---|---|---|---|---|---|---|---|---|---|---|
| IMC201 | 16 | 3.795a | 0.424 | Iso 234 | 16 | 1.971a | 0.880 | IMC201 | 16 | 6.757a | 0.925 |
| Iso234 | 16 | 3.273b | 0.368 | IMC201 | 16 | 1.831ab | 0.373 | Iso234 | 16 | 6.542a | 1.549 |
| Iso124 | 9 | 3.135bc | 0.109 | Iso124 | 9 | 1.81ab | 0.195 | Iso124 | 9 | 6.168ab | 0.338 |
| Iso123 | 8 | 2.959c | 0.174 | Iso123 | 8 | 1.628ab | 0.227 | Iso123 | 8 | 5.719bc | 0.376 |
| Iso1234 | 17 | 2.721d | 0.240 | Iso1234 | 17 | 1.520b | 0.310 | Iso1234 | 17 | 5.412c | 0.729 |

PCR screening showed that the mFad2d mutant allele from IMC129 was segregating in all of the FatB mutant combinations. It was found to be absent or heterozygous in 70% of the individuals screened. The effect of this allele was statistically significant for palmitic, stearic and total saturated fatty acid contents (F=11.17, p=0.0011; F=4.43, p=0.0376; F=6.55, p=0.0118, respectively) in analyses comparing means across acid content for Iso 123, Iso 124 and Iso 1234 were significant in the 20/17 environment and all mutant allele combinations showed significant reductions in the 14/11 environment (Tables 9 and 10). Again, plants carrying all forms of the mutant allele combinations showed significant reductions in palmitic acid when data from environments was analyzed separately.

TABLE 9

| Genotype | N | C16:0 | s.d. | Genotype | N | C18:0 | s.d. | Genotype | n | Total Sats | s.d. |
|---|---|---|---|---|---|---|---|---|---|---|---|
| 20/17 Environment | | | | | | | | | | | |
| IMC201 | 8 | 3.971a | 0.292 | Iso 234 | 7 | 2.771a | 0.807 | Iso234 | 7 | 8.098a | 1.116 |
| Iso234 | 7 | 3.614b | 0.106 | IMC201 | 8 | 2.158b | 0.203 | IMC201 | 8 | 7.465b | 0.244 |
| Iso124 | 9 | 3.135c | 0.109 | Iso124 | 9 | 1.810c | 0.195 | Iso124 | 9 | 6.168c | 0.338 |
| Iso123 | 4 | 2.979cd | 0.159 | Iso123 | 4 | 1.806c | 0.111 | Iso123 | 4 | 5.988c | 0.256 |
| Iso1234 | 9 | 2.916d | 0.102 | Iso1234 | 9 | 1.749c | 0.187 | Iso1234 | 9 | 5.965c | 0.390 |
| 14/11 Environment | | | | | | | | | | | |
| IMC201 | 8 | 3.618a | 0.471 | IMC201 | 8 | 1.504a | 0.195 | IMC201 | 8 | 6.050a | 0.826 |
| Iso234 | 9 | 3.007b | 0.317 | Iso123 | 4 | 1.451a | 0.156 | Iso123 | 4 | 5.450b | 0.268 |
| Iso123 | 4 | 2.939b | 0.210 | Iso234 | 9 | 1.349ab | 0.082 | Iso234 | 9 | 5.331b | 0.305 |
| Iso1234 | 8 | 2.501c | 0.119 | Iso1234 | 8 | 1.262b | 0.197 | Iso1234 | 8 | 4.791c | 0.463 |

The mean content of the three fatty acids reported here were significantly different between the environments (C16:0 F=59.59, p<0.0001; C18:0 F=83.42, p<0.0001; Total Sats F=122.02, p<0.0001). The data indicate that a low temperature environment reduces the amount of these saturated fatty acids in the seed oil.

TABLE 10

Fatty Acid Profile of IMC201 and Plants With Mutant FatB Alleles

| Genotype | Environment | 14:0 | 16:0 | 16:1 | 18:0 | 18:1 | 18:2 | 18:3 | 20:0 | 20:1 | 20:2 | 22:0 | 22:1 | 24:0 | 24:1 | Total Sats |
|---|---|---|---|---|---|---|---|---|---|---|---|---|---|---|---|---|
| IMC201 | High (20/17) | 0.05 | 4.26 | 0.20 | 2.06 | 78.16 | 10.15 | 2.02 | 0.84 | 1.32 | 0.05 | 0.44 | 0.02 | 0.25 | 0.18 | 7.90 |
| IMC201 | High (20/17) | 0.05 | 4.06 | 0.20 | 2.21 | 75.83 | 12.34 | 2.49 | 0.78 | 1.25 | 0.06 | 0.36 | 0.02 | 0.19 | 0.15 | 7.65 |
| IMC201 | High (20/17) | 0.05 | 3.79 | 0.18 | 2.34 | 77.38 | 10.98 | 2.25 | 0.84 | 1.30 | 0.06 | 0.40 | 0.02 | 0.23 | 0.20 | 7.64 |
| IMC201 | High (20/17) | 0.05 | 3.99 | 0.19 | 2.16 | 76.33 | 12.22 | 2.27 | 0.77 | 1.24 | 0.05 | 0.36 | 0.02 | 0.17 | 0.18 | 7.50 |
| IMC201 | High (20/17) | 0.05 | 4.30 | 0.22 | 1.86 | 77.13 | 11.37 | 2.37 | 0.69 | 1.23 | 0.06 | 0.36 | 0.03 | 0.17 | 0.17 | 7.43 |
| IMC201 | High (20/17) | 0.05 | 4.34 | 0.22 | 1.84 | 76.58 | 11.93 | 2.43 | 0.68 | 1.20 | 0.06 | 0.34 | 0.02 | 0.16 | 0.17 | 7.40 |
| IMC201 | High (20/17) | 0.05 | 4.03 | 0.19 | 2.05 | 76.20 | 12.56 | 2.31 | 0.69 | 1.21 | 0.06 | 0.34 | 0.02 | 0.15 | 0.15 | 7.30 |
| IMC201 | High (20/17) | 0.05 | 3.90 | 0.19 | 2.16 | 75.80 | 12.94 | 2.42 | 0.68 | 1.22 | 0.06 | 0.30 | 0.02 | 0.15 | 0.13 | 7.22 |
| IMC201 | High (20/17) | 0.03 | 3.41 | 0.13 | 2.46 | 76.72 | 12.12 | 2.37 | 0.72 | 1.35 | 0.07 | 0.30 | 0.01 | 0.18 | 0.12 | 7.10 |
| IMC201 | Low (14/11) | 0.06 | 4.02 | 0.23 | 1.47 | 74.65 | 13.94 | 3.03 | 0.58 | 1.33 | 0.06 | 0.33 | 0.03 | 0.13 | 0.15 | 6.58 |
| IMC201 | Low (14/11) | 0.05 | 3.97 | 0.22 | 1.49 | 75.43 | 13.43 | 2.74 | 0.58 | 1.36 | 0.06 | 0.34 | 0.03 | 0.11 | 0.18 | 6.54 |
| IMC201 | Low (14/11) | 0.05 | 3.76 | 0.21 | 1.63 | 76.15 | 12.63 | 2.98 | 0.61 | 1.27 | 0.06 | 0.34 | 0.04 | 0.11 | 0.16 | 6.51 |
| IMC201 | Low (14/11) | 0.04 | 3.84 | 0.21 | 1.42 | 75.88 | 12.93 | 2.93 | 0.57 | 1.43 | 0.07 | 0.36 | 0.02 | 0.12 | 0.19 | 6.35 |
| IMC201 | Low (14/11) | 0.04 | 3.66 | 0.20 | 1.59 | 75.94 | 12.96 | 2.98 | 0.55 | 1.32 | 0.08 | 0.34 | 0.05 | 0.10 | 0.20 | 6.28 |
| IMC201 | Low (14/11) | 0.05 | 3.67 | 0.20 | 1.62 | 76.61 | 12.52 | 2.96 | 0.37 | 1.32 | 0.05 | 0.31 | 0.03 | 0.11 | 0.20 | 6.13 |
| IMC201 | Low (14/11) | 0.03 | 3.49 | 0.13 | 1.73 | 74.49 | 14.29 | 3.38 | 0.40 | 1.61 | 0.04 | 0.21 | 0.02 | 0.06 | 0.13 | 5.92 |
| IMC201 | Low (14/11) | 0.02 | 2.53 | 0.16 | 1.09 | 75.76 | 15.24 | 3.20 | 0.14 | 1.29 | 0.08 | 0.24 | 0.02 | 0.07 | 0.16 | 4.08 |
| Iso123 | High (20/17) | 0.04 | 3.20 | 0.26 | 1.82 | 76.55 | 12.40 | 3.05 | 0.68 | 1.21 | 0.06 | 0.35 | 0.02 | 0.17 | 0.18 | 6.26 |
| Iso123 | High (20/17) | 0.03 | 2.85 | 0.27 | 1.97 | 78.31 | 10.98 | 2.78 | 0.76 | 1.17 | 0.04 | 0.38 | 0.04 | 0.25 | 0.15 | 6.25 |
| Iso123 | High (20/17) | 0.04 | 2.96 | 0.24 | 1.95 | 77.09 | 12.09 | 3.06 | 0.68 | 1.15 | 0.06 | 0.33 | 0.02 | 0.16 | 0.18 | 6.10 |
| Iso123 | High (20/17) | 0.04 | 2.82 | 0.32 | 1.75 | 74.68 | 14.64 | 2.96 | 0.69 | 1.17 | 0.05 | 0.38 | 0.01 | 0.25 | 0.26 | 5.92 |
| Iso123 | High (20/17) | 0.04 | 2.94 | 0.27 | 1.70 | 76.32 | 13.20 | 3.21 | 0.57 | 1.11 | 0.06 | 0.29 | 0.01 | 0.13 | 0.16 | 5.67 |
| Iso123 | Low (14/11) | 0.04 | 3.19 | 0.27 | 1.50 | 72.50 | 15.95 | 3.75 | 0.59 | 1.41 | 0.07 | 0.37 | 0.02 | 0.12 | 0.23 | 5.80 |
| Iso123 | Low (14/11) | 0.05 | 2.89 | 0.30 | 1.64 | 75.34 | 13.62 | 3.80 | 0.52 | 1.12 | 0.06 | 0.30 | 0.04 | 0.11 | 0.21 | 5.51 |
| Iso123 | Low (14/11) | 0.03 | 3.00 | 0.24 | 1.29 | 75.38 | 13.96 | 3.40 | 0.53 | 1.41 | 0.06 | 0.35 | 0.03 | 0.11 | 0.21 | 5.32 |
| Iso123 | Low (14/11) | 0.03 | 2.68 | 0.25 | 1.37 | 76.24 | 12.90 | 3.65 | 0.59 | 1.43 | 0.06 | 0.38 | 0.02 | 0.14 | 0.26 | 5.18 |
| Iso124 | High (20/17) | 0.04 | 3.23 | 0.28 | 2.13 | 72.73 | 16.29 | 2.74 | 0.72 | 1.07 | 0.05 | 0.37 | 0.02 | 0.16 | 0.16 | 6.65 |
| Iso124 | High (20/17) | 0.04 | 3.17 | 0.27 | 2.01 | 72.62 | 16.76 | 2.55 | 0.71 | 1.09 | 0.05 | 0.37 | 0.02 | 0.17 | 0.16 | 6.48 |
| Iso124 | High (20/17) | 0.04 | 3.12 | 0.24 | 1.87 | 78.55 | 10.92 | 2.43 | 0.74 | 1.24 | 0.06 | 0.39 | 0.02 | 0.21 | 0.17 | 6.37 |
| Iso124 | High (20/17) | 0.04 | 3.19 | 0.25 | 1.82 | 71.84 | 17.19 | 2.96 | 0.67 | 1.15 | 0.06 | 0.37 | 0.02 | 0.19 | 0.26 | 6.27 |
| Iso124 | High (20/17) | 0.05 | 3.15 | 0.32 | 1.82 | 77.52 | 11.88 | 2.65 | 0.68 | 1.18 | 0.06 | 0.36 | 0.00 | 0.18 | 0.16 | 6.22 |
| Iso124 | High (20/17) | 0.04 | 3.20 | 0.28 | 1.89 | 67.27 | 22.04 | 2.95 | 0.62 | 1.02 | 0.06 | 0.31 | 0.01 | 0.13 | 0.17 | 6.20 |
| Iso124 | High (20/17) | 0.04 | 3.24 | 0.26 | 1.57 | 66.46 | 22.91 | 2.93 | 0.62 | 1.15 | 0.07 | 0.35 | 0.03 | 0.14 | 0.23 | 5.97 |
| Iso124 | High (20/17) | 0.04 | 2.98 | 0.22 | 1.59 | 78.96 | 11.00 | 2.76 | 0.61 | 1.15 | 0.05 | 0.34 | 0.02 | 0.15 | 0.15 | 5.70 |
| Iso124 | High (20/17) | 0.04 | 2.93 | 0.24 | 1.60 | 78.65 | 11.12 | 2.87 | 0.62 | 1.21 | 0.05 | 0.33 | 0.02 | 0.15 | 0.18 | 5.65 |
| Iso124 | Low (14/11) | 0.04 | 2.84 | 0.31 | 1.54 | 73.84 | 15.65 | 3.51 | 0.36 | 1.16 | 0.06 | 0.35 | 0.02 | 0.10 | 0.22 | 5.23 |
| Iso234 | High (20/17) | 0.05 | 3.64 | 0.25 | 3.72 | 69.54 | 16.12 | 2.79 | 1.30 | 1.13 | 0.07 | 0.63 | 0.02 | 0.42 | 0.31 | 9.78 |
| Iso234 | High (20/17) | 0.05 | 3.39 | 0.22 | 3.70 | 67.48 | 18.73 | 3.14 | 1.13 | 1.06 | 0.06 | 0.50 | 0.03 | 0.27 | 0.24 | 9.04 |
| Iso234 | High (20/17) | 0.05 | 3.60 | 0.22 | 3.26 | 70.34 | 17.05 | 2.52 | 1.04 | 1.03 | 0.06 | 0.45 | 0.01 | 0.21 | 0.17 | 8.60 |
| Iso234 | High (20/17) | 0.05 | 3.69 | 0.25 | 2.64 | 70.29 | 17.18 | 3.07 | 0.85 | 1.07 | 0.06 | 0.39 | 0.01 | 0.26 | 0.18 | 7.88 |
| Iso234 | High (20/17) | 0.05 | 3.69 | 0.23 | 2.37 | 72.38 | 15.60 | 2.50 | 0.92 | 1.20 | 0.07 | 0.49 | 0.02 | 0.27 | 0.22 | 7.79 |
| Iso234 | High (20/17) | 0.05 | 3.82 | 0.31 | 1.76 | 74.59 | 14.16 | 2.74 | 0.64 | 1.15 | 0.07 | 0.34 | 0.01 | 0.25 | 0.12 | 6.85 |
| Iso234 | High (20/17) | 0.05 | 3.70 | 0.26 | 1.76 | 76.47 | 12.22 | 2.70 | 0.70 | 1.26 | 0.06 | 0.37 | 0.03 | 0.23 | 0.19 | 6.81 |
| Iso234 | High (20/17) | 0.05 | 3.59 | 0.25 | 1.94 | 70.65 | 18.05 | 2.81 | 0.68 | 1.13 | 0.06 | 0.34 | 0.04 | 0.18 | 0.21 | 6.79 |
| Iso234 | Low (14/11) | 0.06 | 3.71 | 0.32 | 1.27 | 66.07 | 21.66 | 4.24 | 0.35 | 1.32 | 0.07 | 0.43 | 0.06 | 0.16 | 0.29 | 5.98 |
| Iso234 | Low (14/11) | 0.03 | 3.18 | 0.32 | 1.40 | 66.38 | 22.07 | 3.79 | 0.55 | 1.29 | 0.10 | 0.39 | 0.06 | 0.13 | 0.32 | 5.68 |
| Iso234 | Low (14/11) | 0.03 | 3.28 | 0.29 | 1.40 | 66.93 | 23.28 | 2.44 | 0.46 | 1.13 | 0.06 | 0.29 | 0.04 | 0.12 | 0.24 | 5.59 |
| Iso234 | Low (14/11) | 0.04 | 3.13 | 0.28 | 1.43 | 67.90 | 21.10 | 3.53 | 0.52 | 1.30 | 0.08 | 0.34 | 0.02 | 0.11 | 0.23 | 5.57 |
| Iso234 | Low (14/11) | 0.04 | 3.05 | 0.27 | 1.30 | 68.17 | 20.89 | 3.63 | 0.50 | 1.33 | 0.07 | 0.35 | 0.04 | 0.12 | 0.24 | 5.36 |
| Iso234 | Low (14/11) | 0.05 | 3.12 | 0.29 | 1.30 | 66.56 | 22.26 | 3.88 | 0.35 | 1.30 | 0.10 | 0.35 | 0.03 | 0.14 | 0.26 | 5.30 |
| Iso234 | Low (14/11) | 0.02 | 3.12 | 0.30 | 1.33 | 69.56 | 20.66 | 2.59 | 0.33 | 1.28 | 0.08 | 0.34 | 0.04 | 0.11 | 0.24 | 5.25 |
| Iso234 | Low (14/11) | 0.04 | 2.74 | 0.27 | 1.45 | 76.56 | 12.91 | 3.53 | 0.49 | 1.25 | 0.06 | 0.32 | 0.04 | 0.11 | 0.21 | 5.15 |
| Iso234 | Low (14/11) | 0.04 | 2.93 | 0.25 | 1.18 | 70.80 | 18.54 | 3.58 | 0.49 | 1.40 | 0.07 | 0.34 | 0.02 | 0.11 | 0.26 | 5.09 |
| Iso234 | Low (14/11) | 0.03 | 2.52 | 0.38 | 1.35 | 72.27 | 16.85 | 3.81 | 0.54 | 1.30 | 0.06 | 0.40 | 0.00 | 0.15 | 0.33 | 4.99 |
| Iso1234 | High (20/17) | 0.04 | 3.07 | 0.26 | 2.09 | 69.61 | 18.91 | 2.87 | 0.88 | 1.18 | 0.07 | 0.52 | 0.03 | 0.23 | 0.23 | 6.84 |
| Iso1234 | High (20/17) | 0.04 | 2.90 | 0.26 | 1.92 | 68.36 | 20.89 | 3.05 | 0.72 | 1.06 | 0.06 | 0.37 | 0.00 | 0.20 | 0.18 | 6.15 |
| Iso1234 | High (20/17) | 0.04 | 2.92 | 0.26 | 1.75 | 73.39 | 15.92 | 2.90 | 0.75 | 1.17 | 0.06 | 0.42 | 0.03 | 0.20 | 0.21 | 6.07 |
| Iso1234 | High (20/17) | 0.04 | 2.87 | 0.28 | 1.83 | 71.68 | 17.50 | 3.11 | 0.72 | 1.11 | 0.06 | 0.37 | 0.03 | 0.19 | 0.22 | 6.02 |
| Iso1234 | High (20/17) | 0.04 | 3.01 | 0.26 | 1.54 | 71.11 | 18.51 | 2.66 | 0.71 | 1.19 | 0.07 | 0.44 | 0.03 | 0.20 | 0.23 | 5.94 |
| Iso1234 | High (20/17) | 0.04 | 3.01 | 0.29 | 1.57 | 70.56 | 18.63 | 3.40 | 0.62 | 1.12 | 0.06 | 0.34 | 0.02 | 0.16 | 0.19 | 5.74 |
| Iso1234 | High (20/17) | 0.04 | 2.79 | 0.27 | 1.80 | 70.89 | 18.95 | 2.88 | 0.63 | 1.06 | 0.06 | 0.31 | 0.02 | 0.15 | 0.15 | 5.74 |
| Iso1234 | High (20/17) | 0.04 | 2.77 | 0.24 | 1.71 | 72.23 | 17.53 | 2.90 | 0.66 | 1.12 | 0.07 | 0.35 | 0.01 | 0.19 | 0.18 | 5.72 |
| Iso1234 | High (20/17) | 0.04 | 2.89 | 0.28 | 1.53 | 67.27 | 22.56 | 3.11 | 0.57 | 1.03 | 0.07 | 0.31 | 0.01 | 0.14 | 0.19 | 5.47 |
| Iso1234 | Low (14/11) | 0.04 | 2.61 | 0.29 | 1.36 | 68.44 | 20.55 | 3.93 | 0.63 | 1.24 | 0.08 | 0.46 | 0.03 | 0.14 | 0.20 | 5.24 |
| Iso1234 | Low (14/11) | 0.02 | 2.51 | 0.27 | 1.42 | 69.76 | 19.44 | 3.75 | 0.64 | 1.27 | 0.10 | 0.44 | 0.02 | 0.15 | 0.23 | 5.17 |
| Iso1234 | Low (14/11) | 0.03 | 2.54 | 0.26 | 1.33 | 64.33 | 25.15 | 3.73 | 0.56 | 1.22 | 0.09 | 0.40 | 0.01 | 0.12 | 0.24 | 4.97 |
| Iso1234 | Low (14/11) | 0.04 | 2.68 | 0.27 | 1.36 | 70.70 | 18.79 | 3.82 | 0.38 | 1.19 | 0.05 | 0.38 | 0.01 | 0.12 | 0.21 | 4.96 |
| Iso1234 | Low (14/11) | 0.03 | 2.47 | 0.29 | 1.31 | 68.06 | 21.43 | 3.63 | 0.59 | 1.35 | 0.07 | 0.40 | 0.02 | 0.11 | 0.27 | 4.89 |
| Iso1234 | Low (14/11) | 0.03 | 2.53 | 0.29 | 1.29 | 65.90 | 23.37 | 3.93 | 0.53 | 1.30 | 0.08 | 0.39 | 0.02 | 0.10 | 0.24 | 4.86 |
| Iso1234 | Low (14/11) | 0.03 | 2.39 | 0.27 | 1.24 | 70.56 | 18.96 | 3.64 | 0.59 | 1.38 | 0.08 | 0.43 | 0.03 | 0.15 | 0.26 | 4.82 |

TABLE 10-continued

Fatty Acid Profile of IMC201 and Plants With Mutant FatB Alleles

| Genotype | Environment | 14:0 | 16:0 | 16:1 | 18:0 | 18:1 | 18:2 | 18:3 | 20:0 | 20:1 | 20:2 | 22:0 | 22:1 | 24:0 | 24:1 | Total Sats |
|---|---|---|---|---|---|---|---|---|---|---|---|---|---|---|---|---|
| Iso1234 | Low (14/11) | 0.04 | 2.48 | 0.28 | 1.34 | 71.51 | 18.58 | 3.57 | 0.34 | 1.14 | 0.08 | 0.34 | 0.02 | 0.10 | 0.19 | 4.63 |
| Iso1234 | Low (14/11) | 0.02 | 2.27 | 0.14 | 0.76 | 74.15 | 13.60 | 6.46 | 0.32 | 1.67 | 0.12 | 0.23 | 0.04 | 0.07 | 0.16 | 3.66 |

Example 7

Brassica Plant Lines 1764, 1975, and 2650

Lines 1764, 1975, and 2650 were selected from the mutagenized population of IMC201 seeds of Example 5 as follows. Three thousand bulk $M_2$ generation seeds were planted. Upon maturity, $M_3$ seed (2500 individuals) was harvested from 2500 $M_2$ plants and analyzed via GC. Table 11 provides the fatty acid profile of seed from three lines identified as having a low total saturates content in seed oil: 1764, 1975, and 2650. M3 seeds of 1764, 1975, and 2650 were planted (100 per line) and the resulting plants were self pollinated. $M_4$ seeds were harvested from the plants and analyzed via GC (see Table 12).

TABLE 11

Fatty acid composition of $M_3$ generation seed from mutant lines exhibiting reduced saturated fatty acid content

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| 1764 | 0.05 | 3.30 | 0.31 | 1.65 | 76.30 | 13.40 | 2.00 | 0.668 | 1.46 | 0.06 | 0.38 | 0.02 | 0.28 | 0.15 | 6.32 |
| 1975 | 0.03 | 3.19 | 0.22 | 1.35 | 75.51 | 14.21 | 2.19 | 0.59 | 1.77 | 0.10 | 0.43 | 0.00 | 0.23 | 0.19 | 5.82 |
| 2650 | 0.04 | 3.00 | 0.12 | 3.79 | 77.77 | 8.59 | 2.056 | 1.42 | 1.68 | 0.08 | 0.74 | 0.02 | 0.45 | 0.26 | 9.44 |

TABLE 12

Fatty acid composition of $M_4$ generation seed from three mutant lines exhibiting reduced saturated fatty acid content

| Line | C140 | C160 | C161 | C180 | C181 | C182 | C183 | C200 | C201 | C202 | C220 | C221 | C240 | C241 | Total sat |
|---|---|---|---|---|---|---|---|---|---|---|---|---|---|---|---|
| 1764-06 | 0.05 | 3.06 | 0.34 | 1.94 | 76.89 | 12.57 | 1.99 | 0.70 | 1.34 | 0.05 | 0.39 | 0.00 | 0.23 | 0.45 | 6.37 |
| 1764-35 | 0.04 | 3.54 | 0.47 | 1.64 | 74.09 | 15.38 | 2.04 | 0.59 | 1.32 | 0.05 | 0.32 | 0.00 | 0.19 | 0.34 | 6.31 |
| 1764-43 | 0.04 | 3.06 | 0.32 | 1.88 | 75.24 | 14.26 | 1.86 | 0.75 | 1.58 | 0.07 | 0.45 | 0.03 | 0.28 | 0.18 | 6.46 |
| 1764-59 | 0.05 | 3.33 | 0.38 | 1.57 | 74.92 | 14.56 | 2.21 | 0.57 | 1.33 | 0.05 | 0.32 | 0.03 | 0.19 | 0.49 | 6.02 |
| 1764-91 | 0.05 | 3.11 | 0.34 | 1.77 | 75.83 | 13.70 | 2.15 | 0.67 | 1.37 | 0.05 | 0.38 | 0.02 | 0.24 | 0.32 | 6.21 |
| 1764-92 | 0.04 | 3.00 | 0.30 | 2.07 | 76.75 | 12.79 | 2.11 | 0.74 | 1.40 | 0.05 | 0.40 | 0.00 | 0.22 | 0.13 | 6.47 |
| 1764-95 | 0.06 | 3.38 | 0.40 | 1.62 | 74.11 | 15.17 | 2.18 | 0.63 | 1.36 | 0.06 | 0.37 | 0.03 | 0.22 | 0.43 | 6.27 |
| 1975-01 | 0.05 | 3.31 | 0.23 | 1.52 | 73.60 | 15.79 | 2.17 | 0.62 | 1.51 | 0.08 | 0.40 | 0.03 | 0.17 | 0.51 | 6.07 |
| 1975-04 | 0.02 | 3.04 | 0.16 | 1.74 | 77.28 | 12.64 | 2.08 | 0.66 | 1.54 | 0.06 | 0.36 | 0.00 | 0.17 | 0.24 | 6.00 |
| 1975-32 | 0.03 | 3.54 | 0.22 | 1.52 | 73.89 | 15.44 | 2.35 | 0.59 | 1.55 | 0.09 | 0.34 | 0.00 | 0.18 | 0.26 | 6.20 |
| 1975-65 | 0.03 | 3.18 | 0.16 | 1.71 | 75.16 | 14.26 | 2.22 | 0.63 | 1.64 | 0.09 | 0.36 | 0.00 | 0.16 | 0.39 | 6.07 |
| 1975-76 | 0.05 | 3.52 | 0.19 | 1.48 | 73.18 | 16.04 | 2.37 | 0.62 | 1.63 | 0.09 | 0.39 | 0.03 | 0.23 | 0.19 | 6.28 |
| 1975-84 | 0.04 | 3.12 | 0.14 | 1.68 | 75.57 | 14.07 | 2.35 | 0.64 | 1.61 | 0.09 | 0.35 | 0.00 | 0.20 | 0.12 | 6.03 |
| 1975-90 | 0.04 | 3.34 | 0.23 | 1.40 | 72.21 | 17.44 | 2.25 | 0.58 | 1.70 | 0.11 | 0.35 | 0.00 | 0.20 | 0.16 | 5.92 |
| 1975-96 | 0.04 | 3.13 | 0.17 | 1.99 | 76.43 | 12.99 | 2.05 | 0.76 | 1.60 | 0.07 | 0.40 | 0.00 | 0.23 | 0.13 | 6.55 |
| 1975-99 | 0.04 | 3.13 | 0.20 | 1.83 | 74.80 | 14.34 | 2.15 | 0.72 | 1.68 | 0.08 | 0.43 | 0.04 | 0.21 | 0.35 | 6.37 |
| 2650-20 | 0.06 | 2.81 | 0.13 | 4.08 | 74.24 | 11.71 | 2.29 | 1.38 | 1.84 | 0.11 | 0.62 | 0.05 | 0.38 | 0.31 | 9.32 |
| 2650-36 | 0.05 | 2.93 | 0.14 | 3.63 | 74.55 | 11.95 | 2.58 | 1.20 | 1.64 | 0.09 | 0.55 | 0.00 | 0.28 | 0.40 | 8.64 |
| 2650-45 | 0.06 | 3.02 | 0.14 | 3.74 | 75.16 | 11.27 | 2.49 | 1.19 | 1.58 | 0.08 | 0.51 | 0.00 | 0.26 | 0.52 | 8.77 |
| IMC02-01 | 0.06 | 3.73 | 0.21 | 2.96 | 70.35 | 18.37 | 1.30 | 0.98 | 1.15 | 0.05 | 0.44 | 0.01 | 0.26 | 0.13 | 8.43 |
| IMC02-02 | 0.05 | 3.64 | 0.23 | 2.85 | 70.86 | 17.82 | 1.28 | 0.98 | 1.21 | 0.05 | 0.48 | 0.02 | 0.29 | 0.26 | 8.27 |
| IMC02-03 | 0.05 | 3.66 | 0.21 | 2.90 | 69.84 | 18.96 | 1.32 | 0.94 | 1.15 | 0.05 | 0.42 | 0.02 | 0.27 | 0.21 | 8.24 |
| IMC02-04 | 0.05 | 3.62 | 0.23 | 3.06 | 68.94 | 19.37 | 1.38 | 1.01 | 1.20 | 0.06 | 0.49 | 0.00 | 0.31 | 0.28 | 8.54 |
| IMC02-05 | 0.04 | 3.62 | 0.24 | 3.13 | 69.27 | 19.33 | 1.34 | 0.96 | 1.13 | 0.06 | 0.41 | 0.01 | 0.25 | 0.20 | 8.42 |
| IMC02-06 | 0.05 | 3.87 | 0.25 | 3.74 | 70.11 | 17.17 | 1.40 | 1.21 | 1.14 | 0.06 | 0.58 | 0.00 | 0.34 | 0.09 | 9.79 |
| IMC02-07 | 0.06 | 3.75 | 0.27 | 2.89 | 66.48 | 22.22 | 1.34 | 0.89 | 1.11 | 0.05 | 0.40 | 0.00 | 0.23 | 0.29 | 8.23 |
| IMC02-08 | 0.06 | 3.71 | 0.25 | 2.83 | 69.87 | 18.87 | 1.25 | 0.95 | 1.16 | 0.05 | 0.43 | 0.00 | 0.27 | 0.30 | 8.26 |
| IMC02-09 | 0.07 | 4.51 | 0.35 | 3.83 | 65.22 | 20.57 | 1.96 | 1.20 | 1.03 | 0.00 | 0.57 | 0.00 | 0.37 | 0.34 | 10.53 |
| IMC02-10 | 0.05 | 3.66 | 0.25 | 2.77 | 68.23 | 20.84 | 1.27 | 0.90 | 1.17 | 0.05 | 0.41 | 0.00 | 0.25 | 0.16 | 8.03 |
| IMC02-11 | 0.05 | 3.79 | 0.23 | 2.95 | 68.43 | 20.15 | 1.32 | 0.98 | 1.15 | 0.06 | 0.46 | 0.00 | 0.29 | 0.13 | 8.52 |
| IMC02-12 | 0.06 | 3.72 | 0.25 | 2.78 | 68.35 | 20.50 | 1.30 | 0.90 | 1.15 | 0.05 | 0.42 | 0.00 | 0.26 | 0.25 | 8.14 |
| IMC02-13 | 0.08 | 3.92 | 0.25 | 2.92 | 67.17 | 21.30 | 1.43 | 0.93 | 1.11 | 0.06 | 0.42 | 0.00 | 0.30 | 0.12 | 8.56 |
| IMC02-14 | 0.05 | 3.64 | 0.23 | 3.09 | 71.73 | 16.73 | 1.36 | 1.05 | 1.19 | 0.05 | 0.51 | 0.00 | 0.28 | 0.09 | 8.62 |
| IMC02-15 | 0.06 | 3.73 | 0.25 | 2.99 | 69.14 | 19.49 | 1.23 | 0.99 | 1.15 | 0.05 | 0.45 | 0.00 | 0.29 | 0.17 | 8.51 |
| IMC02-16 | 0.06 | 3.76 | 0.24 | 2.81 | 69.05 | 19.89 | 1.21 | 0.94 | 1.17 | 0.05 | 0.43 | 0.00 | 0.27 | 0.14 | 8.25 |
| IMC02-17 | 0.05 | 3.63 | 0.25 | 2.61 | 67.52 | 21.91 | 1.33 | 0.83 | 1.12 | 0.06 | 0.39 | 0.00 | 0.21 | 0.10 | 7.72 |
| IMC02-18 | 0.05 | 3.66 | 0.22 | 3.19 | 71.15 | 17.32 | 1.25 | 1.06 | 1.16 | 0.05 | 0.51 | 0.00 | 0.29 | 0.11 | 8.76 |
| IMC02-19 | 0.05 | 3.65 | 0.24 | 3.18 | 68.92 | 19.62 | 1.28 | 1.02 | 1.13 | 0.05 | 0.45 | 0.00 | 0.30 | 0.12 | 8.64 |

TABLE 12-continued

Fatty acid composition of M₄ generation seed from three mutant lines exhibiting reduced saturated fatty acid content

| Line | C140 | C160 | C161 | C180 | C181 | C182 | C183 | C200 | C201 | C202 | C220 | C221 | C240 | C241 | Total sat |
|---|---|---|---|---|---|---|---|---|---|---|---|---|---|---|---|
| IMC02-20 | 0.05 | 3.71 | 0.26 | 2.79 | 66.85 | 22.13 | 1.55 | 0.87 | 1.10 | 0.06 | 0.41 | 0.00 | 0.22 | 0.00 | 8.05 |
| IMC02Ave | 0.05 | 3.75 | 0.24 | 3.01 | 68.87 | 19.63 | 1.36 | 0.98 | 1.14 | 0.05 | 0.45 | 0.00 | 0.28 | 0.17 | 8.52 |
| IMC201-01 | 0.05 | 4.01 | 0.19 | 2.45 | 77.44 | 10.56 | 2.01 | 0.93 | 1.38 | 0.05 | 0.47 | 0.02 | 0.28 | 0.15 | 8.20 |
| IMC201-02 | 0.05 | 3.94 | 0.18 | 2.44 | 77.52 | 10.55 | 2.09 | 0.92 | 1.38 | 0.05 | 0.46 | 0.02 | 0.26 | 0.15 | 8.07 |
| IMC201-03 | 0.06 | 4.06 | 0.21 | 2.59 | 76.51 | 11.16 | 2.06 | 0.94 | 1.34 | 0.05 | 0.46 | 0.02 | 0.26 | 0.28 | 8.37 |
| IMC201-04 | 0.06 | 4.02 | 0.21 | 2.46 | 76.25 | 11.61 | 2.21 | 0.87 | 1.32 | 0.05 | 0.42 | 0.00 | 0.23 | 0.29 | 8.05 |
| IMC201-05 | 0.05 | 4.10 | 0.20 | 2.56 | 76.42 | 11.35 | 2.07 | 0.93 | 1.34 | 0.05 | 0.46 | 0.02 | 0.28 | 0.15 | 8.39 |
| IMC201-06 | 0.05 | 4.05 | 0.21 | 2.50 | 76.36 | 11.51 | 2.08 | 0.91 | 1.37 | 0.05 | 0.45 | 0.03 | 0.26 | 0.16 | 8.23 |
| IMC201-07 | 0.07 | 4.22 | 0.22 | 2.62 | 75.71 | 11.77 | 2.05 | 0.94 | 1.35 | 0.05 | 0.47 | 0.02 | 0.26 | 0.25 | 8.58 |
| IMC201-08 | 0.05 | 3.64 | 0.18 | 2.63 | 77.81 | 10.20 | 2.02 | 0.96 | 1.47 | 0.06 | 0.47 | 0.02 | 0.31 | 0.17 | 8.07 |
| IMC201-09 | 0.05 | 4.41 | 0.24 | 2.85 | 63.92 | 22.50 | 2.79 | 0.96 | 1.20 | 0.08 | 0.48 | 0.02 | 0.32 | 0.17 | 9.08 |
| IMC201-10 | 0.05 | 4.03 | 0.18 | 2.48 | 77.12 | 10.69 | 2.17 | 0.90 | 1.33 | 0.05 | 0.45 | 0.00 | 0.23 | 0.31 | 8.15 |
| IMC201Ave | 0.06 | 4.05 | 0.20 | 2.56 | 75.51 | 12.19 | 2.16 | 0.93 | 1.35 | 0.05 | 0.46 | 0.02 | 0.27 | 0.21 | 8.32 |
| Westar16-01 | 0.06 | 4.41 | 0.30 | 2.34 | 65.36 | 18.31 | 6.50 | 0.76 | 1.13 | 0.06 | 0.35 | 0.00 | 0.22 | 0.19 | 8.15 |
| Westar16-02 | 0.06 | 4.25 | 0.26 | 2.37 | 67.28 | 16.80 | 6.24 | 0.75 | 1.13 | 0.05 | 0.35 | 0.02 | 0.20 | 0.24 | 7.99 |
| Westar16-03 | 0.06 | 4.20 | 0.26 | 2.46 | 66.06 | 17.62 | 6.71 | 0.76 | 1.13 | 0.06 | 0.37 | 0.00 | 0.20 | 0.11 | 8.05 |
| Westar16-04 | 0.07 | 4.52 | 0.29 | 2.54 | 64.75 | 18.82 | 6.53 | 0.74 | 1.04 | 0.06 | 0.34 | 0.00 | 0.19 | 0.11 | 8.40 |
| Westar16-05 | 0.07 | 4.30 | 0.27 | 2.43 | 65.09 | 18.31 | 6.67 | 0.80 | 1.19 | 0.07 | 0.39 | 0.00 | 0.25 | 0.17 | 8.23 |
| Westar16-06 | 0.08 | 4.54 | 0.30 | 2.39 | 65.63 | 17.74 | 6.44 | 0.81 | 1.15 | 0.06 | 0.39 | 0.00 | 0.25 | 0.21 | 8.46 |
| Westar16-07 | 0.08 | 4.34 | 0.28 | 2.57 | 65.47 | 17.92 | 6.57 | 0.79 | 1.12 | 0.06 | 0.35 | 0.00 | 0.20 | 0.27 | 8.32 |
| Westar16-08 | 0.07 | 4.37 | 0.28 | 2.18 | 64.49 | 19.54 | 6.61 | 0.64 | 1.05 | 0.06 | 0.28 | 0.00 | 0.15 | 0.28 | 7.70 |
| Westar16-09 | 0.08 | 4.65 | 0.29 | 2.35 | 61.81 | 21.30 | 6.72 | 0.72 | 1.21 | 0.08 | 0.33 | 0.00 | 0.20 | 0.27 | 8.33 |
| Westar16-10 | 0.06 | 4.26 | 0.25 | 2.54 | 67.17 | 16.96 | 5.85 | 0.80 | 1.17 | 0.06 | 0.38 | 0.00 | 0.22 | 0.28 | 8.27 |
| Westar16Ave | 0.07 | 4.39 | 0.28 | 2.42 | 65.31 | 18.33 | 6.48 | 0.76 | 1.13 | 0.06 | 0.35 | 0.00 | 0.21 | 0.21 | 8.19 |

Example 8

DH Line Salomon

A cross was made between 15.24 (Example 1) and 1764-92-05 (Example 7). A DH population was generated by collecting $F_1$ microspores from the cross, treating the microspores with colchicine, and propagating them in vitro. Plantlets formed in vitro from the microspores were moved to a greenhouse and inflorescences that formed were self pollinated. Seed was harvested from the $DH_1$ plants at maturity and analyzed for fatty acid profile. Seeds from those plants exhibiting reduced saturated fatty acid content were grown in the greenhouse and in the field. Table 13 contains the fatty acid profile of seeds produced by greenhouse-grown plants of a $DH_1$ population designated Salomon. Table 14 contains the fatty acid profile of seeds from three plants of DH line Salomon-05 grown in the field and re-coded to Salomon-005. The fatty acid profile of IMC111RR, a registered Canadian *B. napus* variety, is included as a control in Table 14. The field grown seed of individual plants of Salomon 005 had a range of 3.83% to 4.44% total saturates with 2.92% to 3.35% palmitic acid and 0.29% to 0.47% stearic acid. Line Salomon-005 demonstrated the lowest total saturated fatty acid profile of the DH lines in the greenhouse and in the field.

Table 15 contains the fatty acid profile of seeds from individual Salomon-005 plants, progeny of DH line Salomon, as grown in a growth chamber under the conditions described in Example 6. Under the high temperature environment (20/17), selfed plants of Salomon 005 had a total saturated fatty acid range of 4.13% to 4.67% with palmitic acid of 2.55% to 2.70% and stearic acid of 1.05 to 0.78%. Seed from the same Salomon 005 DH1 source when grown in a low temperature environment (14/11) had a total saturates of 3.45% to 3.93% with palmitic acid of 2.25% to 2.39% and stearic acid of 0.57% to 0.85%. The FATA2 mutation from 15.24 when combined with other low saturate mutations such as 1764, 1975, and 2650 can further reduce total saturates through the additive reduction of palmitic and stearic acids.

In the low 14/11 environment, Salomon-005-09 exhibited the lowest palmitic acid content, Salomon-005-05 exhibited the lowest stearic acid content, and Salomon-005-07 exhibited the lowest total saturated fatty acid content. Table 15 also contains the profile of individual plants of 15.24, IMC201, and F6 progeny of 1764-43-06×1975-90-14 (see Example 10). The data indicate that a low temperature environment reduces the amount of saturated fatty acids in the seed oil.

Lines 1764, 1975 and 2650 are also crossed with 15.36 (Example 3) to generate progeny having reduced saturated fatty acid content.

TABLE 13

Seed Fatty acid composition of progeny of $DH_1$ line Salomon in the greenhouse

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| Salomon-01 | 0.05 | 3.68 | 0.33 | 2.24 | 72.56 | 16.20 | 2.16 | 0.73 | 1.19 | 0.064 | 0.35 | 0.00 | 0.23 | 0.23 | 7.28 |
| Salomon-02 | 0.04 | 2.66 | 0.17 | 1.60 | 72.33 | 14.38 | 4.28 | 0.67 | 2.05 | 0.16 | 0.30 | 0.00 | 0.24 | 0.13 | 6.49 |
| Salomon-03 | 0.04 | 2.89 | 0.21 | 1.59 | 76.24 | 13.68 | 2.28 | 0.66 | 1.57 | 0.07 | 0.33 | 0.00 | 0.24 | 0.20 | 5.74 |
| Salomon-04 | 0.05 | 3.17 | 0.19 | 1.40 | 79.15 | 9.70 | 3.47 | 0.56 | 1.52 | 0.06 | 0.29 | 0.00 | 0.24 | 0.21 | 5.70 |
| Salomon-05 | 0.03 | 3.19 | 0.16 | 1.22 | 75.41 | 12.99 | 3.58 | 0.57 | 1.92 | 0.14 | 0.33 | 0.00 | 0.30 | 0.16 | 5.65 |
| Salomon-06 | 0.05 | 3.67 | 0.24 | 1.53 | 76.15 | 12.12 | 3.49 | 0.66 | 1.53 | 0.06 | 0.32 | 0.00 | 0.18 | 0.00 | 6.40 |
| Salomon-07 | 0.05 | 4.37 | 0.20 | 0.87 | 77.28 | 10.76 | 3.46 | 0.43 | 1.81 | 0.10 | 0.25 | 0.00 | 0.22 | 0.20 | 6.19 |

TABLE 13-continued

Seed Fatty acid composition of progeny of DH₁ line Salomon in the greenhouse

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| Salomon-08 | 0.05 | 4.19 | 0.25 | 1.29 | 78.05 | 10.35 | 2.99 | 0.59 | 1.65 | 0.08 | 0.34 | 0.00 | 0.19 | 0.00 | 6.64 |
| Average | 0.05 | 3.48 | 0.22 | 1.47 | 75.9 | 12.52 | 3.21 | 0.61 | 1.66 | 0.092 | 0.31 | 0.00 | 0.23 | 0.14 | 6.26 |

TABLE 14

Seed Fatty acid composition of DH₂ line Salomon-005 in the field

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| Salomon-005 | 0.036 | 2.92 | 0 | 0.29 | 73.16 | 14.02 | 5.83 | 0.21 | 2.57 | 0.13 | 0.27 | 0.05 | 0.11 | 0.406 | 3.83 |
| Salomon-005 | 0.036 | 2.85 | 0 | 0.55 | 74.17 | 13.24 | 5.74 | 0.27 | 2.44 | 0.12 | 0.28 | 0.02 | 0.02 | 0.268 | 3.99 |
| Salomon-005 | 0.043 | 3.35 | 0 | 0.47 | 71.35 | 15.20 | 5.90 | 0.24 | 2.63 | 0.17 | 0.32 | 0.06 | 0.03 | 0.251 | 4.44 |
| Average | 0.038 | 3.04 | 0.0 | 0.44 | 72.89 | 14.15 | 5.82 | 0.24 | 2.55 | 0.14 | 0.29 | 0.04 | 0.05 | 0.308 | 4.09 |
| IMC111RR | 0.08 | 5.06 | 0.41 | 2.07 | 56.80 | 28.40 | 3.87 | 0.83 | 1.44 | 0.14 | 0.50 | 0.00 | 0.23 | 0.162 | 8.77 |
| IMC111RR | 0.09 | 5.38 | 0.50 | 2.09 | 56.61 | 28.38 | 3.50 | 0.81 | 1.41 | 0.13 | 0.50 | 0.01 | 0.53 | 0.083 | 9.40 |
| IMC111RR | 0.21 | 6.15 | 0.50 | 1.46 | 47.82 | 36.03 | 3.38 | 0.71 | 1.24 | 0.14 | 0.56 | 0.00 | 1.43 | 0.369 | 10.5 |

TABLE 15

Seed fatty acid profile of individual DH line Salomon-005 Plants, 15.24, IMC201, and F6 plants in the growth chamber

| Genotype | Environment | 14:0 | 16:0 | 16:1 | 18:0 | 18:1 | 18:2 | 18:3 | 20:0 | 20:1 | 20:2 | 22:0 | 22:1 | 24:0 | 24:1 | Total Sats |
|---|---|---|---|---|---|---|---|---|---|---|---|---|---|---|---|---|
| Salomon-005-01 | High 20/17 | 0.02 | 2.59 | 0.14 | 1.05 | 76.66 | 11.34 | 5.29 | 0.44 | 1.68 | 0.12 | 0.27 | 0.04 | 0.14 | 0.21 | 4.51 |
| Salomon-005-02 | High 20/17 | 0.02 | 2.64 | 0.13 | 0.93 | 76.44 | 12.61 | 4.65 | 0.37 | 1.56 | 0.13 | 0.23 | 0.04 | 0.11 | 0.15 | 4.31 |
| Salomon-005-03 | High 20/17 | 0.02 | 2.63 | 0.12 | 0.83 | 77.05 | 11.95 | 4.82 | 0.34 | 1.62 | 0.12 | 0.23 | 0.04 | 0.10 | 0.13 | 4.15 |
| Salomon-005-04 | High 20/17 | 0.02 | 2.57 | 0.12 | 0.84 | 77.73 | 11.43 | 4.60 | 0.35 | 1.68 | 0.13 | 0.24 | 0.04 | 0.11 | 0.14 | 4.13 |
| Salomon-005-05 | High 20/17 | 0.02 | 2.67 | 0.13 | 1.08 | 75.92 | 12.43 | 4.82 | 0.47 | 1.67 | 0.13 | 0.28 | 0.05 | 0.15 | 0.19 | 4.67 |
| Salomon-005-06 | High 20/17 | 0.02 | 2.56 | 0.13 | 1.03 | 76.63 | 12.18 | 4.84 | 0.40 | 1.56 | 0.12 | 0.25 | 0.04 | 0.11 | 0.13 | 4.37 |
| Salomon-005-07 | High 20/17 | 0.02 | 2.58 | 0.13 | 0.78 | 77.50 | 11.64 | 4.49 | 0.36 | 1.78 | 0.14 | 0.26 | 0.05 | 0.12 | 0.18 | 4.11 |
| Salomon-005-08 | High 20/17 | 0.02 | 2.70 | 0.14 | 0.90 | 76.60 | 11.80 | 4.92 | 0.41 | 1.73 | 0.14 | 0.27 | 0.04 | 0.13 | 0.20 | 4.44 |
| Salomon-005-09 | High 20/17 | 0.02 | 2.58 | 0.12 | 0.88 | 77.75 | 11.62 | 4.50 | 0.34 | 1.61 | 0.12 | 0.22 | 0.04 | 0.10 | 0.10 | 4.14 |
| Salomon-005-10 | High 20/17 | 0.02 | 2.46 | 0.13 | 0.99 | 77.92 | 11.20 | 4.55 | 0.41 | 1.62 | 0.13 | 0.26 | 0.04 | 0.13 | 0.16 | 4.28 |
| Salomon-005-01 | Low 14/11 | 0.02 | 2.27 | 0.12 | 0.68 | 73.66 | 13.53 | 6.86 | 0.32 | 1.83 | 0.13 | 0.25 | 0.06 | 0.06 | 0.21 | 3.59 |
| Salomon-005-02 | Low 14/11 | 0.02 | 2.39 | 0.14 | 0.85 | 74.61 | 13.00 | 6.54 | 0.34 | 1.48 | 0.05 | 0.25 | 0.05 | 0.07 | 0.18 | 3.93 |
| Salomon-005-03 | Low 14/11 | 0.02 | 2.39 | 0.14 | 0.74 | 73.41 | 14.26 | 6.47 | 0.32 | 1.66 | 0.13 | 0.24 | 0.03 | 0.05 | 0.15 | 3.76 |
| Salomon-005-04 | Low 14/11 | 0.02 | 2.37 | 0.15 | 0.68 | 73.55 | 14.02 | 6.52 | 0.31 | 1.71 | 0.12 | 0.24 | 0.05 | 0.06 | 0.19 | 3.69 |
| Salomon-005-05 | Low 14/11 | 0.01 | 2.33 | 0.11 | 0.57 | 72.96 | 15.04 | 6.19 | 0.27 | 1.84 | 0.16 | 0.23 | 0.04 | 0.06 | 0.19 | 3.47 |
| Salomon-005-06 | Low 14/11 | 0.02 | 2.32 | 0.14 | 0.84 | 73.64 | 13.54 | 6.96 | 0.32 | 1.59 | 0.10 | 0.25 | 0.06 | 0.07 | 0.16 | 3.82 |
| Salomon-005-07 | Low 14/11 | 0.02 | 2.31 | 0.12 | 0.60 | 72.14 | 15.60 | 6.54 | 0.25 | 1.78 | 0.14 | 0.21 | 0.05 | 0.06 | 0.17 | 3.45 |
| Salomon-005-08 | Low 14/11 | 0.02 | 2.39 | 0.14 | 0.61 | 72.72 | 14.76 | 6.38 | 0.30 | 1.97 | 0.14 | 0.24 | 0.05 | 0.07 | 0.21 | 3.64 |
| Salomon-005-09 | Low 14/11 | 0.02 | 2.25 | 0.14 | 0.73 | 74.30 | 13.27 | 6.75 | 0.31 | 1.66 | 0.10 | 0.23 | 0.04 | 0.05 | 0.15 | 3.60 |
| Salomon-005-10 | Low 14/11 | 0.03 | 2.30 | 0.14 | 0.81 | 74.10 | 13.40 | 6.91 | 0.13 | 1.60 | 0.05 | 0.24 | 0.06 | 0.06 | 0.18 | 3.57 |
| F6-01 | High 20/17 | 0.03 | 2.60 | 0.14 | 0.97 | 77.08 | 13.84 | 2.51 | 0.44 | 1.57 | 0.09 | 0.30 | 0.04 | 0.17 | 0.23 | 4.51 |
| F6-02 | High 20/17 | 0.03 | 2.66 | 0.16 | 1.08 | 75.93 | 14.82 | 2.56 | 0.46 | 1.55 | 0.09 | 0.29 | 0.03 | 0.14 | 0.18 | 4.68 |
| F6-03 | High 20/17 | 0.02 | 2.54 | 0.12 | 0.97 | 74.35 | 16.41 | 2.44 | 0.45 | 1.85 | 0.13 | 0.31 | 0.04 | 0.15 | 0.22 | 4.44 |
| F6-04 | High 20/17 | 0.03 | 2.59 | 0.16 | 1.17 | 77.17 | 13.62 | 2.55 | 0.50 | 1.48 | 0.08 | 0.29 | 0.03 | 0.15 | 0.20 | 4.72 |
| F6-05 | High 20/17 | 0.03 | 2.39 | 0.12 | 1.24 | 74.19 | 15.98 | 2.97 | 0.50 | 1.77 | 0.12 | 0.31 | 0.04 | 0.16 | 0.20 | 4.62 |
| F6-06 | High 20/17 | 0.03 | 2.46 | 0.12 | 1.30 | 74.78 | 15.28 | 2.97 | 0.53 | 1.72 | 0.11 | 0.32 | 0.05 | 0.14 | 0.21 | 4.77 |
| F6-07 | High 20/17 | 0.03 | 2.59 | 0.17 | 1.23 | 75.88 | 14.86 | 2.49 | 0.52 | 1.45 | 0.08 | 0.34 | 0.03 | 0.18 | 0.16 | 4.88 |
| F6-08 | High 20/17 | 0.03 | 2.43 | 0.13 | 1.35 | 74.57 | 15.91 | 2.65 | 0.53 | 1.59 | 0.11 | 0.31 | 0.03 | 0.19 | 0.16 | 4.84 |
| F6-09 | High 20/17 | 0.03 | 2.58 | 0.18 | 1.27 | 77.36 | 13.34 | 2.44 | 0.54 | 1.46 | 0.08 | 0.34 | 0.03 | 0.18 | 0.19 | 4.94 |
| F6-10 | High 20/17 | 0.03 | 2.31 | 0.12 | 1.28 | 75.12 | 14.90 | 2.99 | 0.53 | 1.84 | 0.12 | 0.33 | 0.04 | 0.17 | 0.23 | 4.65 |
| F6-01 | Low 14/11 | 0.02 | 2.47 | 0.14 | 0.92 | 73.90 | 16.63 | 3.30 | 0.39 | 1.51 | 0.10 | 0.27 | 0.03 | 0.10 | 0.22 | 4.17 |
| F6-02 | Low 14/11 | 0.02 | 2.34 | 0.14 | 0.88 | 75.11 | 15.79 | 3.16 | 0.37 | 1.56 | 0.09 | 0.25 | 0.03 | 0.08 | 0.18 | 3.94 |
| F6-03 | Low 14/11 | 0.02 | 2.38 | 0.12 | 0.91 | 74.76 | 15.89 | 3.28 | 0.37 | 1.57 | 0.11 | 0.28 | 0.03 | 0.09 | 0.19 | 4.04 |
| F6-04 | Low 14/11 | 0.02 | 2.35 | 0.15 | 0.97 | 74.66 | 16.22 | 3.15 | 0.39 | 1.50 | 0.09 | 0.26 | 0.03 | 0.07 | 0.17 | 4.06 |
| F6-05 | Low 14/11 | 0.03 | 2.50 | 0.17 | 0.98 | 74.94 | 15.83 | 3.10 | 0.37 | 1.42 | 0.06 | 0.27 | 0.05 | 0.08 | 0.19 | 4.23 |
| F6-06 | Low 14/11 | 0.02 | 2.45 | 0.14 | 0.91 | 74.36 | 16.44 | 3.10 | 0.36 | 1.52 | 0.07 | 0.27 | 0.06 | 0.08 | 0.20 | 4.10 |
| F6-07 | Low 14/11 | 0.03 | 2.49 | 0.15 | 0.94 | 75.38 | 15.37 | 3.45 | 0.25 | 1.42 | 0.06 | 0.17 | 0.04 | 0.07 | 0.18 | 3.94 |
| F6-08 | Low 14/11 | 0.02 | 2.34 | 0.14 | 0.89 | 74.17 | 16.578 | 3.21 | 0.37 | 1.67 | 0.10 | 0.25 | 0.04 | 0.07 | 0.17 | 3.94 |
| F6-09 | Low 14/11 | 0.03 | 2.69 | 0.23 | 1.10 | 69.80 | 20.52 | 2.73 | 0.46 | 1.59 | 0.13 | 0.32 | 0.08 | 0.12 | 0.23 | 4.71 |
| F6-10 | Low 14/11 | 0.02 | 2.44 | 0.16 | 0.92 | 73.55 | 16.87 | 3.39 | 0.38 | 1.60 | 0.09 | 0.28 | 0.04 | 0.07 | 0.19 | 4.12 |
| IMC201-01 | High 20/17 | 0.05 | 3.79 | 0.18 | 2.34 | 77.38 | 10.98 | 2.25 | 0.84 | 1.30 | 0.06 | 0.40 | 0.02 | 0.23 | 0.20 | 7.64 |
| IMC201-02 | High 20/17 | 0.05 | 4.30 | 0.22 | 1.86 | 77.13 | 11.37 | 2.37 | 0.69 | 1.23 | 0.06 | 0.36 | 0.03 | 0.17 | 0.17 | 7.43 |
| IMC201-04 | High 20/17 | 0.05 | 4.03 | 0.19 | 2.05 | 76.20 | 12.56 | 2.31 | 0.69 | 1.21 | 0.06 | 0.34 | 0.02 | 0.15 | 0.15 | 7.30 |
| IMC201-05 | High 20/17 | 0.05 | 4.34 | 0.22 | 1.84 | 76.58 | 11.93 | 2.43 | 0.68 | 1.20 | 0.06 | 0.34 | 0.02 | 0.16 | 0.17 | 7.40 |
| IMC201-06 | High 20/17 | 0.05 | 4.06 | 0.20 | 2.21 | 75.83 | 12.34 | 2.49 | 0.78 | 1.25 | 0.06 | 0.36 | 0.02 | 0.19 | 0.15 | 7.65 |

TABLE 15-continued

Seed fatty acid profile of individual DH line Salomon-005 Plants, 15.24, IMC201, and F6 plants in the growth chamber

| Genotype | Environment | 14:0 | 16:0 | 16:1 | 18:0 | 18:1 | 18:2 | 18:3 | 20:0 | 20:1 | 20:2 | 22:0 | 22:1 | 24:0 | 24:1 | Total Sats |
|---|---|---|---|---|---|---|---|---|---|---|---|---|---|---|---|---|
| IMC201-07 | High 20/17 | 0.05 | 3.99 | 0.19 | 2.16 | 76.33 | 12.22 | 2.27 | 0.77 | 1.24 | 0.05 | 0.36 | 0.02 | 0.17 | 0.18 | 7.50 |
| IMC201-08 | High 20/17 | 0.05 | 3.90 | 0.19 | 2.16 | 75.80 | 12.94 | 2.42 | 0.68 | 1.22 | 0.06 | 0.30 | 0.02 | 0.15 | 0.13 | 7.22 |
| IMC201-09 | High 20/17 | 0.03 | 3.41 | 0.13 | 2.46 | 76.72 | 12.12 | 2.37 | 0.72 | 1.35 | 0.07 | 0.30 | 0.01 | 0.18 | 0.12 | 7.10 |
| IMC201-10 | High 20/17 | 0.05 | 4.26 | 0.20 | 2.06 | 78.16 | 10.15 | 2.02 | 0.84 | 1.32 | 0.05 | 0.44 | 0.02 | 0.25 | 0.18 | 7.90 |
| IMC201-01 | Low 14/11 | 0.05 | 3.76 | 0.21 | 1.63 | 76.15 | 12.63 | 2.98 | 0.61 | 1.27 | 0.06 | 0.34 | 0.04 | 0.11 | 0.16 | 6.51 |
| IMC201-02 | Low 14/11 | 0.05 | 3.67 | 0.20 | 1.62 | 76.61 | 12.52 | 2.96 | 0.37 | 1.32 | 0.05 | 0.31 | 0.03 | 0.11 | 0.20 | 6.13 |
| IMC201-04 | Low 14/11 | 0.06 | 4.02 | 0.23 | 1.47 | 74.65 | 13.94 | 3.03 | 0.58 | 1.33 | 0.06 | 0.33 | 0.03 | 0.13 | 0.15 | 6.58 |
| IMC201-05 | Low 14/11 | 0.05 | 3.97 | 0.22 | 1.49 | 75.43 | 13.43 | 2.74 | 0.58 | 1.36 | 0.06 | 0.34 | 0.03 | 0.11 | 0.18 | 6.54 |
| IMC201-06 | Low 14/11 | 0.04 | 3.66 | 0.20 | 1.59 | 75.94 | 12.96 | 2.98 | 0.55 | 1.32 | 0.08 | 0.34 | 0.05 | 0.10 | 0.20 | 6.28 |
| IMC201-07 | Low 14/11 | 0.02 | 2.53 | 0.16 | 1.09 | 75.76 | 15.24 | 3.20 | 0.14 | 1.29 | 0.08 | 0.24 | 0.02 | 0.07 | 0.16 | 4.08 |
| IMC201-08 | Low 14/11 | 0.03 | 3.49 | 0.13 | 1.73 | 74.49 | 14.29 | 3.38 | 0.40 | 1.61 | 0.04 | 0.21 | 0.02 | 0.06 | 0.13 | 5.92 |
| IMC201-10 | Low 14/11 | 0.04 | 3.84 | 0.21 | 1.42 | 75.88 | 12.93 | 2.93 | 0.57 | 1.43 | 0.07 | 0.36 | 0.020 | 0.12 | 0.19 | 6.35 |
| 15.24-01 | High 20/17 | 0.03 | 3.14 | 0.12 | 1.12 | 77.45 | 11.38 | 3.87 | 0.46 | 1.71 | 0.13 | 0.28 | 0.04 | 0.14 | 0.14 | 5.17 |
| 15.24-02 | High 20/17 | 0.03 | 3.16 | 0.14 | 1.45 | 76.54 | 11.27 | 4.38 | 0.56 | 1.70 | 0.11 | 0.30 | 0.05 | 0.15 | 0.17 | 5.65 |
| 15.24-03 | High 20/17 | 0.03 | 3.18 | 0.14 | 1.39 | 77.14 | 10.63 | 4.44 | 0.58 | 1.70 | 0.11 | 0.30 | 0.03 | 0.16 | 0.16 | 5.64 |
| 15.24-04 | High 20/17 | 0.02 | 3.25 | 0.12 | 1.11 | 76.16 | 11.90 | 4.40 | 0.48 | 1.79 | 0.14 | 0.28 | 0.04 | 0.13 | 0.17 | 5.28 |
| 15.24-05 | High 20/17 | 0.03 | 3.12 | 0.12 | 1.10 | 77.38 | 11.11 | 4.20 | 0.44 | 1.81 | 0.14 | 0.26 | 0.04 | 0.14 | 0.13 | 5.08 |
| 15.24-06 | High 20/17 | 0.03 | 2.90 | 0.13 | 1.28 | 76.83 | 11.53 | 4.00 | 0.51 | 1.90 | 0.15 | 0.29 | 0.05 | 0.17 | 0.24 | 5.18 |
| 15.24-07 | High 20/17 | 0.02 | 3.19 | 0.13 | 1.28 | 75.24 | 12.39 | 4.88 | 0.49 | 1.70 | 0.14 | 0.27 | 0.03 | 0.12 | 0.13 | 5.37 |
| 15.24-08 | High 20/17 | 0.03 | 3.18 | 0.13 | 1.23 | 76.44 | 11.21 | 4.67 | 0.51 | 1.83 | 0.12 | 0.29 | 0.04 | 0.15 | 0.18 | 5.39 |
| 15.24-09 | High 20/17 | 0.02 | 3.12 | 0.14 | 1.41 | 77.36 | 10.36 | 4.48 | 0.58 | 1.75 | 0.10 | 0.31 | 0.03 | 0.16 | 0.17 | 5.60 |
| 15.24-10 | High 20/17 | 0.04 | 3.18 | 0.14 | 1.43 | 76.19 | 11.33 | 4.71 | 0.56 | 1.67 | 0.11 | 0.29 | 0.05 | 0.14 | 0.16 | 5.64 |
| 15.24-02 | Low 14/11 | 0.04 | 3.09 | 0.15 | 0.64 | 75.62 | 11.81 | 5.84 | 0.37 | 1.76 | 0.11 | 0.27 | 0.07 | 0.09 | 0.16 | 4.49 |
| 15.24-03 | Low 14/11 | 0.03 | 2.71 | 0.12 | 1.04 | 75.80 | 11.73 | 5.74 | 0.28 | 1.95 | 0.07 | 0.20 | 0.04 | 0.11 | 0.19 | 4.36 |
| 15.24-04 | Low 14/11 | 0.02 | 2.85 | 0.11 | 0.97 | 76.63 | 10.60 | 5.58 | 0.45 | 2.00 | 0.12 | 0.33 | 0.06 | 0.08 | 0.22 | 4.69 |
| 15.24-06 | Low 14/11 | 0.02 | 2.86 | 0.13 | 1.07 | 76.75 | 10.47 | 5.70 | 0.44 | 1.88 | 0.10 | 0.30 | 0.04 | 0.09 | 0.15 | 4.78 |
| 15.24-07 | Low 14/11 | 0.03 | 3.05 | 0.14 | 1.22 | 75.85 | 11.13 | 5.99 | 0.48 | 1.47 | 0.11 | 0.29 | 0.04 | 0.07 | 0.14 | 5.14 |
| 15.24-08 | Low 14/11 | 0.02 | 2.98 | 0.13 | 0.97 | 75.51 | 11.78 | 5.72 | 0.39 | 1.84 | 0.11 | 0.27 | 0.04 | 0.08 | 0.15 | 4.71 |
| 15.24-09 | Low 14/11 | 0.02 | 2.98 | 0.13 | 1.00 | 75.11 | 12.02 | 5.81 | 0.42 | 1.81 | 0.12 | 0.28 | 0.04 | 0.08 | 0.19 | 4.78 |
| 15.24-10 | Low 14/11 | 0.01 | 2.96 | 0.12 | 0.89 | 76.55 | 11.00 | 5.53 | 0.40 | 1.85 | 0.12 | 0.32 | 0.03 | 0.08 | 0.14 | 4.66 |

Example 9

DH Population Skechers

A DH population designated Skechers was obtained from a cross between 15.24 and 06SE-04GX-33. The 06SE-04GX-33 parent line was selected from progeny of a cross between 04GX-33 and 01NM.304. Line 04GX-33, which has an oleic acid content of about 80% and reduced saturated fatty acid content, was produced by crossing 01NM.304 and a European spring growth habit line 'Lila' and developing a DH population from the $F_1$ cross. Line 01NM.304 was developed from a DH population of an $F_1$ cross between IMC302 and Surpass 400. 06SE-04GX-33 seeds have a mean C14:0 content of 0.091%, a C16:0 content of 4.47%, a C16:1 content of 0.68%, a C18:0 content of 1.69%, a C18:1 content of 79.52%, a C18:2 content of 6.62%, a C18:3 content of 4.12%, a C20:0 content of 0.63%, a C20:1 content of 1.22%, a C22:0 content of 0.49%, a C22:1 content of 0.0%, a C24:0 content of 0.21%, and a C24:1 content of 0.24%.

This DH population was generated from the cross of 15.24 and 06SE-04GX-33 by collecting microspores, treating the microspores with colchicine, and propagating them in vitro. Plantlets formed in vitro from the microspores were moved to a greenhouse and inflorescences that formed were self pollinated. Seed was harvested from the $DH_1$ plants at maturity and analyzed for fatty acid profile via GC. Table 16 contains the fatty acid profile of seeds produced by plants grown in the greenhouse and in the field of DH lines selected from the Skechers population. The fatty acid profile of IMC 111 RR is included as a control in Table 16. Skechers-159 and Skechers-339 exhibited a low total saturated fatty acid profile in the greenhouse and in the field (Table 16).

TABLE 16

Fatty acid composition of seed of Skechers 339 and Skechers 159

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| Greenhouse | | | | | | | | | | | | | | | |
| Skechers-339 | 0.04 | 2.86 | 0.20 | 1.11 | 84.53 | 4.40 | 3.61 | 0.48 | 1.98 | 0.12 | 0.27 | 0.00 | 0.23 | 0.17 | 4.98 |
| Skechers-159 | 0.03 | 2.91 | 0.19 | 1.26 | 84.24 | 4.05 | 3.57 | 0.55 | 1.88 | 0.15 | 0.34 | 0.00 | 0.00 | 0.82 | 5.08 |
| Field | | | | | | | | | | | | | | | |
| Skechers-339 | 0.00 | 2.55 | 0.12 | 0.94 | 82.64 | 5.07 | 5.44 | 0.39 | 2.11 | 0.16 | 0.28 | 0.04 | 0.14 | 0.13 | 4.29 |
| Skechers-339 | 0.00 | 2.80 | 0.16 | 1.22 | 81.55 | 5.57 | 4.89 | 0.50 | 2.25 | 0.21 | 0.52 | 0.00 | 0.19 | 0.16 | 5.22 |
| Skechers-339 | 0.000 | 3.01 | 0.22 | 1.04 | 79.43 | 7.39 | 5.12 | 0.46 | 2.21 | 0.20 | 0.55 | 0.04 | 0.17 | 0.18 | 5.23 |
| Mean | 0.00 | 2.79 | 0.17 | 1.07 | 81.20 | 6.01 | 5.15 | 0.45 | 2.19 | 0.19 | 0.44 | 0.03 | 0.17 | 0.16 | 4.91 |
| Skechers-159 | 0.03 | 2.65 | 0.14 | 1.03 | 83.52 | 5.07 | 5.09 | 0.41 | 2.04 | 0.00 | 0.00 | 0.01 | 0.01 | 0.00 | 4.13 |
| Skechers-159 | 0.03 | 2.60 | 0.15 | 0.97 | 82.93 | 4.80 | 5.52 | 0.39 | 2.16 | 0.13 | 0.33 | 0.00 | 0.00 | 0.01 | 4.32 |
| Skechers-159 | 0.04 | 2.69 | 0.23 | 0.95 | 82.99 | 5.08 | 5.18 | 0.39 | 2.06 | 0.12 | 0.28 | 0.00 | 0.01 | 0.00 | 4.35 |

TABLE 16-continued

Fatty acid composition of seed of Skechers 339 and Skechers 159

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| Skechers-159 | 0.04 | 2.59 | 0.15 | 0.90 | 80.65 | 5.50 | 5.48 | 0.36 | 2.08 | 0.12 | 2.12 | 0.00 | 0.00 | 0.00 | 6.01 |
| Mean | 0.04 | 2.63 | 0.17 | 0.96 | 82.52 | 5.11 | 5.32 | 0.39 | 2.08 | 0.09 | 0.68 | 0.00 | 0.01 | 0.01 | 4.70 |
| IMC111RR | 0.08 | 5.06 | 0.41 | 2.07 | 56.80 | 28.40 | 3.87 | 0.83 | 1.44 | 0.14 | 0.50 | 0.00 | 0.23 | 0.16 | 8.77 |
| IMC111RR | 0.09 | 5.38 | 0.50 | 2.09 | 56.61 | 28.38 | 3.50 | 0.81 | 1.41 | 0.13 | 0.50 | 0.01 | 0.53 | 0.08 | 9.40 |
| IMC111RR | 0.21 | 6.15 | 0.50 | 1.46 | 47.82 | 36.03 | 3.38 | 0.71 | 1.24 | 0.14 | 0.56 | 0.00 | 1.43 | 0.37 | 10.52 |

Example 10

Line 1764-43-06×1975-90-14

A pedigree selection program was carried out with progeny of a cross of 1764-43-06×1975-90-14 over multiple cycles of single plant selections in the greenhouse for low total saturated fatty acid content in seeds. Table 17 contains the seed fatty acid profile of each parent used to make the $F_1$ cross. Table 18 contains the seed fatty acid profile of selections advanced through the $F_6$ generation. The mean seed fatty acid profiles of the inbred 01PR06RR.001B and the variety IMC201 are shown for comparison. Additional rounds of self-pollination and selection for low total saturated fatty acids can be performed.

TABLE 17

Fatty acid composition of seed of Lines 1975-90-14 and 1764-43-06

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| 1975-90-14 | 0.00 | 3.78 | 0.23 | 1.54 | 75.12 | 14.06 | 2.08 | 0.64 | 1.62 | 0.09 | 0.38 | 0.0 | 0.27 | 0.18 | 6.61 |
| 1764-43-06 | 0.039 | 3.28 | 0.31 | 2.40 | 75.45 | 12.97 | 1.96 | 0.90 | 1.54 | 0.08 | 0.48 | 0.0 | 0.42 | 0.17 | 7.52 |

TABLE 18

Seed Fatty acid composition of F2-F6 generations selected in progeny 1764-43-06 × 1975-90-14

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| F2 seed | | | | | | | | | | | | | | | |
| E626033 | 0.063 | 4.33 | 0.63 | 1.59 | 63.33 | 22.87 | 4.04 | 0.63 | 1.50 | 0.13 | 0.39 | 0.00 | 0.26 | 0.25 | 7.26 |
| E626088 | 0.051 | 3.41 | 0.26 | 1.58 | 72.76 | 16.44 | 2.16 | 0.64 | 1.68 | 0.10 | 0.39 | 0.00 | 0.23 | 0.30 | 6.30 |
| E626134 | 0.042 | 3.40 | 0.23 | 1.66 | 73.61 | 15.71 | 1.96 | 0.70 | 1.69 | 0.09 | 0.42 | 0.03 | 0.26 | 0.20 | 6.48 |
| E626082 | 0.05 | 3.50 | 0.26 | 1.69 | 72.38 | 16.58 | 2.05 | 0.69 | 1.61 | 0.09 | 0.41 | 0.00 | 0.24 | 0.45 | 6.58 |
| 01PR06RR.001B Mean | 0.07 | 4.73 | 0.37 | 2.17 | 66.27 | 21.15 | 2.13 | 0.87 | 1.12 | 0.06 | 0.49 | 0.01 | 0.36 | 0.21 | 8.69 |
| F3 seed | | | | | | | | | | | | | | | |
| E642092 | 0.05 | 3.57 | 0.32 | 1.06 | 60.40 | 27.06 | 4.14 | 0.46 | 1.85 | 0.17 | 0.43 | 0.00 | 0.20 | 0.29 | 5.77 |
| E642105 | 0.03 | 2.98 | 0.16 | 1.67 | 74.64 | 14.52 | 2.39 | 0.67 | 1.88 | 0.10 | 0.39 | 0.04 | 0.28 | 0.24 | 6.02 |
| E641751 | 0.04 | 3.16 | 0.19 | 1.40 | 73.53 | 15.88 | 2.57 | 0.57 | 1.74 | 0.12 | 0.35 | 0.00 | 0.23 | 0.23 | 5.75 |
| E641767 | 0.04 | 2.99 | 0.18 | 1.46 | 72.85 | 16.25 | 2.59 | 0.59 | 1.92 | 0.14 | 0.39 | 0.06 | 0.27 | 0.26 | 5.74 |
| E642058 | 0.02 | 3.56 | 0.31 | 1.26 | 70.79 | 18.60 | 2.65 | 0.51 | 1.59 | 0.12 | 0.30 | 0.00 | 0.18 | 0.11 | 5.84 |
| E642706 | 0.00 | 2.95 | 0.20 | 1.49 | 72.76 | 16.92 | 2.58 | 0.60 | 1.59 | 0.11 | 0.30 | 0.00 | 0.23 | 0.27 | 5.57 |
| E641983 | 0.03 | 3.21 | 0.23 | 1.62 | 71.50 | 17.62 | 2.51 | 0.63 | 1.74 | 0.12 | 0.33 | 0.00 | 0.22 | 0.23 | 6.05 |
| E641989 | 0.0403 | 2.9929 | 0.22 | 1.44 | 73.11 | 16.43 | 2.67 | 0.57 | 1.65 | 0.11 | 0.34 | 0.00 | 0.22 | 0.21 | 5.61 |
| E642042 | 0.0000 | 2.8352 | 0.16 | 1.81 | 75.94 | 13.78 | 2.08 | 0.69 | 1.86 | 0.10 | 0.35 | 0.00 | 0.25 | 0.14 | 5.94 |
| E642071 | 0.0371 | 3.0309 | 0.20 | 1.77 | 72.45 | 16.74 | 2.74 | 0.63 | 1.75 | 0.12 | 0.31 | 0.00 | 0.21 | 0.00 | 6.00 |
| 01PR06RR.001B Mean | 0.0637 | 4.6079 | 0.36 | 1.94 | 66.25 | 21.83 | 2.03 | 0.77 | 1.15 | 0.06 | 0.43 | 0.01 | 0.32 | 0.19 | 8.12 |
| F4 seed | | | | | | | | | | | | | | | |
| F604402 | 0.0266 | 2.4461 | 0.14 | 1.15 | 75.79 | 14.69 | 2.74 | 0.46 | 1.83 | 0.12 | 0.25 | 0.04 | 0.12 | 0.22 | 4.44 |
| F603986 | 0.0183 | 2.323 | 0.13 | 1.32 | 77.47 | 13.68 | 2.57 | 0.51 | 1.37 | 0.07 | 0.32 | 0 | 0 | 0.22 | 4.50 |
| 01PR06RR.001B Mean | 0.0501 | 4.5160 | 0.33 | 1.84 | 66.82 | 21.10 | 2.32 | 0.77 | 1.22 | 0.06 | 0.48 | 0.02 | 0.27 | 0.21 | 7.93 |
| F5 Seed - Chamber 15°/12° Seed from F604402: | | | | | | | | | | | | | | | |
| FTF647808 | 0 | 2.45 | 0.2 | 1.16 | 76.27 | 14.48 | 2.97 | 0.45 | 1.39 | 0.06 | 0.26 | 0 | 0.08 | 0.22 | 4.41 |
| FTF647745 | 0 | 2.2 | 0 | 1.20 | 75.65 | 14.88 | 3.56 | 0.46 | 1.47 | 0.08 | 0.27 | 0 | 0 | 0.21 | 4.13 |

TABLE 18-continued

Seed Fatty acid composition of F2-F6 generations selected in progeny 1764-43-06 × 1975-90-14

| Line | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| FTF647752 | 0 | 2.41 | 0.15 | 1.21 | 76.42 | 14.52 | 2.86 | 0.43 | 1.42 | 0.09 | 0.23 | 0 | 0.07 | 0.19 | 4.34 |
| FTF647789 | 0 | 2.51 | 0.2 | 1.12 | 74.75 | 16.15 | 2.72 | 0.43 | 1.44 | 0.08 | 0.26 | 0.04 | 0.09 | 0.22 | 4.4 |
| Seed from F603986: | | | | | | | | | | | | | | | |
| FTF647754 | 0 | 2.28 | 0.15 | 1.12 | 77.12 | 13.73 | 3.01 | 0.44 | 1.49 | 0.07 | 0.27 | 0.04 | 0.07 | 0.21 | 4.19 |
| FTF647775 | 0 | 2.28 | 0.16 | 1.15 | 76.91 | 13.82 | 2.96 | 0.47 | 1.54 | 0.07 | 0.31 | 0.04 | 0.08 | 0.22 | 4.28 |
| FTF647804 | 0 | 2.39 | 0.17 | 1.21 | 77.55 | 13.2 | 3.07 | 0.48 | 1.40 | 0.00 | 0.25 | 0 | 0.08 | 0.2 | 4.41 |
| FTF647777 | 0 | 2.25 | 0.17 | 1.17 | 77.39 | 13.63 | 2.83 | 0.46 | 1.46 | 0.06 | 0.27 | 0.03 | 0.07 | 0.21 | 4.22 |
| FTF647778 | 0 | 2.29 | 0 | 1.26 | 77.6 | 13.41 | 2.94 | 0.47 | 1.38 | 0.07 | 0.30 | 0 | 0.08 | 0.21 | 4.39 |
| IMC201 Mean | 0.038 | 3.9 | 0.20 | 1.80 | 77.244 | 11.588 | 2.81 | 0.65 | 1.15 | 0.03 | 0.30 | 0 | 0.11 | 0.2 | 6.80 |
| F6 Seed Chamber 20°/17° Seed from FTF647754: | | | | | | | | | | | | | | | |
| FTG603509 | 0.03 | 2.66 | 0.14 | 1.39 | 76.57 | 14.16 | 2.52 | 0.53 | 1.36 | 0.08 | 0.28 | 0.02 | 0.13 | 0.13 | 5.01 |
| FTG603519 | 0.03 | 2.56 | 0.15 | 1.32 | 76.7 | 14.05 | 2.43 | 0.57 | 1.43 | 0.08 | 0.32 | 0.03 | 0.17 | 0.16 | 4.97 |
| FTG603505 | 0.02 | 2.47 | 0.14 | 1.33 | 79.5 | 11.43 | 2.22 | 0.58 | 1.52 | 0.07 | 0.34 | 0.02 | 0.21 | 0.16 | 4.95 |
| FTG603506 | 0.07 | 3.59 | 0.14 | 2.73 | 68.43 | 19.28 | 3.41 | 0.76 | 0.89 | 0.04 | 0.30 | 0.00 | 0.22 | 0.13 | 7.67 |
| FTG603517 | 0.03 | 2.66 | 0.16 | 1.44 | 76.75 | 13.94 | 2.44 | 0.56 | 1.37 | 0.07 | 0.29 | 0.02 | 0.14 | 0.13 | 5.12 |
| FTG603507 | 0.03 | 2.63 | 0.15 | 1.31 | 76.59 | 14.18 | 2.5 | 0.53 | 1.39 | 0.05 | 0.29 | 0.02 | 0.16 | 0.18 | 4.94 |
| FTG603508 | 0.03 | 2.51 | 0.12 | 1.38 | 75.88 | 14.61 | 2.58 | 0.56 | 1.56 | 0.09 | 0.33 | 0.03 | 0.16 | 0.15 | 4.97 |
| FTG603515 | 0.03 | 2.74 | 0.13 | 1.33 | 75.67 | 14.91 | 2.71 | 0.49 | 1.36 | 0.08 | 0.25 | 0.02 | 0.12 | 0.14 | 4.97 |
| FTG603516 | 0.03 | 2.65 | 0.13 | 1.41 | 76.32 | 14.16 | 2.37 | 0.6 | 1.54 | 0.09 | 0.34 | 0.03 | 0.18 | 0.16 | 5.21 |
| FTG603520 | 0.03 | 2.72 | 0.14 | 1.42 | 75.61 | 14.9 | 2.37 | 0.57 | 1.49 | 0.09 | 0.32 | 0.03 | 0.16 | 0.15 | 5.23 |

Example 11

Seed Fatty Acid Profiles for Field-Grown Plants

Plants of 15.24, Salomon-03, Salomon-05, Salomon-07, an F6 selected line described in Example 10, Skechers-159 and Skecher-339 were grown in field plots in Aberdeen, SK, Canada. At maturity, seeds from each line were harvested and fatty acid content determined by GC analysis. The ranges of palmitic, stearic, oleic, linoleic, and linolenic acid content, and the range of total saturated fatty acids are shown in Table 19. The ranges for seed of line Q2 and Pioneer® variety 46A65 are shown for comparison.

TABLE 19

Fatty Acid Profiles for Field-Grown Plants

| Genotype | C16:0 | C18:0 | C18:1 | C18:2 | C18:3 | Total Sats |
|---|---|---|---|---|---|---|
| 46A65 | 3.37-4.12 | 1.53-2.29 | 64.85-71.46 | 13.57-19.16 | 5.06-7.95 | 6.24-7.52 |
| Q2 | 3.53-4.10 | 1.46-2.10 | 63.03-70.49 | 13.79-19.44 | 6.15-10.28 | 6.14-7.62 |
| Salomon-07 | 3.44-4.20 | 0.71-0.81 | 73.68-76.74 | 11.76-13.24 | 3.66-4.08 | 4.96-5.97 |
| Salomon-05 | 3.02-3.34 | 0.95-1.11 | 72.74-74.51 | 13.70-15.94 | 3.40-4.69 | 4.34-5.22 |
| 15.24 | 2.77-3.19 | 0.95-1.06 | 77.16-77.95 | 10.76-12.02 | 3.42-3.68 | 4.53-5.36 |
| Selection from 1764-43-06 × 1975-90-14 | 2.42-2.73 | 0.97-1.29 | 71.07-73.56 | 15.65-18.80 | 2.75-2.91 | 4.21-5.19 |
| Salomon-03 | 2.24-2.51 | 1.08-1.36 | 72.20-76.70 | 14.15-18.15 | 2.03-2.71 | 4.38-4.81 |
| Skechers-339 | 2.38-2.84 | 0.91-1.28 | 79.93-86.50 | 3.95-4.90 | 3.23-4.90 | 4.03-5.23 |
| Skechers-159 | 2.37-3.75 | 0.91-1.26 | 83.97-86.45 | 3.49-4.80 | 4.11-4.47 | 4.11-4.47 |

Example 12

Radiation Mutagenesis (RMU) of 15.24 Germplasm

About 30 grams (~8000 seeds) of $M_0$ seeds from an individual selected from the DH population of 15.24×01OB240 on the basis of low total saturates (see Example 2) were mutagenized using cesium irradiation at 45 krad. About 1500 of the mutagenized seeds were planted in the greenhouse immediately after irradiation, about 500 of them developed into plants to produce $M_1$ seeds. About 840 $M_1$ seeds were planted and M2 seed was harvested. M2 seed was planted along with $F_1$ progeny plants of a cross of 15.24×01OB240 (designated control 1; $M_0$ seed) were also planted. The fatty acid composition of M3 seeds produced by individual $M_2$ plants and control plants was analyzed by GC. The results are shown in Table 20 under the M2 heading. The individual $M_2$ plant producing $M_3$ seeds with the lowest total saturates was 08AP-RMU-tray 3-18, which had 5.28% total saturates compared to 6.48% for control-1. The individual $M_2$ plant producing $M_3$ seeds with the lowest 16:0 was 08AP-RMU-tray 13-25, which had 2.55% 16:0 compared with 3.19% for control-1. The individual $M_2$ plant producing $M_3$ seeds with the lowest 18:0 was 08AP-RMU-tray 10-34, which had an 18:0 content of 0.93% compared with 1.7% for control-1. $M_3$ seed used to generate fatty acid profiles shown in Table 20 was planted from these three lines in the greenhouse.

M$_4$ plants derived from M$_3$ seed with low total saturates, 16:0, and 18:0, respectively, from each of the three groups were selected for use in crosses. Line M4-L1601-12 had a total saturates content of 5.28% in the M$_3$ generation and was selected from the 08AP-RMU-tray 3-18 lineage. A cross was made between plants of line M4-L1601-12 and a line containing the homozygous mutant alleles of Isoforms 1, 2, 3, 4 of FatB (described in Example 6). Seed fatty acid profiles from F$_2$ seeds for two F$_1$ individuals are shown in Table 20. Plants of lines M4-Lsat1-23 and M4-L1601-22 were crossed, and the fatty acid profile for seeds produced on an F$_1$ individual designated 09AP-RMU-003-06 are shown in Table 20. M4-Lsat1-23 and M4-L1601-22 were selected from the M3 generation with total saturate of 5.02% and 16:0 of 2.43%. Plants of lines M4-L1601-12×M4-D60-2-01 were crossed, and the fatty acid profile for seeds produced on an F$_1$ individual designated 09AP-RMU-012-2 are shown in Table 20. M4-L1601-12×M4-D60-2-01 were selected from the M3 generation with total saturates of 5.28% and 18:0 of 0.88%, respectively. Seeds from F$_1$ plants with low total saturated fatty acid content, low 16:0, and low 18:0 were grown for further pedigree selection breeding. Some plants were self-pollinated and used to generate DH populations for further selection. It is expected that total saturated fatty acid content in seeds produced on F$_2$ plants and on progeny of the DH populations will be lower than that in seeds produced on F$_1$ plants, due to genetic segregation for homozygosity for mutant alleles at loci that confer the low total saturates phenotype.

introducing genes from the low saturate line 15.24 into a commercially grown hybrid, Victory® v1035. Hybrid v1035 has an average oleic acid content of 65%. Plants of the line 15.24, and the inbreds 01PR06RR.001B and 95CB504, were planted in a greenhouse. Inbred 01PR06RR.001B is the male parent of v1035. Inbred 95CB504 is the B line female parent of v1035. Plants of 010PR06RR.001B and 15.24 were cross pollinated in the greenhouse as were 95CB504 and 15.24, as shown in Table 21.

TABLE 21

| Female | x | Male |
|---|---|---|
| 01PR06RR.001B (R-line) | | 15.24 |
| 95CB504 (B-line) | | 15.24 |

F$_1$ progeny from the cross of 95CB504 and 15.24 were backcrossed to 95CB04 to produce BC$_1$-B progeny, which were selfed (BC$_1$S). Plants with low total saturates were selected from the BC$_1$-B selfed progeny, and backcrossed to 95CB504 to produce BC$_2$-B progeny. F$_1$ progeny from the cross of 01PR06RR.001B and 15.24 were backcrossed to 01PR06RR.001B to produce BC$_1$-R progeny, which were selfed. Plants with low total saturates were selected from the BC$_1$-R selfed progeny, and backcrossed to 01PR06RR.001B to produce BC$_2$-R progeny. Backcrossing, selection, and self-pollination of the BC-B and BC-R progeny were continued for multiple generations. The 95CB504 male sterile A line,

TABLE 20

| Identifier | C140 | C160 | C161 | C180 | C181 | C182 | C183 | C200 | C201 | C202 | C220 | C221 | C240 | C241 | Total Sats |
|---|---|---|---|---|---|---|---|---|---|---|---|---|---|---|---|
| 15.24 × 01OB240 (control 1) M2 | 0.04 | 3.19 | 0.14 | 1.7 | 78.32 | 10.51 | 2.23 | 0.73 | 2.03 | 0.13 | 0.41 | 0.05 | 0.39 | 0.13 | 6.45 |
| 08AP-RMU-tray13-25 | 0.03 | 2.55 | 0.1 | 1.68 | 78.86 | 10.86 | 2.14 | 0.7 | 2.16 | 0.14 | 0.35 | 0.01 | 0.3 | 0.13 | 5.61 |
| 08AP-RMU-tray10-34 | 0.02 | 3.08 | 0.02 | 0.93 | 79.4 | 10.51 | 2.24 | 0.61 | 2.11 | 0.15 | 0.4 | 0.05 | 0.34 | 0.14 | 5.39 |
| 08AP-RMU-tray3-18 M4 | 0.02 | 2.96 | 0.1 | 1.16 | 80.49 | 9.68 | 2.07 | 0.56 | 2.12 | 0.14 | 0.35 | 0.04 | 0.23 | 0.08 | 5.28 |
| M4-L1601-12 | 0 | 3.26 | 0 | 1.76 | 72.64 | 15.82 | 2.95 | 0.76 | 2.13 | 0.2 | 0.49 | 0 | 0 | 0 | 6.26 |
| Salomon-05 (control 2) F1 of RMU mutants × RMU mutants | 0 | 2.49 | 0.11 | 1.67 | 77.95 | 10.05 | 4.25 | 0.64 | 1.93 | 0.12 | 0.32 | 0.05 | 0.23 | 0.2 | 5.58 |
| 09AP-RMU-003-06 [M4-Lsat1-23 × M4-L1601-22] | 0.03 | 2.66 | 0.06 | 1.47 | 79.34 | 10.6 | 2.11 | 0.67 | 2.06 | 0.15 | 0.36 | 0.07 | 0.25 | 0.2 | 5.42 |
| 09AP-RMU-012-2 [M4-L1601-12 × M4-D60-2-01] F1 of RMU mutants × mutant FatB 1, 2, 3, 4 | 0.03 | 2.79 | 0.11 | 1.44 | 77.36 | 12.4 | 2.36 | 0.64 | 1.93 | 0.14 | 0.38 | 0.05 | 0.21 | 0.15 | 5.5 |
| 09AP-RMU-008-07 [M4-L1601-12 × Iso1234 | 0.04 | 2.98 | 0.18 | 1.74 | 72.18 | 17.38 | 2.37 | 0.7 | 1.44 | 0.11 | 0.37 | 0.04 | 0.26 | 0.22 | 6.09 |
| 09AP-RMU-008-05 [M4-L1601-12 × Iso1234 | 0.02 | 2.74 | 0.17 | 2.08 | 74.02 | 15.78 | 2.14 | 0.74 | 1.41 | 0.11 | 0.35 | 0.02 | 0.24 | 0.2 | 6.17 |

Example 13

Development of Hybrid Canola Producing Reduced Saturated Fat Seed Oil

A hybrid canola variety yielding seeds with a total saturated fatty acid content of less than 6% was produced by 000A05, was converted to a low saturated phenotype in parallel with the conversion of the 95CB504 B line.

Hybrid seed was generated by hand, using BC$_1$S$_3$ generation plants of the 95CB504 B line as the female parent and BC$_1$S$_3$ generation plants of the 01PR06RR.001B R line as the male parent. The hybrid seed was grown at 5 locations×4 replications in Western Canada. In the trial plot locations, some individual plants were bagged for self pollination (5 locations×2 reps) and seeds harvested at maturity. The remaining plants were not bagged (5 locations×4 reps) and seeds were harvested in bulk. As such, the bulk samples had some level of out crossing with non-low saturate fatty acid lines in adjacent plots. Seeds from the individual and bulk samples were analyzed for fatty acid content. Seeds from control plants of line Q2, hybrid v1035 and commercial variety 46A65 were also harvested individually and in bulk.

Table 22 shows the fatty acid profile of the individually bagged samples and bulked samples for hybrid 1524 and controls. The results indicate that seed produced by Hybrid 1524 has a statistically significant decrease in 16:0 content and 18:0 content relative to the controls, and a statistically significant increase in 20:1 content relative to controls. In addition, seeds produced by Hybrid 1524 have a statistically significant decrease in total saturated fatty acid content relative to controls. The total saturated fatty acid content for individually bagged plants is about 5.7%, or about 0.8% less than the parent hybrid which lacks the FatA2 mutation contributed by line 15.24. The total saturated fatty acid content for bulk seed is about 5.9%, or more than 0.9% less than the parent hybrid which lacks the FatA2 mutation contributed by line 15.24.

TABLE 22

Seed Fatty Acid Profile

| Mean C16:0 | N | Line | Mean C18:0 | N | Line |
|---|---|---|---|---|---|
| 3.902 a | 11 | Q2 | 1.903 a | 16 | V1035Bulk |
| 3.876 a | 16 | Q2Bulk | 1.899 a | 16 | Q2Bulk |
| 3.675 b | 16 | 46A65Bulk | 1.887 a | 16 | 46A65Bulk |
| 3.669 b | 16 | V1035Bulk | 1.803 ab | 9 | 46A65 |
| 3.594 bc | 9 | 46A65 | 1.765 b | 11 | Q2 |
| 3.513 cd | 10 | V1035 | 1.744 b | 10 | V1035 |
| 3.414 de | 16 | H1524Bulk | 1.405 c | 16 | H1524Bulk |
| 3.344 e | 10 | H1524 | 1.283 d | 10 | H1524 |

| Mean C20:1 | N | Line | Mean Total Sats | N | Line |
|---|---|---|---|---|---|
| 1.660 a | 10 | H1524 | 6.986 a | 16 | Q2Bulk |
| 1.599 a | 16 | H1524Bulk | 6.875 a | 11 | Q2 |
| 1.421 b | 10 | V1035 | 6.859 a | 16 | V1035Bulk |
| 1.398 b | 16 | Q2Bulk | 6.776 ab | 16 | 46A65Bulk |
| 1.336 b | 16 | V1035Bulk | 6.601 b | 9 | 46A65 |
| 1.332 b | 16 | 46A65Bulk | 6.568 b | 10 | V1035 |
| 1.331 b | 9 | 46A65 | 5.911 c | 16 | H1524Bulk |
| 1.265 b | 11 | Q2 | 5.704 d | 10 | H1524 |

Another hybrid canola variety yielding seeds with a low total saturated fatty acid content is produced by introducing genes from the low saturate line Skechers-339 into a commercially grown hybrid, using the backcrossing and selection program described above for v1035.

Another hybrid canola variety yielding seeds with a low total saturated fatty acid content is produced by crossing $F_6$ progeny of a cross of 1764-43-06×1975-90-14, selected for low total saturates, with the parent inbreds of a commercially grown hybrid. An A line, a B line and an R line are selected for low total saturates, using backcrossing and selection as described above for v1035.

Another hybrid canola variety yielding seeds with a low total saturated fatty acid content is produced by crossing Salomon-05, with the parent inbreds of a commercially grown hybrid. An A line, a B line and an R line are selected for low total saturates, using backcrossing and selection as described above for v1035.

Another hybrid canola variety yielding seeds with a low total saturated fatty acid content is produced by crossing Iso 1234 with the parent inbreds of hybrid 1524. An A line, a B line and an R line are selected for low total saturates, using backcrossing and selection as described above for v1035. The resulting hybrid, designated Hybrid A2-1234, carries a mutant FatA2 allele and mutant FatB alleles at isoforms 1, 2, 3, and 4.

Another hybrid canola variety yielding seeds with a low total saturated fatty acid content is produced by crossing a variety homozygous for a mutant Fad2 allele and a mutant Fad3 allele with the parent inbreds of Hybrid A2-1234. An A line, a B line and an R line are selected for low total saturates, using backcrossing and selection as described above for v1035. The resulting hybrid carries a mutant FatA2 allele, mutant FatB alleles at isoforms 1, 2, 3, and 4, a mutant Fad2 allele, and a mutant Fad3 allele.

Another hybrid canola variety yielding seeds with a low total saturated fatty acid content is produced by introducing genes from the low saturate line 15.36 into a commercially grown hybrid, using the backcrossing and selection program described above for v1035.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A *Brassica* plant comprising a mutant allele at a fatty acyl-acyl-ACP thioesterase A2 (FATA2) locus, wherein said mutant allele results in the production of a FATA2 polypeptide having reduced thioesterase activity relative to a corresponding wild-type FATA2 polypeptide, and wherein said plant produces seeds yielding an oil having a total saturated fatty acid content of less than 6%.

2. The plant of claim 1, wherein said mutant allele comprises a nucleic acid encoding a FATA2 polypeptide having a mutation in a region (SEQ ID NO:29) corresponding to amino acids 242 to 277 of the FATA2 polypeptide.

3. The plant of claim 2, wherein said FATA2 polypeptide comprises a substitution of a leucine residue for proline at position 255.

4. The plant of claim 1, said plant further comprising a mutant allele at a FAD2 locus, said mutant allele comprising a nucleic acid encoding a FAD2 polypeptide having a lysine substituted for glutamic acid in a HECGH motif.

5. The plant of claim 1, said plant further comprising mutant alleles at four different FATB loci.

6. The plant of claim 5, wherein each of said FATB mutant alleles results in the production of a FATB polypeptide having reduced thioesterase activity relative to a corresponding wild-type FATB polypeptide.

7. The plant of claim 5, wherein at least one of said FATB mutant alleles comprises a nucleic acid encoding a truncated FATB polypeptide.

8. The plant of claim 1, wherein said plant is a *Brassica napus, Brassica juncea,* or *Brassica rapa* plant.

9. The plant of claim 1, wherein said plant is an F1 hybrid.

10. Progeny of the plant of claim 1, said progeny comprising said mutant allele.

11. Seeds of the plant of claim 1, wherein the seeds comprise said mutant allele at a FATA2 locus.

12. The seeds of claim 11, wherein said seeds yield an oil having a total saturated fatty acid content of 3.45% to 5.5%.

13. The seeds of claim 11, wherein said seeds yield an oil having an oleic acid content of 78% to 80.14%, a linoleic acid content of about 8% to 10%, an α-linolenic acid content of no more than about 4%, and an eicosenoic acid content of 1.6% to 2.3%.

14. The seeds of claim 12, wherein said seeds are F2 seeds.

15. The seeds of claim 12, wherein said *Brassica* plant further comprises mutant alleles at four different FATB loci.

16. The seeds of claim 11, wherein said seeds yield an oil having a total saturated fatty acid content of less than 6%.

17. The seeds of claim 11, wherein said seeds yield an oil having a total saturated fatty acid content of 3.6% or less.

18. The plant of claim 1, wherein said seeds yield an oil having a total saturated fatty acid content of 2.5% to 5.5%.

19. The plant of claim 1, wherein said seeds yield an oil having a total saturated fatty acid content of 3.6% or less.

* * * * *

SEQUENCE LISTING

```
<160> NUMBER OF SEQ ID NOS: 52

<210> SEQ ID NO 1
<211> LENGTH: 1557
<212> TYPE: DNA
<213> ORGANISM: Brassica napus

<400> SEQUENCE: 1
atggtggcta cttgcgctac gtcgtcgttt tttcatgttc catcttcttc ctcgcttgat      60
actaatggga aggggaacag agttgggtct actaattttg ctggacttaa ctcaacgcca     120
agctctggga ggatgaaggt taagccaaac gcttaggctc cacccaagat caacgggaag     180
aaagctaact tgcctggctc tgtagagata tcaaagtctg acaacgagac ttcgcaaccc     240
```

```
gcacacgcac cgaggacgtt tatcaaccag ctacctgact ggagcatgct tcttgctgcc      300
ataacaacta ttttcttagc ggcggagaaa cagtggatga tgcttgactg gaaacctagg      360
cgttctgata tgattatgga tcctttcggt ttagggagaa tcgttcagga tggtcttgtg      420
ttccgtcaga atttttccat taggtcttat gagataggtg ctgatcgctc tgcgtctata      480
gaaactgtca tgaatcattt acaggtactg ctttgattgt ggttacactc acatgttgtc      540
ccaatagata tatgctcatg acaagctctt atgctaatga caggaaacgg cgcttaatca      600
tgtgaagtct gccggactgc tggaaaatgg gtttgggtcc actcctgaga tgtttaagaa      660
gaatttgata tgggtcgttg ctcgtatgca ggttgtcgtt gataaatatc ctacttggta      720
agccattgtt agtcttagca cttgacttaa aatcattttg catattacag tgtgcgtaga      780
tcatttgctt attcaaatat ctgactcaca ggggagatgt tgtggaagtg gatacttggg      840
ttagtcagtc tggaaagaat ggtatgcgtc gtgattggct agttcgggat tgcaatactg      900
gagaaattgt aacgcgagca tcaaggtcag agttcttata ttttggttta ctccagctat      960
tatcgttttg ctctctgttt gtattgtttc ctctgccatt agtttgataa ttgagtcttt     1020
atagttgtat atgtatggca attttcttct ttttgcagtt tgtgggtgat gatgaataaa     1080
ctcacaagga gattgtcaaa gattcctgaa gaggttcgag gggaaataga gccttatttt     1140
gtgaactctg atcctgtcat tgccgaagac agcagaaagt taacaaaact tgatgacaag     1200
actgctgact atgttcgttc tggtctcact gtaagtacct tacctttcga caagcctgtc     1260
aaaactcttg aggttctaat ggtttggtaa tgaactttt tttggcagcc gaggtggagt     1320
gacttggatg ttaaccagca tgttaacaat gtaaagtaca ttgggtggat actggagagt     1380
gctccagcag ggatgctgga gagtcagaag ctgaaaagca tgactctgga gtatcgcagg     1440
gagtgcggga gagacagtgt gcttcagtct ctcaccgcag tctctggatg tgatgtcggt     1500
aacctcggga cagccgggga agtggagtgt cagcatttgc ttcgactcca ggatgga       1557
```

<210> SEQ ID NO 2
<211> LENGTH: 1572
<212> TYPE: DNA
<213> ORGANISM: Brassica napus

<400> SEQUENCE: 2

```
atggtggcca cctcagctac atcctcattc ttccctctcc catcttcccc cctcgacccc       60
accgcaaaaa ccaacaaagt caccacctcc accaacttct ccggcctcac acccacgccg      120
aactccgcca ggatgaaggt taaaccaaac gctcaggccc cacccaagat caacggcaag      180
agagtcggcc tccctggctc ggtggagatc ttgaagcctg atagcgagac ttcgcaacca      240
gcaccgagga cgttcatcaa ccagctgcct gactggagca tgctcctcgc cgccatcacg      300
accgtcttct tggcggctga gaagcagtgg atgatgctcg actggaaacc gaggcgttct      360
gacgtgatta tggatccgtt tgggttaggg aggatcgttc aggatgggct tgtgttccgt      420
cagaattttt ctattcggtc ttatgagata ggtgctgatc gctctgcgtc tatagaaacg      480
gttatgaatc atttacaggt actgattatg attatgattg tagtcgcttg ttgttactgg      540
acaaacttaa atatgtattg ctcttatggt tgtgatagga acggcactc aaccatgtta      600 agactgctgg gctgcttgga gatgggtttg ttctactcc tgagatggtt aagaagaact      660
tgatatgggt tgttactcgt atgtaggttg tcgttgataa atatcctact tggtaagcta      720
ttctcaaaca actctgagaa tcactgcttc ctttgtgagt catttgctta ttcaaatatc      780
```

| | |
|---|---|
| tgcctcatag gggagatgtt gtggaagtag atacatgggt gagccagtct ggaaagaacg | 840 |
| gtatgcgtcg tgattggctt gttcgggatg gcaatactgg agagatttta acaagagcat | 900 |
| caaggttaga ttttattttt tggtttactt gggttagata tctgataatt gagttataat | 960 |
| catctccgtg ttgtgtaaac tattctttttt gcagtgtgtg ggtgatgatg aataaactga | 1020 |
| caagaagatt atcaaagatt cctgaagagg ttcgagggga gatagagcct tactttgtta | 1080 |
| actcagaccc agtccttgcc gaggacagca gaaagttaac aaaacttgat gacaaaactg | 1140 |
| ctgtctatgt tcgttctggt ctcactgtaa gtacaaatac ttcactctat gtttcaacaa | 1200 |
| agcctgtaaa ttttgagtc tcttacaggt ttggtaatga acttttttgca gccgcgttgg | 1260 |
| agtgacttgg atgttaacca gcacgttaac aatgtgaagt catcgggtg gatactggag | 1320 |
| agtgctccag tggggatgat ggagagtcag aagctgaaaa gcatgactct ggagtatcgc | 1380 |
| agggagtgtg ggagagacag tgtgctccag tccctcaccg cggtttcggg ctgcgatatc | 1440 |
| ggtagcctcg ggacagccgg tgaagtggaa tgtcagcatc tgctcagact ccaggatgga | 1500 |
| gccgaagtgg tgagaggaag aacagagtgg agttccaaaa catcaacaac aacttgggac | 1560 |
| atcacaccgt ga | 1572 |

<210> SEQ ID NO 3
<211> LENGTH: 1500
<212> TYPE: DNA
<213> ORGANISM: Brassica napus

<400> SEQUENCE: 3

| | |
|---|---|
| atggtggcca cctcagctac atcctcattc ttccctctcc catcttcccc cctcgacccc | 60 |
| accgcaaaaa ccaacaaagt caccacctcc accaacttct ccggcctcac acccacgccg | 120 |
| aactccgcca ggatgaaggt taaaccaaac gctcaggccc cacccaagat caacggcaag | 180 |
| agagtcggcc tccctggctc ggtggagatc ttgaagcctg atagcgagac ttcgcaacca | 240 |
| gcaccgagga cgttcatcaa ccagctgcct gactgaagca tgctcctcgc cgccatcacg | 300 |
| accgtcttct tggcggctga aagcagtgg atgatgctcg actggaaacc gaggcgttct | 360 |
| gacgtgatta tggatccgtt tgggttaggg aggatcgttc aggatgggct tgtgttccgt | 420 |
| cagaattttt ctattcggtc ttatgagata ggtgctgatc gctctgcgtc tatagaaacg | 480 |
| gttatgaatc atttacaggt actgattatg attatgattg tagtcgcttg ttgttactgg | 540 |
| acaaacttaa atatgtattg ctcttatggt tgtgatagga acggcactc aaccatgtta | 600 |
| agactgctgg gctgcttgga gatgggtttg gttctactcc tgagatggtt aagaagaact | 660 |
| tgatatgggt tgttactcgt atgcaggttg tcgttgataa atatcctact tggtaagcta | 720 |
| ttctcaaaca actctgagaa tcactgcttc ctttgtgagt catttgctta ttcaaatatc | 780 |
| tgcctcatag gggagatgtt gtggaagtag atacatgggt gagccagtct ggaaagaacg | 840 |
| gtatgcgtcg tgattggctt gttcgggatg gcaatactgg agagatttta acaagagcat | 900 |
| caaggttaga ttttattttt tggtttactt gggttagata tctgataatt gagttataat | 960 |
| catctccgtg ttgtgtaaac tattctttttt gcagtgtgtg ggtgatgatg aataaactga | 1020 |
| caagaagatt atcaaagatt cctgaagagg ttcgagggga gatagagcct tactttgtta | 1080 |
| actcagaccc agtccttgcc gaggacagca gaaagttaac aaaacttgat gacaaaactg | 1140 |
| ctgtctatgt tcgttctggt ctcactgtaa gtacaaatac ttcactctat gtttcaacaa | 1200 |
| agcctgtaaa ttttgagtc tcttacaggt ttggtaatga acttttttgca gccgcgttgg | 1260 |
| agtgacttgg atgttaacca gcacgttaac aatgtgaagt catcgggtg gatactggag | 1320 |

```
agtgctccag tgggatgat ggagagtcag aagctgaaaa gcatgactct ggagtatcgc    1380
agggagtgtg ggagagacag tgtgctccag tccctcaccg cggtttcggg ctgcgatatc    1440
ggtagcctcg ggacagccgg tgaagtggaa tgtcagcatc tgctcagact ccaggatgga    1500
```

<210> SEQ ID NO 4
<211> LENGTH: 1664
<212> TYPE: DNA
<213> ORGANISM: Brassica napus

<400> SEQUENCE: 4

```
atggtggcta cttccgctac gtcgtcgttt tttcatgttc catcttcctc ctctcttgat     60
actaatggga aggggaacag agttgcgtcc acgaacttcg ctggacttaa ctcaacgcca    120
agctctggga ggatgaaggt taaaccaaac gctcaggctc cacccaagat caacgggaag    180
aaagctaact tgcctggttc tgcagagata tcaaagtctg acaacgagac ttcgcaaccc    240
gcacccgcac cgaggacgtt tatcaaccag ctgcctgact ggagcatgct tctcgctgcc    300
ataacaacta ttttcttagc ggctgagaaa cagtgaatga tgcttgactg gaaacccagg    360
cgttctgata tgataatgga tcctttcggt ttagggagaa tcgttcagga tggtcttgtg    420
tttcgtcaga atttctccat taggtcttat gagataggtg ctgatcgctc tgcgtctata    480
gaaactgtta tgaatcattt acaggtaggt actactttga ttgttatcac acttgtcact    540
ggacacccaa tagatatata tgctcatgac aagctcttat gctaatgaca ggaaacggcc    600
ctaaaccatg tgaagtctgc cggactgctg gaaaatgggt ttggttctac tcccgagatg    660
tttaagaaga acttgatatg ggtcgttgct cgtatgcagg ttgtcgttga taaatatcct    720
acttggtaag ccattgtcag tcttaccact taacttaaaa tcattatgca tattacagtt    780
tgcatagatc attacttatt caaatatctg actaacaggg gagatgttgt ggaagtggat    840
acatgggtta gtcagtccgg aaagaatggt atgcgtcgtg attggctggt tcgggattgc    900
aatactggag aaattgtaac gcgagcatca aggtcagagt tcttatgttt tggtttactg    960
actccagcta ttatcatttt gctctctgtt tgtattgttt gctctgccat taatatgata   1020
atagagactt tatagttgta tatgtatggc aattttcttc tttttgcagt tgtgggtga    1080 tgatgaataa actgacaagg agattgtcaa agattcctga agaggttcgt ggggaaatag   1140
agccttattt tgtgaactct gatcctgtca ttgccgaaga cagcagaaag ttaacaaaac   1200
tggatgacaa gactgctgac tatgttcgtt cgggtctcac tgtaagtacc ctacctttca   1260
acaagccttt aaaactcttg aggttctaat ggtttggtaa taaactttt tttcagccga   1320 gttggagtga cttagatgtt aaccagcatg ttaacaatgt aaagtacatt gggtggatac   1380
tggagagtgc tccagcaggg atgctggaga gtcagaagct gaaaagcatg actctggagt   1440
atcgcaggga gtgcgggaga gacagtgtgc ttcagtctct caccgcggtc tctggatgtg   1500
atgtcggtaa cctcgggaca gccggggaag tggagtgtca gcatttgctt cgtctccagg   1560
atggagctga agtggtgaga ggaagaacag ctgaagtggt gagaggaaga acagagtgga   1620
gttccaagat agaagcaaca acttgggaca ctgctacatc gtaa                   1664
```

<210> SEQ ID NO 5
<211> LENGTH: 5
<212> TYPE: PRT
<213> ORGANISM: Artificial Sequence
<220> FEATURE:
<223> OTHER INFORMATION: Amino acid motif

<400> SEQUENCE: 5

His Glu Cys Gly His
1               5

<210> SEQ ID NO 6
<211> LENGTH: 6
<212> TYPE: PRT
<213> ORGANISM: Artificial Sequence
<220> FEATURE:
<223> OTHER INFORMATION: Amino acid motif

<400> SEQUENCE: 6

Lys Tyr Leu Asn Asn Pro
1               5

<210> SEQ ID NO 7
<211> LENGTH: 10
<212> TYPE: PRT
<213> ORGANISM: Artificial Sequence
<220> FEATURE:
<223> OTHER INFORMATION: Amino acid motif

<400> SEQUENCE: 7

Asp Arg Asp Tyr Gly Ile Leu Asn Lys Val
1               5                   10

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
atgaaggtta aaccaaacgc tcaggc                                          26

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
tgttcttcct ctcaccactt cagc                                            24

<210> SEQ ID NO 10
<211> LENGTH: 1399
<212> TYPE: DNA
<213> ORGANISM: Brassica napus

<400> SEQUENCE: 10
tccacccaag atcaacggga agaaagctaa cttgcctggc tctgtagaga tatcaaagtc      60
tgacaacgag acttcgcaac ccgcacacgc accgaggacg tttatcaacc agctacctga     120
ctggagcatg cttcttgctg ccataacaac tattttctta gcggcggaga aacagtggat     180
gatgcttgac tggaaaccta ggcgttctga tatgattatg gatccttttcg gtttagggag     240 aatcgttcag gatggtcttg tgttccgtca gaattttttcc attaggtctt atgagatagg     300
tgctgatcgc tctgcgtcta tagaaactgt catgaatcat ttacaggtac tgctttgatt     360
gtggttacac tcacatgttg tcccaataga tatatgctca tgacaagctc ttatgctaat     420
gacaggaaac ggcgcttaat catgtgaagt ctgccggact gctggaaaat gggtttgggt     480

```
ccactcctga gatgtttaag aagaatttga tatgggtcgt tgctcgtatg caggttgtcg        540
ttgataaata tcctacttgg taagccattg ttagtcttag cacttgactt aaaatcattt        600
tgcatattac agtgtgcgta gatcatttgc ttattcaaat atctgactca caggggagat        660
gttgtggaag tggatacttg ggttagtcag tctggaaaga atggtatgcg tcgtgattgg        720
ctagttcggg attgcaatac tggagaaatt gtaacgcgag catcaaggtc agagttctta        780
tattttggtt tactccagct attatcgttt tgctctctgt ttgtattgtt tcctctgcca        840
ttagtttgat aattgagtct ttatagttgt atatgtatgg caattttctt cttttttgcag       900 tttgtgggtg atgatgaata aactcacaag gagattgtca agattcctg aagaggttcg         960 aggggaaata gagccttatt tgtgaactc tgatcctgtc attgccgaag acagcagaaa        1020
gttaacaaaa cttgatgaca agactgctga ctatgttcgt tctggtctca ctgtaagtac       1080
cttacctttc gacaagcctg tcaaaactct tgaggttcta atggttttggt aatgaacttt     1140 tttttggcag ccgaggtgga gtgacttgga tgttaaccag catgttaaca atgtaaagta       1200
cattgggtgg atactggaga gtgctccagc agggatgctg agagtcaga agctgaaaag        1260 catgactctg gagtatcgca gggagtgcgg gagagacagt gtgcttcagt ctctcaccgc       1320
agtctctgga tgtgatgtcg gtaacctcgg gacagccggg aagtggagt gtcagcattt       1380 gcttcgactc caggatgga                                                    1399
```

<210> SEQ ID NO 11
<211> LENGTH: 1330
<212> TYPE: DNA
<213> ORGANISM: Brassica napus

<400> SEQUENCE: 11

```
cccacccaag atcaacggca agagagtcgg tctcccttct ggctcggtga agcctgataa        60
cgagacgtcc tcacagcatc ccgcagcacc gaggacgttc atcaaccagc tgcctgactg       120
gagcatgctt cttgctgcaa taacaaccgt cttcttggcg gctgagaagc agtggatgat      180
gcttgactgg aaaccgaggc gctctgacgt gattatggat ccgtttgggt tagggaggat      240
cgttcaggat gggcttgtgt tccgtcagaa tttctctatt cggtcttatg agataggtgc      300
tgatcgctct gcgtctatag aaacggttat gaatcattta caggtactga ttatgattat      360
gattatgatt gtagttgctt gttgttactg gacaaagtta atatgtattg ctgttatggt      420
tatgatagga acggcactc aaccatgtta agactgctgg actgcttgga gatgggtttg       480
gttctactcc tgagatggtt aagaagaact tgatttgggt tgttactcgt atgcaggttg      540
tcgttgataa atatcctact tggtaagcta ttctcaagca accctgagaa tcactgcttc     600
ctttgtcatt tgcttattca aatatctgtc tcacagggga gatgttgtgg aagtagatac     660
atgggtgagc cagtctggaa agaacggtat gcgtcgtgat tggctagttc gagatggcaa     720
tactggagaa attttaacaa gagcatcaag gttagatttt tatttatcgg ttaggtatct     780
gaaaatttga gttactaatg caaaatatta ttttgcagt gtgtgggtga tgatgaataa      840
actgacaaga agattatcaa agattcctga agaggttcga ggggagatag agccttactt     900
tgttaattca gacccagtcc ttgctgagga cagcagaaag ttaactaaac ttgatgacaa      960
gactgctgac tatgttcgtt ctggtctcac tgtaagtatg catactttct ctatgtttca    1020
tcaaagcctg taaacttctg agattcttac agtttttatt tggtaattta aacttttgca    1080
gccgcgttgg agtgacttgg atgttaacca gcacgttaac aatgtgaagt acatcgggtg    1140
gatactggag agtgcacctg tggggatgat ggagagtcag aagctgaaaa gcatgactct    1200
```

```
ggagtatcgc agggagtgcg ggagggacag tgtgcttcag tccctcaccg cggtttcggg    1260
ctgcgatgtt ggtagtcttg ggacagctgg tgaagtggaa tgtcagcacc tgctccgtct    1320
ccaggatgga                                                           1330
```

<210> SEQ ID NO 12
<211> LENGTH: 1342
<212> TYPE: DNA
<213> ORGANISM: Brassica napus

<400> SEQUENCE: 12

```
cccacccaag atcaacggca agagagtcgg cctccctggc tcggtggaga tcttgaagcc     60
tgatagcgag acttcgcaac cagcaccgag gacgttcatc aaccagctgc ctgactggag    120
catgctcctc gccgccatca cgaccgtctt cttggcggct gagaagcagt ggatgatgct    180
cgactggaaa ccgaggcgtt ctgacgtgat tatggatccg tttgggttag ggaggatcgt    240
tcaggatggc cttgtgttcc gtcagaattt ttctattcgg tcttatgaga taggtgctga    300
tcgctctgcg tctatagaaa cggttatgaa tcatttacag gtactgatta tgattatgat    360
tgtagtcgct tgttgttact ggacaaactt aaatatgtat tgctcttatg gttgtgatag    420
gaaacggcac tcaaccatgt taagactgct gggctgcttg gagatgggtt tggttctact    480
cctgagatgg ttaagaagaa cttgatatgg gttgttactc gtatgcaggt tgtcgttgat    540
aaatatccta cttggtaagc tattctcaaa caactctgag aatcactgct tcctttgtga    600
gtcatttgct tattcaaata tctgcctcat aggggagatg ttgtggaagt agatacatgg    660
gtgagccagt ctggaaagaa cggtatgcgt cgtgattggc ttgttcggga tggcaatact    720
ggagagattt taacaagagc atcaaggtta gattttattt tttggtttac ttgggttaga    780
tatctgataa ttgagttata atcatctccg tgttgtgtaa actattcttt ttgcagtgtg    840
tgggtgatga tgaataaact gacaagaaga ttatcaaaga ttcctgaaga ggttcgaggg    900
gagatagagc cttactttgt taactcagac ccagtccttg ccgaggacag cagaaagtta    960
acaaaacttg atgacaaaac tgctgtctat gttcgttctg gtctcactgt aagtacaaat   1020
acttcactct atgtttcaac aaagcctgta aatttttgag tctcttacag gtttggtaat   1080 gaacttttg cagccgcgtt gggagtgactt ggatgttaac cagcacgtta acaatgtgaa   1140
gtacatcggg tggatactgg agagtgctcc agtgggatg atggagagtc agaagctgaa    1200
aagcatgact ctggagtatc gcagggagtg tgggagagac agtgtgctcc agtccctcac   1260
cgcggtttcg gctgcgata tcggtagcct cgggacagcc ggtgaagtgg aatgtcagca   1320
tctgctcaga ctccaggatg ga                                            1342
```

<210> SEQ ID NO 13
<211> LENGTH: 1407
<212> TYPE: DNA
<213> ORGANISM: Brassica napus

<400> SEQUENCE: 13

```
tccacccaag atcaacggga agaaagctaa cttgcctggt tctgcagaga tatcaaagtc     60
tgacaacgag acttcgcaac ccgcacccgc accgaggacg tttatcaacc agctgcctga    120
ctggagcatg cttctcgctg ccataacaac tatttcttac gcggctgaga aacagtggat    180
gatgcttgac tggaaaccca ggcgttctga tatgataatg gatcctttcg gtttagggag    240
aatcgttcag gatggtcttg tgtttcgtca gaatttctcc attaggtctt atgagatagg    300
```

```
tgctgatcgc tctgcgtcta tagaaactgt tatgaatcat ttacaggtag gtactacttt    360
gattgttatc acacttgtca ctggacaccc aatagatata tatgctcatg acaagctctt    420
atgctaatga caggaaacgg ccctaaacca tgtgaagtct gccggactgc tggaaaatgg    480
gtttggttct actcccgaga tgtttaagaa gaacttgata tgggtcgttg ctcgtatgca    540
ggttgtcgtt gataaatatc ctacttggta agccattgtc agtcttacca cttaacttaa    600
aatcattatg catattacag tttgcataga tcattactta ttcaaatatc tgactaacag    660
gggagatgtt gtggaagtgg atacatgggt tagtcagtcc ggaaagaatg gtatgcgtcg    720
tgattggctg gttcgggatt gcaatactgg agaaattgta acgcgagcat caaggtcaga    780
gttcttatgt tttggtttac tgactccagc tattatcatt ttgctctctg tttgtattgt    840
ttgctctgcc attaatatga taatagagac tttatagttg tatatgtatg caattttct     900
tcttttttgca gtttgtgggt gatgatgaat aaactgacaa ggagattgtc aaagattcct    960
gaagaggttc gtggggaaat agagccttat tttgtgaact ctgatcctgt cattgccgaa   1020
gacagcagaa agttaacaaa actggatgac aagactgctg actatgttcg ttcgggtctc   1080
actgtaagta ccctaccttt caacaagcct ttaaaactct tgaggttcta atggtttggt   1140
aataaacttt ttttttcagcc gagttggagt gacttagatg ttaaccagca tgttaacaat   1200
gtaaagtaca ttgggtggat actggagagt gctccagcag ggatgctgga gagtcagaag   1260
ctgaaaagca tgactctgga gtatcgcagg gagtgcggga gagacagtgt gcttcagtct   1320
ctcaccgcgg tctctggatg tgatgtcggt aacctcggga cagccgggga agtggagtgt   1380
cagcatttgc ttcgtctcca ggatgga                                        1407

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ctttgaacgc tcagctcctc agcc                                              24

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
aaacgaacca agaacccat gtttgc                                             26

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ctttgaaagc tcatcttcct cgtc                                              24

<210> SEQ ID NO 17
<211> LENGTH: 25
<212> TYPE: DNA
<213> ORGANISM: Artificial Sequence
```

```
<220> FEATURE:
<223> OTHER INFORMATION: Primer

<400> SEQUENCE: 17
ggttgcaagg tagcagcagg tacag                                         25

<210> SEQ ID NO 18
<211> LENGTH: 1557
<212> TYPE: DNA
<213> ORGANISM: Brassica napus

<400> SEQUENCE: 18
atggtggcta cttgcgctac gtcgtcgttt tttcatgttc catcttcttc ctcgcttgat   60
actaatggga aggggaacag agttgggtct actaattttg ctggacttaa ctcaacgcca  120
agctctggga ggatgaaggt taagccaaac gctcaggctc cacccaagat caacgggaag  180
aaagctaact tgcctggctc tgtagagata tcaaagtctg acaacgagac ttcgcaaccc  240
gcacacgcac cgaggacgtt tatcaaccag ctacctgact ggagcatgct tcttgctgcc  300
ataacaacta ttttcttagc ggcggagaaa cagtggatga tgcttgactg gaaacctagg  360
cgttctgata tgattatgga ccctttcggt ttagggagaa tcgttcagga tggtcttgtg  420
ttccgtcaga atttttccat taggtcttat gagataggtg ctgatcgctc tgcgtctata  480
gaaactgtca tgaatcattt acaggtactg ctttgattgt ggttacactc acatgttgtc  540
ccaatagata tatgctcatg acaagctctt atgctaatga caggaaacgg cgcttaatca  600
tgtgaagtct gccggactgc tggaaaatgg gtttgggtcc actcctgaga tgtttaagaa  660
gaatttgata tgggtcgttg ctcgtatgca ggttgtcgtt gataaatatc ctacttggta  720
agccattgtt agtcttagca cttgacttaa aatcattttg catattacag tgtgcgtaga  780
tcatttgctt attcaaatat ctgactcaca ggggagatgt tgtggaagtg gatacttggg  840
ttagtcagtc tggaaagaat ggtatgcgtc gtgattggct agttcgggat tgcaatactg  900
gagaaattgt aacgcgagca tcaaggtcag agttcttata ttttggttta ctccagctat  960
tatcgttttg ctctctgttt gtattgtttc ctctgccatt agtttgataa ttgagtcttt 1020
atagttgtat atgtatggca attttcttct ttttgcagtt tgtgggtgat gatgaataaa 1080
ctcacaagga gattgtcaaa gattcctgaa gaggttcgag gggaaataga gccttatttt 1140
gtgaactctg atcctgtcat tgccgaagac agcagaaagt taacaaaact tgatgacaag 1200
actgctgact atgttcgttc tggtctcact gtaagtacct tacctttcga caagcctgtc 1260
aaaactcttg aggttctaat ggtttggtaa tgaacttttt tttggcagcc gaggtggagt 1320
gacttggatg ttaaccagca tgttaacaat gtaaagtaca ttgggtggat actggagagt 1380
gctccagcag ggatgctgga gagtcagaag ctgaaaagca tgactctgga gtatcgcagg 1440
gagtgcggga gagacagtgt gcttcagtct ctcaccgcag tctctggatg tgatgtcggt 1500
aacctcggga cagccgggga agtggagtgt cagcatttgc ttcgactcca ggatgga    1557

<210> SEQ ID NO 19
<211> LENGTH: 1563
<212> TYPE: DNA
<213> ORGANISM: Brassica napus

<400> SEQUENCE: 19
atggtggcca cctcagctac atcctcattc ttccctctcc catctttccc cctcgacccc   60
accgcaaaaa ccaacaaagt caccacctcc accaacttct ccggcctctc ccccactcca  120
```

```
aactcctccg gcaggatgaa ggttaaacca acgctcagg ccccacccaa gatcaacggc    180
aagagagtcg gtctcccttc tggctcggtg aagcctgata acgagacgtc ctcacagcat    240
cccgcagcac cgaggacgtt catcaaccag ctgcctgact ggagcatgct tcttgctgca    300
ataacaaccg tcttcttggc ggctgagaag cagtggatga tgcttgactg gaaaccgagg    360
cgctctgacg tgattatgga tccgtttggg ttagggagga tcgttcagga tgggcttgtg    420
ttccgtcaga atttctctat tcggtcttat gagataggtg ctgatcgctc tgcgtctata    480
gaaacggtta tgaatcattt acaggtactg attatgatta tgattatgat tgtagttgct    540
tgttgttact ggacaaagtt aatatgtatt gctgttatgg ttatgatagg aaacggcact    600
caaccatgtt aagactgctg gactgcttgg agatgggttt ggttctactc tgagatggt    660
taagaagaac ttgatttggg ttgttactcg tatgcaggtt gtcgttgata aatatcctac    720
ttggtaagct attctcaagc aaccctgaga atcactgctt cctttgtcat ttgcttattc    780
aaatatctgt ctcacagggg agatgttgtg gaagtagata catgggtgag ccagtctgga    840
aagaacggta tgcgtcgtga ttggctagtt cgagatggca atactggaga aattttaaca    900
agagcatcaa ggttagattt ttatttatcg gttaggtatc tgaaaatttg agttactaat    960
gcaaaatatt atttttgcag tgtgtgggtg atgatgaata aactgacaag aagattatca   1020
aagattcctg aagaggttcg aggggagata gagccttact tgttaattc agacccagtc   1080
cttgctgagg acagcagaaa gttaactaaa cttgatgaca agactgctga ctatgttcgt   1140
tctggtctca ctgtaagtat gcatactttc tctatgtttc atcaaagcct gtaaacttct   1200
gagattctta cagttttat ttggtaattt aaacttttgc agccgcgttg gagtgacttg   1260
gatgttaacc agcacgttaa caatgtgaag tacatcgggt ggatactgga gagtgcacct   1320
gtggggatga tggagagtca gaagctgaaa agcatgactc tggagtatcg cagggagtgc   1380
gggagggaca gtgtgcttca gtccctcacc gcggtttcgg gctgcgatgt tggtagtctt   1440
gggacagctg gtgaagtgga atgtcagcac ctgctccgtc tccaggatgg agctgaagtg   1500
gtgagaggaa gaacagagtg gagttccaaa acatcaacaa caacttggga cattacaccg   1560
tga                                                                 1563
```

<210> SEQ ID NO 20
<211> LENGTH: 1572
<212> TYPE: DNA
<213> ORGANISM: Brassica napus

<400> SEQUENCE: 20

```
atggtggcca cctcagctac atcctcattc ttccctctcc catcttcccc cctcgacccc     60
accgcaaaaa ccaacaaagt caccacctcc accaacttct ccggcctcac acccacgccg    120
aactccgcca ggatgaaggt taaccaaac gctcaggccc cacccaagat caacggcaag    180
agagtcggcc tccctggctc ggtggagatc ttgaagcctg atagcgagac ttcgcaacca    240
gcaccgagga cgttcatcaa ccagctgcct gactggagca tgctcctcgc cgccatcacg    300
accgtcttct tggcggctga aagcagtgg atgatgctcg actggaaacc gaggcgttct    360
gacgtgatta tggatccgtt tgggttaggg aggatcgttc aggatgggct tgtgttccgt    420
cagaattttt ctattcggtc ttatgagata ggtgctgatc gctctgcgtc tatagaaacg    480
gttatgaatc atttacaggt actgattatg attatgattg tagtcgcttg ttgttactgg    540
acaaacttaa atatgtattg ctcttatggt tgtgatagga aacggcactc aaccatgtta    600
agactgctgg gctgcttgga gatgggtttg gttctactcc tgagatggtt aagaagaact    660
```

```
tgatatgggt tgttactcgt atgcaggttg tcgttgataa atatcctact tggtaagcta      720
ttctcaaaca actctgagaa tcactgcttc ctttgtgagt catttgctta ttcaaatatc      780
tgcctcatag gggagatgtt gtggaagtag atacatgggt gagccagtct ggaaagaacg      840
gtatgcgtcg tgattggctt gttcgggatg caatactgg agagatttta acaagagcat       900
caaggttaga ttttattttt tggtttactt gggttagata tctgataatt gagttataat      960
catctccgtg ttgtgtaaac tattcttttt gcagtgtgtg ggtgatgatg aataaactga     1020
caagaagatt atcaaagatt cctgaagagg ttcgagggga gatagagcct tactttgtta     1080
actcagaccc agtccttgcc gaggacagca gaaagttaac aaaacttgat gacaaaactg     1140
ctgtctatgt tcgttctggt ctcactgtaa gtacaaatac ttcactctat gtttcaacaa     1200
agcctgtaaa ttttttgagtc tcttacaggt ttggtaatga acttttttgca gccgcgttgg   1260 agtgacttgg atgttaacca gcacgttaac aatgtgaagt acatcgggtg gatactggag     1320
agtgctccag tggggatgat ggagagtcag aagctgaaaa gcatgactct ggagtatcgc     1380
agggagtgtg ggagagacag tgtgctccag tccctcaccg cggtttcggg ctgcgatatc     1440
ggtagcctcg ggacagccgg tgaagtgaa tgtcagcatc tgctcagact ccaggatgga      1500
gccgaagtgg tgagaggaag aacagagtgg agttccaaaa catcaacaac aacttgggac     1560
atcacaccgt ga                                                         1572

<210> SEQ ID NO 21
<211> LENGTH: 1664
<212> TYPE: DNA
<213> ORGANISM: Brassica napus

<400> SEQUENCE: 21
atggtggcta cttccgctac gtcgtcgttt tttcatgttc catcttcctc ctctcttgat       60
actaatggga aggggaacag agttgcgtcc acgaacttcg ctggacttaa ctcaacgcca      120
agctctggga ggatgaaggt taaaccaaac gctcaggctc cacccaagat caacgggaag     180
aaagctaact tgcctggttc tgcagagata tcaaagtctg acaacgagac ttcgcaaccc      240
gcacccgcac cgaggacgtt tatcaaccag ctgcctgact ggagcatgct tctcgctgcc      300
ataacaacta ttttcttagc ggctgagaaa cagtggatga tgcttgactg gaaacccagg      360
cgttctgata tgataatgga tccttttcggt ttagggagaa tcgttcagga tggtcttgtg     420
tttcgtcaga atttctccat taggtcttat gagataggtg ctgatcgctc tgcgtctata     480
gaaactgtta tgaatcattt acaggtaggt actactttga ttgttatcac acttgtcact     540
ggacacccaa tagatatata tgctcatgac aagctcttat gctaatgaca ggaaacggcc     600
ctaaaccatg tgaagtctgc cggactgctg aaaatgggt tggttctac tcccgagatg       660 tttaagaaga acttgatatg ggtcgttgct cgtatgcagg ttgtcgttga taaatatcct     720
acttggtaag ccattgtcag tcttaccact taacttaaaa tcattatgca tattacagtt     780
tgcatagatc attacttatt caaatatctg actaacaggg gagatgttgt ggaagtggat     840
acatgggtta gtcagtccgg aaagaatgg atgcgtcgtg attggctggt tcgggattgc      900
aatactggag aaattgtaac gcgagcatca aggtcagagt tcttatgttt tggtttactg     960
actccagcta ttatcatttt gctctctgtt tgtattgttt gctctgccat taatatgata    1020
atagagactt tatagttgta tatgtatggc aattttcttc tttttgcagt ttgtgggtga    1080
tgatgaataa actgacaagg agattgtcaa agattcctga gaggttcgt ggggaaatag     1140
```

-continued

```
agccttattt tgtgaactct gatcctgtca ttgccgaaga cagcagaaag ttaacaaaac    1200
tggatgacaa gactgctgac tatgttcgtt cgggtctcac tgtaagtacc ctacctttca    1260
acaagccttt aaaactcttg aggttctaat ggtttggtaa taaactttt tttcagccga    1320 gttggagtga cttagatgtt aaccagcatg ttaacaatgt aaagtacatt gggtggatac    1380
tggagagtgc tccagcaggg atgctggaga gtcagaagct gaaaagcatg actctggagt    1440
atcgcaggga gtgcgggaga gacagtgtgc ttcagtctct caccgcggtc tctggatgtg    1500
atgtcggtaa cctcgggaca gccggggaag tggagtgtca gcatttgctt cgtctccagg    1560
atggagctga agtggtgaga ggaagaacag ctgaagtggt gagaggaaga acagagtgga    1620
gttccaagat agaagcaaca acttgggaca ctgctacatc gtaa                    1664
```

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22

```
acagtggatg atgcttgact c                                               21
```

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23

```
tagtaatata cctgtaagtg g                                               21
```

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24

```
tacgatgtag tgtcccaagt tgttg                                           25
```

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25

```
tttctgtggt gtcagtgtgt ct                                              22
```

<210> SEQ ID NO 26
<211> LENGTH: 1714
<212> TYPE: DNA
<213> ORGANISM: Brassica napus

<400> SEQUENCE: 26

```
atggtggcca cctctgctac atcctcattc ttccctctcc catcttcctc tctcgacccc     60
aatggcaaaa ccaacaaagc cacctccacc aacttctccg gactcaaccc cacaccaaac    120
tcttccggca ggttaaaggt caaaccaaac gctcaggctc catccaagat caacggcaag    180
```

```
aaagtctcct tgccaggctc agtacacatc gtaaagactg ataataacca cgatctctcg      240
caacaaaacg cacccagaac gttcatcaac cagctacctg actggagcat gcttctcgcc      300
gccatcacaa cggtcttctt agcagctgag aagcagtgga tgatgcttga tactaaaccg      360
agacgctccg acatgattat ggatccgttt gggttaggga gaatcgttca ggatgggctt      420
gtgtaccgtc agaatttcga tatcaggtct tatgaaatag gtgctgatcg ctctgcatct      480
atagaaactg tcatgaatca cttacaggta tattacaatc acactcgttt gatactatag      540
cttgacccgc actgatgttg gttttatat ttttataaat tgtttagtga catatagata       600
taggttattt agatatttct aggttcctac gaacctaccc ggactcaaac cctgtccgta      660
aaattgagtt taattttaaa ccaaaaaaat ccgatacccg aaaaaaccga tctgtatcta      720
actcttgtcc tcatgacagg aaacggctct caaccatgtg aagtctgcag gactgctggg      780
agatgggttt ggttctacac ctgagatggt taagaagaac ttgatatggg ttgttactcg      840
tatgcaggtt gtagttgata atatcctac ttggtaagct ctcttgccac ttaaccttaa       900
acaatatgca tgaatcattt gcttattcaa atgtctgttt caccagggga gatgttgttg      960
aagtagatac atgggtcagt aagtctggga agaatggtat cgtcgtgat tggctagttc      1020 gtgattgcaa tactggagaa atcttaacac gcgcatcaag gttagcttta ttttgttttt      1080
gtttactcca gctattatct gattattgag ttataaccat ctctatgtta caaaacagtg      1140
tgtgggtgat gatgaataaa ctgacaagga gattatcaaa gcttcctgaa gaggttcgag      1200
gggaaataga gccttacttt gtgaactctg acccaatcct tgccgaggac agcagaaagt      1260
taacaaagct agatgacaag actgctgact atgttcgctc tggtctcacc gtaagtataa      1320
atattcaact ctttatcttt tagcgtgtaa aactcttgag agattcttat gagttttggtg     1380 atgaactttt gcagccgaga tggagtgact tggatgttaa ccagcatgtt aacaacgtga      1440
agtacattgg ttggatactc gagagtgctc cagtagagat gatggagaag cataagctga      1500
aaagcatgac tctggagtat aggagggaat gcgggagaga cagtgtgctt cagtctctca      1560
ccgcggtttc gggatgcgat gttggtagcc tcgggcagc tggtgaagtg gaatgtcagc       1620
atttgcttcg acaccaggat ggagctgaag tggtgaaggg acgaacagtg tggagttcga      1680
aaacaccatc aacaacttgg gacactacat cgta                                  1714
```

<210> SEQ ID NO 27
<211> LENGTH: 1891
<212> TYPE: DNA
<213> ORGANISM: Brassica napus

<400> SEQUENCE: 27

```
atggtggcca cctctgctac atcctcattc ttccctctcc catcttcctc tctcgaccct       60
aatggcaaaa ccaacaaact cacctccacc aacttctctg gactcaaccc cataccaaac      120
tcttccggca ggttaaaggt caaaccaaac gcccaagctc catccaagat caacggcaat      180
aatgtctcct tgccaggctc agtacacatc gtaaagactg ataataacca cgatctctcg      240
caacaacacg cacccagaac gttcatcaac cagctacctg actggagcat gcttctcgcc      300
gccatcacaa cggtcttctt agctgctgag aaacagtgga tgatgcttga ctcgaaaccg      360
aggcgttctg atatgattat ggatccgttc gggttaggga ggatcgttca ggatgggctt      420
gtgtaccgtc agaacttcga tatcaggtct tatgaaatag gtgctgatcg ctctgcgtct      480
atagaaacag tcatgaacca cttacaggta tattacaatc acactcgatt gatactagag      540
```

| | |
|---|---:|
| cttgacatgt tggtttttat cttttttataa attgtttagt gacattttca aacatataga | 600 |
| tataggttat ttagatattt ctaggttcct acaaacctac ccagactcaa acccccgtccg | 660 |
| gaaatttata atattaatac cgaacagagt tttattttaa accaaaaaat cagttgaccc | 720 |
| gcacgggatt ttggttttta tctattttat acattgttta aggacatttt taaacatata | 780 |
| aatataggtt atttagatat ttctaggttc ctacgaacct acccggaaat ttataatacc | 840 |
| cgaacatagt ttaattttta aaccaaaaaa tccaataccc gaaaaaacca atctgtgata | 900 |
| tgcatgatct aactcttgtc ctcgtgacag gaaacggctc tcaaccatgt gaagtctgct | 960 |
| ggactgctgg gagatgggtt tggttctacc cctgagatgg ttaagaagaa cttgatatgg | 1020 |
| gtcgttactc gtatgcaggt tgtcgttgat aaatatccta cttggtaagc cctcttagca | 1080 |
| cttaaccctta aaacaatatg catgaatcat ttgcttattc aaatgtctgc ttcaccaggg | 1140 |
| gagatgttgt tgaagtagat acatgggtta gtaagtctgg gaagartggt atgcgtcgtg | 1200 |
| attggcttgt tcgggattgt aatactggag aaattttaac aagagcatca aggttagctt | 1260 |
| cttttttgttt actccagcta ttatctgatt attgagttat aaccatctct gtgttgcaaa | 1320 |
| acagtgtgtg ggtgatgatg aataaagtga caaggagatt atcaaagctt cctgaagagg | 1380 |
| ttcgagggga aatagagcct tactttgtga actctgaccc tatccttgcc gaggacagca | 1440 |
| gaaagttaac aaaactagat gagaagactg ctgactatgt tcgctctggt ctcaccgtaa | 1500 |
| gtataaatat ttgtttttat cttttcagcaa gtgagattct gatgggtttg gtgattatct | 1560 |
| aacttttgca gccgagatgg agtgacttgg atgttaacca gcatgttaac aacgtgaagt | 1620 |
| acattggttg gatactcgag agtgctccag tggagatgat ggagaagcat aagctgaaaa | 1680 |
| gcatgactct ggagtatagg agggaatgcg ggagagacag tgtgcttcag tctctcaccg | 1740 |
| cggtttcggg ttgcgatgtt ggtagcctcg ggacagctgg tgaagtggaa tgtcagcatt | 1800 |
| tgcttcgact ccaggatgga gctgaagtgg tgaagggacg aacagtgtgg agttccaaaa | 1860 |
| caccatcaac aacttgggac actacatcgt a | 1891 |

<210> SEQ ID NO 28
<211> LENGTH: 1164
<212> TYPE: DNA
<213> ORGANISM: Brassica napus

<400> SEQUENCE: 28

| | |
|---|---:|
| aagtgtggat tctcgacgga tggatttgcc acaacactca ccatgaggaa attgcatctc | 60 |
| atatgggtca ctgcaagaat gcacattgag atctacaagt acccagcttg gtatttttctt | 120 |
| ttcttaggct tctttgacta gttgacactt tagaggtcgg agtttgtaaa cctcagagct | 180 |
| ttttattact tggttaacag gagtgatgtt gttgagatag agacatggtg ccagagtgaa | 240 |
| ggaaggattg gaacgagacg tgattggatt ctaagggact ctgctacaaa tgaagttatt | 300 |
| gggcgtgcta caaggtttgc caaaaacaga tttgttacta ctattcataa attcatttttt | 360 |
| ttatctgcct tcaatcaata taataatgca aatcactgac attagtcgca caacagtaac | 420 |
| tcccatatac gttgcttatt tagttataaa gacttatgca tattctggaa cctgagcttg | 480 |
| ttttttgtttg acaaatgtta catgggtctt acagcaagtg ggtgatgatg aaccaagaca | 540 |
| caaggcggct tcaaagagtt acagatgaag ttcgggacga gtacttggtt ttctgtcctc | 600 |
| gagaacccag gtgaagaaga atcatcatgc ttcccttata attgctagtt aaacagttaa | 660 |
| tatttaagca tgtggatctc aacctgttgt cctctgtatt tctcgtagac tagcgtttcc | 720 |
| agaagagaac aatagcagct taaagaaaat cccaaaacta gaagatccag ctcagtattc | 780 |

```
tatgctagag cttaagcttc ggcgagctga tctggacatg aaccagcacg tgaataacgt    840
cacctacatt ggatgggtgc ttgaggtgag taccttaata aagcctacaa aacgtctatc    900
attttaatca tacatatgag ctaactaact attaaatttg agtttggttc cctggtaatg    960
gcagagcata cctcaagaaa tcattgatac gcatgagctt caagttataa ctctagatta   1020
cagaagagaa tgccagcaag atgacattgt agattcactc accacctctg aaatccctga   1080
cgacccgatc tcaaagctta ccgggaccaa cggatctgcc acgtcaagca tacaaggaca   1140
caatgagagc cagttcttgc atat                                          1164
```

<210> SEQ ID NO 29
<211> LENGTH: 36
<212> TYPE: PRT
<213> ORGANISM: Artificial Sequence
<220> FEATURE:
<223> OTHER INFORMATION: Amino acid motif

<400> SEQUENCE: 29

Leu Glu Asp Pro Ala Gln Tyr Ser Met Leu Glu Leu Lys Pro Arg Arg
1               5                   10                  15

Ala Asp Leu Asp Met Asn Gln His Val Asn Asn Val Thr Tyr Ile Gly
            20                  25                  30

Trp Val Leu Glu
        35

<210> SEQ ID NO 30
<211> LENGTH: 367
<212> TYPE: PRT
<213> ORGANISM: Arabidopsis thaliana

<400> SEQUENCE: 30

Met Leu Lys Leu Ser Cys Asn Val Thr Asp His Ile His Asn Leu Phe
1               5                   10                  15

Ser Asn Ser Arg Arg Ile Phe Val Pro Val His Arg Gln Thr Arg Pro
            20                  25                  30

Ile Ser Cys Phe Gln Leu Lys Lys Glu Pro Leu Arg Ala Ile Leu Ser
        35                  40                  45

Ala Asp His Gly Asn Ser Ser Val Arg Val Ala Asp Thr Val Ser Gly
    50                  55                  60

Thr Ser Pro Ala Asp Arg Leu Arg Phe Gly Arg Leu Met Glu Asp Gly
65                  70                  75                  80

Phe Ser Tyr Lys Glu Lys Phe Ile Val Arg Ser Tyr Glu Val Gly Ile
                85                  90                  95

Asn Lys Thr Ala Thr Ile Glu Thr Ile Ala Asn Leu Leu Gln Glu Val
            100                 105                 110

Ala Cys Asn His Val Gln Asn Val Gly Phe Ser Thr Asp Gly Phe Ala
        115                 120                 125

Thr Thr Leu Thr Met Arg Lys Leu His Leu Ile Trp Val Thr Ala Arg
    130                 135                 140

Met His Ile Glu Ile Tyr Lys Tyr Pro Ala Trp Ser Asp Val Val Glu
145                 150                 155                 160

Ile Glu Thr Trp Cys Gln Ser Glu Gly Arg Ile Gly Thr Arg Arg Asp
                165                 170                 175

Trp Ile Leu Lys Asp Cys Ala Thr Gly Glu Val Ile Gly Arg Ala Thr
            180                 185                 190

```
Ser Lys Trp Val Met Met Asn Gln Asp Thr Arg Arg Leu Gln Arg Val
        195                 200                 205

Thr Asp Glu Val Arg Asp Glu Tyr Leu Val Phe Cys Pro Pro Glu Pro
210                 215                 220

Arg Leu Ala Phe Pro Glu Glu Asn Asn Ser Ser Leu Lys Lys Ile Pro
225                 230                 235                 240

Lys Leu Glu Asp Pro Ala Gln Tyr Ser Met Leu Gly Leu Lys Pro Arg
                245                 250                 255

Arg Ala Asp Leu Asp Met Asn Gln His Val Asn Asn Val Thr Tyr Ile
                260                 265                 270

Gly Trp Val Leu Glu Ser Ile Pro Gln Glu Ile Ile Asp Thr His Glu
                275                 280                 285

Leu Lys Val Ile Thr Leu Asp Tyr Arg Arg Glu Cys Gln Gln Asp Asp
            290                 295                 300

Ile Val Asp Ser Leu Thr Thr Ser Glu Thr Pro Asn Glu Val Val Ser
305                 310                 315                 320

Lys Leu Thr Gly Thr Asn Gly Ser Thr Thr Ser Ser Lys Arg Glu His
                325                 330                 335

Asn Glu Ser His Phe Leu His Ile Leu Arg Leu Ser Glu Asn Gly Gln
                340                 345                 350

Glu Ile Asn Arg Gly Arg Thr Gln Trp Arg Lys Lys Ser Ser Arg
                355                 360                 365

<210> SEQ ID NO 31
<211> LENGTH: 223
<212> TYPE: PRT
<213> ORGANISM: Brassica napus

<400> SEQUENCE: 31

Gly Phe Ser Thr Asp Gly Phe Ala Thr Thr Leu Thr Met Arg Lys Leu
1               5                   10                  15

His Leu Ile Trp Val Thr Ala Arg Met His Ile Glu Ile Tyr Lys Tyr
                20                  25                  30

Pro Ala Trp Ser Asp Val Val Glu Ile Glu Thr Trp Cys Gln Ser Glu
            35                  40                  45

Gly Arg Ile Gly Thr Arg Arg Asp Trp Ile Leu Arg Asp Ser Ala Thr
        50                  55                  60

Asn Glu Val Ile Gly Arg Ala Thr Ser Lys Trp Val Met Met Asn Gln
65                  70                  75                  80

Asp Thr Arg Arg Leu Gln Arg Val Thr Asp Glu Val Arg Asp Glu Tyr
                85                  90                  95

Leu Val Phe Cys Pro Arg Glu Pro Arg Leu Ala Phe Pro Glu Glu Asn
            100                 105                 110

Asn Ser Ser Leu Lys Lys Ile Pro Lys Leu Glu Asp Pro Ala Gln Tyr
        115                 120                 125

Ser Met Leu Glu Leu Lys Pro Arg Arg Ala Asp Leu Asp Met Asn Gln
130                 135                 140

His Val Asn Asn Val Thr Tyr Ile Gly Trp Val Leu Glu Ser Ile Pro
145                 150                 155                 160

Gln Glu Ile Ile Asp Thr His Glu Leu Gln Val Ile Thr Leu Asp Tyr
                165                 170                 175

Arg Arg Glu Cys Gln Gln Asp Asp Ile Val Asp Ser Leu Thr Thr Ser
            180                 185                 190
```

Glu Ile Pro Asp Asp Pro Ile Ser Lys Leu Thr Gly Thr Asn Gly Ser
    195                 200                 205

Ala Thr Ser Ser Ile Gln Gly His Asn Glu Ser Gln Phe Leu His
    210                 215                 220

<210> SEQ ID NO 32
<211> LENGTH: 1163
<212> TYPE: DNA
<213> ORGANISM: Brassica napus

<400> SEQUENCE: 32

| | | | | | |
|---|---|---|---|---|---|
| aagtgtggat | tctcgacgga | tggatttgcc | acaacactca | ccatgaggaa | attgcatctc |   60 |
| atatgggtca | ctgcaagaat | gcacattgag | atctacaagt | acccagcttg | gtattttctt |  120 |
| ttcttaggct | tctttgacta | gttgacactt | tagaggtcgg | agtttgtaaa | cctcagagct |  180 |
| ttttattact | tggttaacag | gagtgatgtt | gttgagatag | agacatggtg | ccagagtgaa |  240 |
| ggaaggattg | gaacgagacg | tgattggatt | ctaaggggact | ctgctacaaa | tgaagttatt |  300 |
| gggcgtgcta | caaggtttgc | caaaaacaga | tttgttacta | ctattcataa | attcattttt |  360 |
| ttatctgcct | tcaatcaata | taataatgca | aatcactgac | attagtcgca | caacagtaac |  420 |
| tcccatatac | gttgcttatt | tagttataaa | gacttatgca | tattctggaa | cctgagcttg |  480 |
| tttttgtttg | acaaatgtta | catgggtctt | acagcaagtg | ggtgatgatg | aaccaagaca |  540 |
| caaggcggct | tcaaagagtt | acagatgaag | ttcgggacga | gtacttggtt | ttctgtcctc |  600 |
| gagaacccag | gtgaagaaga | gtcatcatgc | ttcccttata | attgctagtt | aaacagttaa |  660 |
| tatttaagca | tgtggatctc | aacctgttgt | tctctgtatt | tctcgtagac | tagcgtttcc |  720 |
| agaagagaac | aatagcagct | taaagaaaat | cccaaaacta | aagatccag | ctcagtattc |  780 |
| tatgctagag | cttaagcttc | ggcgagctga | tctggacatg | aaccagcacg | tgaataacgt |  840 |
| cacctacatt | ggatgggtgc | ttgaggtgag | taccttaata | aagcctacaa | aacgtctatc |  900 |
| attttaatca | tacatatgag | ctaactaact | attaaatttg | agtttggttc | cctggtaatg |  960 |
| gcagagcata | cctcaagaaa | tcattgatac | gcatgagctt | caagttataa | ctctagatta | 1020 |
| cagaagagaa | tgccagcaag | atgacattgt | agattcactc | accacctctg | aaatccctga | 1080 |
| cgacccgatc | tcaaagctta | ccgggaccaa | cggatctgcc | acgtcaagca | tacaaggaca | 1140 |
| caatgagagc | cagttcttgc | ata | | | | 1163 |

<210> SEQ ID NO 33
<211> LENGTH: 86
<212> TYPE: DNA
<213> ORGANISM: Brassica rapa

<400> SEQUENCE: 33

| | | | | | |
|---|---|---|---|---|---|
| ctcagtattc | gatgattggg | cttaagccta | gacgagctga | tctcgacatg | aaccaggatg |   60 |
| tcaataatgt | cacctatatt | ggatgg | | | |   86 |

<210> SEQ ID NO 34
<211> LENGTH: 86
<212> TYPE: DNA
<213> ORGANISM: Arabidopsis thaliana

<400> SEQUENCE: 34

| | | | | | |
|---|---|---|---|---|---|
| ctcagtattc | aatgattggg | cttaagccta | gacgagctga | tctcgacatg | aaccagcatg |   60 |
| tcaataatgt | cacctatatt | ggatgg | | | |   86 |

```
<210> SEQ ID NO 35
<211> LENGTH: 83
<212> TYPE: DNA
<213> ORGANISM: Brassica napus

<400> SEQUENCE: 35
tttataatca tgtttctttg cagccaagac gagctgatct cgacatgaac catcatgtca    60
ataatgtcac ctatattgga tgg                                            83

<210> SEQ ID NO 36
<211> LENGTH: 86
<212> TYPE: DNA
<213> ORGANISM: Arabidopsis thaliana

<400> SEQUENCE: 36
ctcagtattc tatgcttggg cttaagccta gacgagctga tcttgacatg aaccaacatg    60
tgaataatgt tacctacatt ggatgg                                         86

<210> SEQ ID NO 37
<211> LENGTH: 86
<212> TYPE: DNA
<213> ORGANISM: Brassica napus

<400> SEQUENCE: 37
ctcagtattc tatgctagag cttaagcctc ggcgagctga tctggacatg aaccagcacg    60
tgaataacgt cacctacatt ggatgg                                         86

<210> SEQ ID NO 38
<211> LENGTH: 66
<212> TYPE: DNA
<213> ORGANISM: Brassica napus

<400> SEQUENCE: 38
ttaagcctcg gcgagctgat ctggacatga accagcacgt gaataacgtc acctacatcg    60
gatggg                                                               66

<210> SEQ ID NO 39
<211> LENGTH: 86
<212> TYPE: DNA
<213> ORGANISM: Brassica napus

<400> SEQUENCE: 39
ctcagtattc tatgctagag cttaagcttc ggcgagctga tctggacatg aaccagcacg    60
tgaataacgt cacctacatt ggatgg                                         86

<210> SEQ ID NO 40
<211> LENGTH: 66
<212> TYPE: DNA
<213> ORGANISM: Brassica napus

<400> SEQUENCE: 40
ttaagcttcg gcgagctgat ctggacatga accagcacgt gaataacgtc acctacattg    60
gatggg                                                               66

<210> SEQ ID NO 41
<211> LENGTH: 66
<212> TYPE: DNA
<213> ORGANISM: Arabidopsis thaliana

<400> SEQUENCE: 41
```

```
ttaagcctag acgagctgat cttgacatga accaacatgt gaataatgtt acctacattg    60
gatggg                                                                66

<210> SEQ ID NO 42
<211> LENGTH: 66
<212> TYPE: DNA
<213> ORGANISM: Brassica napus

<400> SEQUENCE: 42
ttaagcctcg gcgagctgat ctggacatga accagcacgt gaataacgtc acctacatcg    60
gatggg                                                                66

<210> SEQ ID NO 43
<211> LENGTH: 66
<212> TYPE: DNA
<213> ORGANISM: Brassica napus

<400> SEQUENCE: 43
ttaagcctcg gcgagctgat ctggacatga accagcacgt gaataacgtc acctacattg    60
gatggg                                                                66

<210> SEQ ID NO 44
<211> LENGTH: 310
<212> TYPE: DNA
<213> ORGANISM: Brassica napus

<400> SEQUENCE: 44
gtttccagaa gagaacaata gcagcttaaa gaaaatccca aaactagaag atccagctca    60
gtattctatg ctagagctta agcctcggcg agctgatctg gacatgaacc agcacgtgaa   120
taacgtcacc tacatcggat gggtgcttga ggtgagtaac ttaataaagc cttcaaaacg   180
tctatcattt taataatgag ctaactatta aatttgagtt tggttccttg gtaatggcag   240
agcataccct caagaaatcat tgatacgcat gagcttcaag ttataactct agattacaga   300
agagaatgcc                                                           310

<210> SEQ ID NO 45
<211> LENGTH: 320
<212> TYPE: DNA
<213> ORGANISM: Brassica napus

<400> SEQUENCE: 45
gtttccagaa gagaacaata gcagcttaaa gaaaatccca aagctagaag atccagctca    60
gtattctatg ctagagctta agcctcggcg agctgatctg gacatgaacc agcacgtgaa   120
taacgtcacc tacattggat gggtgcttga ggtgagtacc ttaataaagc ctacaaaacg   180
tctatcattt taatcataca tatgagctaa ctaactatta aatttgagtt tggttccctg   240
gtaatggcag agcataccct caagaaatcat tgatacgcat gagcttcaag ttataactct   300
agattacaga agagaatgcc                                                320

<210> SEQ ID NO 46
<211> LENGTH: 310
<212> TYPE: DNA
<213> ORGANISM: Brassica napus

<400> SEQUENCE: 46
gtttccagaa gagaacaata gcagcttaaa gaaaatccca aaactagaag atccagctca    60
```

```
gtattctatg ctagagctta agcctcggcg agctgatctg acatgaacc agcacgtgaa      120 taacgtcacc tacatcggat gggtgcttga ggtgagtaac ttaataaagc cttcaaaacg      180
tctatcattt taataatgag ctaactatta aatttgagtt tggtcccttg gtaatggcag      240
agcatacctc aagaaatcat tgatacgcat gagcttcaag ttataactct agattacaga      300
agagaatgcc                                                             310
```

<210> SEQ ID NO 47
<211> LENGTH: 320
<212> TYPE: DNA
<213> ORGANISM: Brassica napus

<400> SEQUENCE: 47

```
gtttccagaa gagaacaata gcagcttaaa gaaaatccca aaactagaag atccagctca       60
gtattctatg ctagagctta agcttcggcg agctgatctg acatgaacc agcacgtgaa      120 taacgtcacc tacattggat gggtgcttga ggtgagtacc ttaataaagc ctacaaaacg      180
tctatcattt taatcataca tatgagctaa ctaactatta aatttgagtt tggttccctg      240
gtaatggcag agcatacctc aagaaatcat tgatacgcat gagcttcaag ttataactct      300
agattacaga agagaatgcc                                                  320
```

<210> SEQ ID NO 48
<211> LENGTH: 36
<212> TYPE: PRT
<213> ORGANISM: Arabidopsis thaliana

<400> SEQUENCE: 48

```
Leu Glu Asp Pro Ala Gln Tyr Ser Met Leu Gly Leu Lys Pro Arg Arg
1               5                   10                  15

Ala Asp Leu Asp Met Asn Gln His Val Asn Asn Val Thr Tyr Ile Gly
            20                  25                  30

Trp Val Leu Glu
        35
```

<210> SEQ ID NO 49
<211> LENGTH: 36
<212> TYPE: PRT
<213> ORGANISM: Brassica napus

<400> SEQUENCE: 49

```
Leu Glu Asp Pro Ala Gln Tyr Ser Met Leu Glu Leu Lys Leu Arg Arg
1               5                   10                  15

Ala Asp Leu Asp Met Asn Gln His Val Asn Asn Val Thr Tyr Ile Gly
            20                  25                  30

Trp Val Leu Glu
        35
```

<210> SEQ ID NO 50
<211> LENGTH: 36
<212> TYPE: PRT
<213> ORGANISM: Brassica napus

<400> SEQUENCE: 50

```
Leu Glu Asp Pro Ala Gln Tyr Ser Met Leu Glu Leu Lys Pro Arg Arg
1               5                   10                  15

Ala Asp Leu Asp Met Asn Gln His Val Asn Asn Val Thr Tyr Ile Gly
            20                  25                  30
```

```
<210> SEQ ID NO 51
<211> LENGTH: 36
<212> TYPE: PRT
<213> ORGANISM: Brassica napus

<400> SEQUENCE: 51

Leu Glu Asp Pro Ala Gln Tyr Ser Met Leu Glu Leu Lys Pro Arg Arg
1               5                   10                  15

Ala Asp Leu Asp Met Asn Gln His Val Asn Asn Val Thr Tyr Ile Gly
            20                  25                  30

Trp Val Leu Glu
        35

<210> SEQ ID NO 52
<211> LENGTH: 36
<212> TYPE: PRT
<213> ORGANISM: Brassica napus

<400> SEQUENCE: 52

Leu Glu Asp Pro Ala Gln Tyr Ser Met Leu Glu Leu Lys Pro Arg Arg
1               5                   10                  15

Ala Asp Leu Asp Met Asn Gln His Val Asn Asn Val Thr Tyr Ile Gly
            20                  25                  30

Trp Val Leu Glu
        35
```